US012744137B2

(12) United States Patent
Ge et al.

(10) Patent No.: US 12,744,137 B2
(45) Date of Patent: Sep. 22, 2026

(54) ACCURATE AND COMPREHENSIVE CARDIAC TROPONIN I ASSAY ENABLED BY NANOTECHNOLOGY AND PROTEOMICS

(71) Applicant: Wisconsin Alumni Research Foundation, Madison, WI (US)

(72) Inventors: Ying Ge, Madison, WI (US); Song Jin, Madison, WI (US); Timothy-Neil T. Tiambeng, Madison, WI (US); David S. Roberts, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1102 days.

(21) Appl. No.: 17/786,482

(22) PCT Filed: Dec. 18, 2020

(86) PCT No.: PCT/US2020/066011

§ 371 (c)(1),
(2) Date: Jun. 16, 2022

(87) PCT Pub. No.: WO2021/127434

PCT Pub. Date: Jun. 24, 2021

(65) Prior Publication Data

US 2023/0035606 A1 Feb. 2, 2023

Related U.S. Application Data

(60) Provisional application No. 62/949,869, filed on Dec. 18, 2019.

(51) Int. Cl.

| | |
|---|---|
| ***H01F 1/00*** | (2006.01) |
| ***A61K 9/14*** | (2006.01) |
| ***G01N 33/543*** | (2006.01) |
| ***G01N 33/68*** | (2006.01) |
| ***G01N 33/90*** | (2006.01) |
| ***H01F 1/36*** | (2006.01) |

(52) U.S. Cl.

CPC ............. *H01F 1/0054* (2013.01); *A61K 9/14* (2013.01); *G01N 33/54333* (2013.01); *G01N 33/68* (2013.01); *G01N 33/90* (2013.01); *H01F 1/36* (2013.01); *G01N 2333/4712* (2013.01); *G01N 2800/324* (2013.01)

(58) Field of Classification Search

None

See application file for complete search history.

(56) References Cited

U.S. PATENT DOCUMENTS

| | | | | |
|---|---|---|---|---|
| 2008/0261242 A1* | 10/2008 | Goix | G01N 33/68 436/536 |
| 2009/0148860 A1 | 6/2009 | Van Eyk et al. | |
| 2011/0130616 A1 | 6/2011 | Seeney et al. | |
| 2012/0046184 A1 | 2/2012 | Dawson et al. | |
| 2013/0150707 A1* | 6/2013 | Cima | A61B 5/055 600/420 |
| 2019/0062830 A1 | 2/2019 | Nikiforov et al. | |

FOREIGN PATENT DOCUMENTS

| | | | |
|---|---|---|---|
| RU | 2675540 C1 * | 12/2018 | C08L 23/00 |
| WO | WO 2004/034060 | 4/2004 | |
| WO | WO 2010/042126 | 4/2010 | |
| WO | WO 2011/103330 | 8/2011 | |
| WO | WO 2019/155041 | 8/2019 | |

OTHER PUBLICATIONS

Harlow, E. and Lane, D., Antibodies: A Laboratory Manual (1988) Cold Spring Harbor Laboratory Press, Cold Spring Harbor, NY, pp. 23-26 (Year: 1988).*

Lederman et al., "A single amino acid substitution in a common African allele of the CD4 molecule ablates binding of the monoclonal antibody, OKT4" Mol Immunol. Nov. 1991;28(11):1171-81 (Year: 1991).*

Brown et al. ("Tolerance of single, but not multiple, amino acid replacements in antibody VH CDR 2: a means of minimizing B cell wastage from somatic hypermutation?", J Immunol. May 1996;156(9):3285-91) (Year: 1996).*

Lucchese et al., How a single amino acid change may alter the immunological information of a peptide, Frontiers in Bioscience E4, (2012), p. 1843-1852 (Year: 2012).*

Schneck et al., Quantification of cardiac troponin I in human plasma by immunoaffinity enrichment and targeted mass spectrometry, Anal Bioanal Chem, 410(11), (2018), p. 2805-2813 (Year: 2018).*

Schneck, Quantification of antibody coupled to magnetic particles by targeted mass spectrometry, Anal. Bioanal. Chem., 408, (2016), p. 8325-8332 (Year: 2016).*

(Continued)

*Primary Examiner* — Ellen J Marcsisin

(74) *Attorney, Agent, or Firm* — LEYDIG, VOIT & MAYER, LTD.

(57) ABSTRACT

This invention provides mass spectrometry (MS) compatible nanomaterials for the selective capture and enrichment of low abundance proteins as well as MS analysis of different proteoforms of proteins, particularly cardiac proteins and different proteoforms of cardiac troponin I (cTnI) arising from post-translational modifications and sequence variations. The surface of superparamagnetic nanoparticles is functionalized with probe molecules that specifically bind to the desired protein. In an embodiment, the nanoparticles are functionalized with probe molecules having high affinity and selectivity for cTnI within the human cardiac troponin complex. This allows for MS-analysis and characterization of cTnI proteoforms from human heart tissue lysates and human blood or serum samples, and provides an accurate assay for detection of cTnI with molecular details. Such assays are useful for accurate diagnosis of acute coronary syndrome and chronic diseases, including acute myocardial infarction and other cardiac injuries, as well as risk stratification and outcome assessment for patients.

11 Claims, 38 Drawing Sheets

Specification includes a Sequence Listing.

(56) References Cited

OTHER PUBLICATIONS

Extended European Search Report dated Dec. 29, 2023 in corresponding European Application No. 20903171.5.
Abbas et al. (2014) Allenamides as Orthogonal Handles for Selective Modification of Cysteine in Peptides and Proteins. Angewandte Chemie International Edition 53, 7491-7494.
Anderson et al. (2002) The Human Plasma Proteome. History, Character, and Diagnostic Prospects 1, 845-867.
Antman et al. (1996) Cardiac-Specific Troponin I Levels to Predict the Risk of Mortality in Patients with Acute Coronary Syndromes. New England Journal of Medicine 335, 1342-1349.
Apple et al. (2012) Analytical Characteristics of High-Sensitivity Cardiac Troponin Assays. Clinical Chemistry 58, 54-61.
Apple et al. (Jan. 2017) "Cardiac Troponin Assays: Guide to Understanding Analytical Characteristics and Their Impact on Clinical Care," Clinical Chemistry 63:1, 73-81.
Bates et al. (2010) Circulating Immunoreactive Cardiac Troponin Forms Determined by Gel Filtration Chromatography after Acute Myocardial Infarction. Clinical Chemistry 56, 952.
Benjamin et al. (Mar. 2018) Heart Disease and Stroke Statistics—2018 Update: A Report From the American Heart Association. Circulation 137, e67-e492.
Cai et al. (2016) MASH Suite Pro: A Comprehensive Software Tool for Top-Down Proteomics, Molecular & Cellular Proteomics, 15(2): 703-714.
Chen et al. (Jan. 2018) Top-Down Proteomics: Ready for Prime Time? Analytical Chemistry 90, 110-127.
Dong et al. (2012) Augmented Phosphorylation of Cardiac Troponin I in Hypertensive Heart Failure. Journal of Biological Chemistry 287, 848-857.
Herman et al. (Sep. 2017) Variability and Error in Cardiac Troponin Testing, American Journal of Clinical Pathology, 148 (4): 281-295.
Hyytiä et al. (2015) Skeletal troponin I cross-reactivity in different cardiac troponin I assay versions, Clinical Biochemistry, 48(4): 313-317.
International Search Report and Written Opinion mailed Mar. 17, 2021 in International Application No. PCT/US2020/066011 from which the present application claims priority, 13 pp.
Katrukha et al. (1998) Degradation of cardiac troponin I: implication for reliable immunodetection. Clinical Chemistry 44, 2433-2440.
Kelleher et al. (2014) Deep and quantitative top-down proteomics in clinical and translational research. Expert Review of Proteomics 11, 649-651.
Kuhn et al. (2009) Developing Multiplexed Assays for Troponin I and Interleukin-33 in Plasma by Peptide Immunoaffinity Enrichment and Targeted Mass Spectrometry. Clinical Chemistry 55, 1108-1117.
Labugger et al. (2000) Extensive Troponin I and T Modification Detected in Serum From Patients With Acute Myocardial Infarction. Circulation 102, 1221-1226.
Lemos et al. (2013) Increasingly Sensitive Assays for Cardiac Troponins: A Review, JAMA, 309:2262-2269.
Lin et al. (Mar. 2019) Simultaneous Quantification of Protein Expression and Modifications by Top-down Targeted Proteomics: A Case of the Sarcomeric Subproteome, Molecular & Cellular Proteomics, 18(3): 594-605.
Madsen et al. (2006) Time Course of Degradation of Cardiac Troponin I in Patients With Acute ST-Elevation Myocardial Infarction. Circulation Research 99, 1141-1147.
Missov et al. (1997) Circulating Cardiac Troponin I in Severe Congestive Heart Failure. Circulation 96, 2953-2958.
Park et al. (2004) Ultra-large-scale syntheses of monodisperse nanocrystals. Nature Materials 3, 891-895.
Park et al. (Dec. 2017) Cardiac troponins: from myocardial infarction to chronic disease, Cardiovasc. Res., 113, 1708.
Rifai et al. (2006) Protein biomarker discovery and validation: the long and uncertain path to clinical utility. Nature Biotechnology 24, 971-983.
Roberts et al. (Jul. 2019) "Reproducible Large-Scale Synthesis of Surface Silanized Nanoparticles as an Enabling Nanoproteomics Platform: Enrichment of the Human Heart Phosphoproteome," Nano Res. 12(6): 1473-1481.
Sandor et al. (2016) "Aminopropyl-Silica Hybrid Particles as Supports for Humic Acids Immobilization," Materials, 9, 34: doi:10.3390/ma9010034.
Schneck et al. (Mar. 2018) "Quantification of cardiac troponin I in human plasma by immunoaffinity enrichment and targeted mass spectrometry," Analytical and Bioanalytical Chemistry 410: 2805-2813.
Siuti et al. (2007) Decoding protein modifications using top-down mass spectrometry. Nature Methods 4, 817-821.
Smith et al. (2013) Proteoform: a single term describing protein complexity. Nature Methods 10, 186-187.
Smith et al. (Apr. 2017) Emerging Affinity-Based Proteomic Technologies for Large-Scale Plasma Profiling in Cardiovascular Disease. Circulation 135, 1651-1664.
Soetkamp et al. (Oct. 2017) "The continuing evolution of cardiac troponin I biomarker analysis: from protein to proteoform," Expert Rev Proteomics 14: 973-986.
Tadepalli et al. Peptide Functionalized Gold Nanorods for the Sensitive Detection of a Cardiac Biomarker Using Plasmonic Paper Devices. Sci Rep 5, 16206 (2015).
Taimbeng et al. (Aug. 2020) "Nanoproteomics enables proteoform-resolved analysis of low-abundance proteins in human serum," Nature Communications 11:3903. https://doi.org/10.1038/s41467-020-17643-1.
Tighe et al. (2015) ELISA in the multiplex era: Potentials and pitfalls. Proteomics Clinical Applications 9, 406-422.
Twerenbold et al. (Aug. 2017) Clinical Use of High-Sensitivity Cardiac Troponin in Patients With Suspected Myocardial Infarction. Journal of the American College of Cardiology 70, 996-1012.
Walkey et al. (2012) Understanding and controlling the interaction of nanomaterials with proteins in a physiological environment. Chemical Society Reviews 41, 2780-2799.
Westermann et al. (Aug. 2017) High-sensitivity assays for troponin in patients with cardiac disease. Nature Reviews Cardiology 14, 472-483.
Wilson et al. (May 2017) Overuse of Troponin? A Comprehensive Evaluation of Testing in a Large Hospital System, J. Hosp Med, 12, 5, 329-331.
Xie et al. (2009) Emerging affinity-based techniques in proteomics. Expert Review of Proteomics 6, 573-583 (2009).
Zabrouskov et al. (2008) Unraveling Molecular Complexity of Phosphorylated Human Cardiac Troponin I by Top Down Electron Capture Dissociation/Electron Transfer Dissociation Mass Spectrometry. Mol Cell Proteomics 7, 1838-1849.
Zaidi et al. (2010) False positive cardiac troponin elevation due to heterophile antibodies: more common than we recognise? BMJ Case Rep., 2010:bcr1120092477.
Zhang et al. (1995) Phosphorylation of Both Serine Residues in Cardiac Troponin I Is Required to Decrease the Ca2+ Affinity of Cardiac Troponin C. Journal of Biological Chemistry 270, 30773-30780.
Zhang et al. (2011) Top-Down Quantitative Proteomics Identified Phosphorylation of Cardiac Troponin I as a Candidate Biomarker for Chronic Heart Failure. Journal of Proteome Research 10, 4054-4065.
Es-Sebbar et al. (2014) "Quantitative mid-infrared spectra of allene and propyne from room to high temperatures," Journal of Molecular Spectroscopy 305, 10-16.
Thygesen et al. (Oct. 2018) "Fourth Universal Definition of Myocardial Infarction," Journal of the American College of Cardiology, 72(18):2231-2264.
Xiao et al. (May 2018) "Advancing Peptide-Based Biorecognition Elements for Biosensors Using in-Silico Evolution," ACS Sensors 3: 1024-1031.

* cited by examiner (i) NP-Control (no peptide)
(ii) NP, Peptide pH 5.0 (*HWQIAYNEHQWQC*)
(iii) Neg-Pep(-) pH 8.0 (*HWNMAANEHMQWC*)
(iv) NP-Pep pH 8.0 (*HWQIAYNEHQWQC*)

a b

| cTnI Amount (ng) | Proteoform | Observed Mass ($M_r$, Da) | Calculated Mass ($M_r$, Da) | Mass Error (ppm) |
|---|---|---|---|---|
| 0.78 | *pp*cTnI | 24063.66 | 24063.73 | 2.6 |
| 0.31 | *pp*cTnI | 24063.65 | 24063.73 | 3.3 |
| 0.155 | *pp*cTnI | 24063.66 | 24063.73 | 2.8 |
| 0.062 | *pp*cTnI | 24063.66 | 24063.73 | 2.8 |
| 0.031 | *pp*cTnI | 24063.66 | 24063.73 | 2.7 |
| 0.0155 | *pp*cTnI | 24063.64 | 24063.73 | 3.7 |
| 0.0062 | *pp*cTnI | 24063.67 | 24063.73 | 2.3 |

a b c

| Sample | Sample Source | cTnI Enrichment Factor | Total cTnI Amount Before Enrichment (ng) | Total cTnI Amount Recovered After Enrichment (ng) | cTnI Percent Recovery (%) |
|---|---|---|---|---|---|
| NP-Pep | Tissue | 1.7 | | 268 | 89 |
| NP-Pep | Serum | 115 | 302 | 153 | 51 |
| Agarose -mAb | Serum | 39 | | 53 | 17 |

SEQUENCE LISTING

```
<160> NUMBER OF SEQ ID NOS: 6

<210> SEQ ID NO 1
<211> LENGTH: 12
<212> TYPE: PRT
<213> ORGANISM: Artificial sequence
<220> FEATURE:
<223> OTHER INFORMATION: Synthetic construct

<400> SEQUENCE: 1

His Trp Gln Ile Ala Tyr Asn Glu His Gln Trp Gln
1               5                   10


<210> SEQ ID NO 2
<211> LENGTH: 13
<212> TYPE: PRT
<213> ORGANISM: Artificial sequence
<220> FEATURE:
<223> OTHER INFORMATION: Synthetic construct

<400> SEQUENCE: 2

His Trp Gln Ile Ala Tyr Asn Glu His Gln Trp Gln Cys
1               5                   10


<210> SEQ ID NO 3
<211> LENGTH: 13
<212> TYPE: PRT
<213> ORGANISM: Artificial sequence
<220> FEATURE:
<223> OTHER INFORMATION: Synthetic construct

<400> SEQUENCE: 3

His Trp Asn Met Ala Ala Asn Glu His Met Gln Trp Cys
1               5                   10


<210> SEQ ID NO 4
<211> LENGTH: 209
<212> TYPE: PRT
<213> ORGANISM: Homo sapiens
<220> FEATURE:
<221> NAME/KEY: MISC_FEATURE
<222> LOCATION: (22)..(23)
<223> OTHER INFORMATION: phosphorylated

<400> SEQUENCE: 4

Ala Asp Gly Ser Ser Asp Ala Ala Arg Glu Pro Arg Pro Ala Pro Ala
1               5                   10                  15

Pro Ile Arg Arg Arg Ser Ser Asn Tyr Arg Ala Tyr Ala Thr Glu Pro
            20                  25                  30

His Ala Lys Lys Lys Ser Lys Ile Ser Ala Ser Arg Lys Leu Gln Leu
        35                  40                  45

Lys Thr Leu Leu Leu Gln Ile Ala Lys Gln Glu Leu Glu Arg Glu Ala
    50                  55                  60

Glu Glu Arg Arg Gly Glu Lys Gly Arg Ala Leu Ser Thr Arg Cys Gln
65                  70                  75                  80

Pro Leu Glu Leu Ala Gly Leu Gly Phe Ala Glu Leu Gln Asp Leu Cys
                85                  90                  95

Arg Gln Leu His Ala Arg Val Asp Lys Val Asp Glu Glu Arg Tyr Asp
            100                 105                 110

Ile Glu Ala Lys Val Thr Lys Asn Ile Thr Glu Ile Ala Asp Leu Thr
        115                 120                 125

Gln Lys Ile Phe Asp Leu Arg Gly Lys Phe Lys Arg Pro Thr Leu Arg
    130                 135                 140
```

```
Arg Val Arg Ile Ser Ala Asp Ala Met Met Gln Ala Leu Leu Gly Ala
145                 150                 155                 160

Arg Ala Lys Glu Ser Leu Asp Leu Arg Ala His Leu Lys Gln Val Lys
                165                 170                 175

Lys Glu Asp Thr Glu Lys Glu Asn Arg Glu Val Gly Asp Trp Arg Lys
            180                 185                 190

Asn Ile Asp Ala Leu Ser Gly Met Glu Gly Arg Lys Lys Lys Phe Glu
        195                 200                 205

Ser


<210> SEQ ID NO 5
<211> LENGTH: 209
<212> TYPE: PRT
<213> ORGANISM: Homo sapiens

<400> SEQUENCE: 5

Ala Asp Gly Ser Ser Asp Ala Ala Arg Glu Pro Arg Pro Ala Pro Ala
1               5                   10                  15

Pro Ile Arg Arg Arg Ser Ser Asn Tyr Arg Ala Tyr Ala Thr Glu Pro
            20                  25                  30

His Ala Lys Lys Lys Ser Lys Ile Ser Ala Ser Arg Lys Leu Gln Leu
        35                  40                  45

Lys Thr Leu Leu Leu Gln Ile Ala Lys Gln Glu Leu Glu Arg Glu Ala
    50                  55                  60

Glu Glu Arg Arg Gly Glu Lys Gly Arg Ala Leu Ser Thr Arg Cys Gln
65                  70                  75                  80

Pro Leu Glu Leu Ala Gly Leu Gly Phe Ala Glu Leu Gln Asp Leu Cys
                85                  90                  95

Arg Gln Leu His Ala Arg Val Asp Lys Val Asp Glu Glu Arg Tyr Asp
            100                 105                 110

Ile Glu Ala Lys Val Thr Lys Asn Ile Thr Glu Ile Ala Asp Leu Thr
        115                 120                 125

Gln Lys Ile Phe Asp Leu Arg Gly Lys Phe Lys Arg Pro Thr Leu Arg
    130                 135                 140

Arg Val Arg Ile Ser Ala Asp Ala Met Met Gln Ala Leu Leu Gly Ala
145                 150                 155                 160

Arg Ala Lys Glu Ser Leu Asp Leu Arg Ala His Leu Lys Gln Val Lys
                165                 170                 175

Lys Glu Asp Thr Glu Lys Glu Asn Arg Glu Val Gly Asp Trp Arg Lys
            180                 185                 190

Asn Ile Asp Ala Leu Ser Gly Met Glu Gly Arg Lys Lys Lys Phe Glu
        195                 200                 205

Ser


<210> SEQ ID NO 6
<211> LENGTH: 205
<212> TYPE: PRT
<213> ORGANISM: Homo sapiens

<400> SEQUENCE: 6

Ala Asp Gly Ser Ser Asp Ala Ala Arg Glu Pro Arg Pro Ala Pro Ala
1               5                   10                  15

Pro Ile Arg Arg Arg Ser Ser Asn Tyr Arg Ala Tyr Ala Thr Glu Pro
            20                  25                  30

His Ala Lys Lys Lys Ser Lys Ile Ser Ala Ser Arg Lys Leu Gln Leu
```

-continued

```
        35                  40                  45

Lys Thr Leu Leu Leu Gln Ile Ala Lys Gln Glu Leu Glu Arg Glu Ala
    50                  55                  60

Glu Glu Arg Arg Gly Glu Lys Gly Arg Ala Leu Ser Thr Arg Cys Gln
65                  70                  75                  80

Pro Leu Glu Leu Ala Gly Leu Gly Phe Ala Glu Leu Gln Asp Leu Cys
                85                  90                  95

Arg Gln Leu His Ala Arg Val Asp Lys Val Asp Glu Glu Arg Tyr Asp
            100                 105                 110

Ile Glu Ala Lys Val Thr Lys Asn Ile Thr Glu Ile Ala Asp Leu Thr
        115                 120                 125

Gln Lys Ile Phe Asp Leu Arg Gly Lys Phe Lys Arg Pro Thr Leu Arg
    130                 135                 140

Arg Val Arg Ile Ser Ala Asp Ala Met Met Gln Ala Leu Leu Gly Ala
145                 150                 155                 160

Arg Ala Lys Glu Ser Leu Asp Leu Arg Ala His Leu Lys Gln Val Lys
                165                 170                 175

Lys Glu Asp Thr Glu Lys Glu Asn Arg Glu Val Gly Asp Trp Arg Lys
            180                 185                 190

Asn Ile Asp Ala Leu Ser Gly Met Glu Gly Arg Lys Lys
        195                 200                 205
```

ACCURATE AND COMPREHENSIVE CARDIAC TROPONIN I ASSAY ENABLED BY NANOTECHNOLOGY AND PROTEOMICS

CROSS-REFERENCE TO RELATED APPLICATIONS

This application is a U.S. National Stage Application filed under 35 U.S.C. § 371 of International Application No. PCT/US2020/066011, filed Dec. 18, 2020, which claims the benefit of U.S. Provisional Application 62/949,869, filed Dec. 18, 2019. Each of these applications are hereby incorporated by reference in their entireties.

STATEMENT REGARDING FEDERALLY SPONSORED RESEARCH OR DEVELOPMENT

This invention was made with government support under GM117058 awarded by the National Institutes of Health. The government has certain rights in the invention.

REFERENCE TO AN ELECTRONIC SEQUENCE LISTING

The contents of the electronic sequence listing (136-19US_Replacement sequence_listing_ST25.txt; Size: 6,581 bytes; and Date of Creation: Oct. 17, 2025) is herein incorporated by reference in its entirety.

BACKGROUND OF THE INVENTION

Cardiovascular diseases account for approximately one out of every four deaths in the United States, with an estimated healthcare burden of over $200 billion per year. Early and accurate diagnosis of heart failure enables successful patient outcomes and reduces the need for excessive and costly testing. Cardiac troponin I (cTnI) is clinically recognized as a sensitive and specific protein biomarker for acute coronary syndrome because it has an amino acid sequence specific to cardiac tissue and is released into the bloodstream following cardiac injury (Missov et al., 1997, Circulation, 96:2953-2958). Additionally, increased circulating cTnI concentration is correlated to the onset of cardiac damage (Thygesen et al., 2018, Journal of the American College of Cardiology, 25285; Westermann et al., 2017, Nature Reviews Cardiology, 14: 472; and Antman et al., 1996, New England Journal of Medicine 335: 1342-1349).

For these reasons, cTnI is a gold-standard biomarker used in the clinical evaluation of myocardial injury. Circulating cTnI in the blood exists in low abundance and in myriad proteoforms (Smith et al., 2013, Nature Methods, 10:186) (e.g., phosphorylated, truncated, acetylated, and/or oxidized forms of the protein) that are known to reflect pathophysiological processes (Bates et al., 2010, Clinical Chemistry, 56:952; Madsen Lene et al., 2006, Circulation Research, 99:1141-1147; and Soetkamp et al., 2017, Expert Review of Proteomics 14: 973-986). Although high-sensitivity immunoassays can detect elevated troponin levels, because antibodies have batch-to-batch variations and target different epitopes, these assays often yield inconsistent results and contribute to false observations of elevated cTnI levels in non-acute myocardial infarction patients (Herman et al., 2017, American Journal of Clinical Pathology, 148 (4): 281-295; and Hyytia et al., 2015, Clinical Biochemistry, 48(4): 313-317). Current patient risk-stratification and heterophile antibodies also lead to high false positive rates and increased costs (Zaidi et al., 2010, BMJ Case Rep., 2010: bcr1120092477).

Importantly, in reviewing troponin testing (qualitative point-of-care and quantitative cTnI measurements) at 14 hospitals, only 3.5% of 92,445 elevated troponin values (>0.09 ng/ml) were associated with acute myocardial infarction (AMI) diagnosis. While current cTnI assays have high negative predictive value (>99%) leading to few cases of "false-negative" AMI diagnosis, the positive predictive value (28.8%) is low (Wilson et al., 2017, J. Hosp Med, 5: 329-331). The continued use of current cTnI antibody-based immunoassays for AMI leads to increased cardiology consultation and medical testing, contributing significantly to the $200 billion spent in cardiovascular related healthcare costs per year.

Moreover, because cTnI typically exists as a myriad of proteoforms in low-abundance which arise from genetic variations, alternative splicing, and post-translational modifications (PTMs) for a single gene product, the unambiguous identification and characterization of cTnI proteoforms remains a significant challenge for the antibody-based approach. However, proteoform-resolved information is essential to accurate diagnosis of AMI. Furthermore, because dysregulation of cTnI proteoforms occurs in AMI and other cardiomyopathies, an assay that unambiguously characterizes cTnI proteoforms in blood is essential for accurate diagnosis of AMI (Soetkamp et al., 2017, Review of Proteomics 14: 973-986), and also for risk stratification, and outcome assessment for patients with acute coronary syndrome (ACS) and non-ACS myocardial injury. Accordingly, there is an urgent need to develop an accurate and comprehensive assay that combines cTnI enrichment from blood with sensitive mass spectrometry (MS)-based validation to detect and comprehensively characterize all proteoforms of cTnI.

Top-down MS-based proteomics, which analyzes intact proteins, is arguably the most powerful method to comprehensively and accurately characterize proteoforms, including those of cTnI (Chen et al., 2018, Analytical Chemistry 90(1): 110-127; Siuti et al., 2007, Nature Methods 4: 817-821; and Kelleher et al., 2014, Expert Review of Proteomics 11(6): 649-651). However, MS-based proteomics is limited by the large dynamic range and the complexity of the human blood proteome, and often requires additional front-end enrichment strategies (Anderson et al., 2002, History, Character, and Diagnostic 1(11): 845-867). Because cTnI is present at low concentrations in human serum, proteomics analysis without prior enrichment of cTnI would only result in the detection of the most abundant blood proteins. Thus, the development of front-end MS-compatible strategies that can enrich cTnI prior to MS-analysis is critical.

SUMMARY OF THE INVENTION

The present invention provides mass spectrometry (MS) compatible nanomaterials for the selective capture and enrichment of biomolecules, preferably proteins, including, but not limited to, cardiac proteins. Nanoparticles are functionalized with probe molecules that can specifically bind to a desired biomolecule (or a desired class of biomolecule) and allow for accurate MS-analysis and characterization of the biomolecule(s). In the case where the desired biomolecules are proteins, this analysis and characterization can include top-down MS-based proteomic analysis of intact, unfragmented or undigested proteins as well analysis of different proteoforms of the proteins.

In an embodiment, the present invention provides a composition comprising a nanoparticle and one or more probe molecules attached to the nanoparticle, wherein the one or more probe molecules are able to preferentially bind to a selected biomolecule (or a class of biomolecules). The nanoparticle is preferably a superparamagnetic nanoparticle, including but not limited to nanoparticles comprising magnetic ferrites. In an embodiment, the nanoparticle comprises $Fe_3O_4$, $Fe_2O_4$, $CoFe_2O_4$, $ZnFe_2O_4$, $NiFe_2O_4$, $MnFe_2O_4$, and combinations thereof. In an embodiment, the nanoparticle comprises iron oxide ($Fe_3O_4$) or cobalt ferrite ($CoFe_2O_4$). In an embodiment, nanoparticle comprises iron oxide ($Fe_3O_4$).

Preferably, the surface of the nanoparticle is functionalized with one or more organosilane coupling molecules, and the one or more probe molecules are attached to the nanoparticle through the one or more coupling molecules. In a further embodiment, the one or more coupling molecules comprise amine based organosilane coupling molecules, monomers, amine based organosilane monomers, and combinations thereof. In an embodiment, the one or more coupling molecules comprise N-(3(triethoxysilyl) propyl) buta-2,3-dienamide (BAPTES), N-(3(trimethoxysilyl) propyl)buta-2,3-dienamide (BAPTMS), N-(3(triethoxysilyl) propyl)-3-butynamide, N-(3(trimethoxysilyl) propyl)-3-butynamide, or combinations thereof.

In an embodiment of the present invention, the surface of a nanoparticles is functionalized with one or more probe molecules, including but not limited to polypeptides that can preferentially bind to a desired protein. These polypeptides can include antibodies and fragments of antibodies; however, the present invention is not limited to the use of antibodies to bind to the desired protein. Preferably, the nanoparticles are functionalized with probe molecules having a high affinity and selectivity for a desired protein, especially a desired proteoform. Useful proteoforms include, but are not limited to, phosphorylated proteoforms, unphosphorylated proteoforms, degraded proteoforms, glycosylated proteoforms, oxidized proteoforms, acetylated proteoforms, post-translational modified proteoforms, and combinations thereof.

In an embodiment, the nanoparticles are functionalized with probe molecules having a high affinity and selectivity for a cardiac protein, including but not limited to cardiac troponin I (cTnI) or cardiac troponin T (cTnT) within the human cardiac troponin complex, as well as proteoforms of cTnI and cTnT. Optionally, the nanoparticle utilizes the modular attachment of a cysteine (thiol)-terminated peptide with high affinity and selectivity for cTnI, allowing for the capture, enrichment, and MS-analysis and characterization of cTnI proteoforms from human heart tissue lysates and human blood and/or serum samples. This invention further provides a comprehensive and accurate cTnI assay for detection of cTnI from patient blood and/or serum samples. Such assays are useful for the accurate diagnosis of acute coronary syndrome (ACS) and chronic diseases, including but not limited to acute myocardial infarction (AMI). Such assays are also useful for risk stratification, and outcome assessment for patients with ACS and non-ACS myocardial injury.

In an embodiment, the surface of the nanoparticles is functionalized with polypeptides having a binding affinity ($K_d$) of at least 200 μM to the selected protein, preferably a binding affinity ($K_d$) of at least 270 μM to the selected protein. In an embodiment, the one or more polypeptides comprise an amino acid sequence having at least 75% sequence identity to HWQIAYNEHQWQ (SEQ ID NO: 1), preferably at least 80% sequence identity to HWQIAYNEHQWQ (SEQ ID NO: 1), preferably at least 90% sequence identity to HWQIAYNEHQWQ (SEQ ID NO: 1). In an embodiment, the one or more polypeptides comprise the amino acid sequence HWQIAYNEHQWQ (SEQ ID NO: 1). In an embodiment, the one or more polypeptides comprise an amino acid sequence having at least seven contiguous amino acids of SEQ ID NO: 1, preferably at least eight contiguous amino acids, preferably at least nine contiguous amino acids, preferably at least ten contiguous amino acids, and preferably at least eleven contiguous amino acids. Short (<20 amino acids) and medium sized polypeptides (between 20 and 100 amino acids) are pH and temperature stable, and are easier to specifically functionalize compared to typical antibodies. For example, addition of a cysteine-residue to the C-terminus of such a peptide (i.e., HWQIAYNEHQWQ-Cys-SEQ ID NO:2) allows for novel, chemoselective nanoparticle surface coupling chemistry. Optionally, the functionalization happens through allenic amide-based organosilane monomers that are highly specific and reactive towards thiol-containing molecules of peptides in the presence of other biologically relevant nucleophiles, such as hydroxyls, amines, and carboxylates.

In an embodiment, the surface of the nanoparticles is functionalized with a small molecule affinity reagent that is modified with a cysteine-thiol linker. Such small molecule affinity reagents include, but are not limited to, kinase inhibitors, GPCR agonists and GPCR antagonists for kinases or G-protein coupled receptors and ACE2 receptors. Preferably, the small molecule affinity reagent has a binding affinity ($K_d$) of at least 200 μM to the selected protein, or more preferably a binding affinity ($K_d$) of at least 270 μM to the selected protein.

As used herein, the nanoparticles have a diameter of 100 nm or less, preferably 40 nm or less, or 10 nm or less.

In an embodiment, the present invention provides a method of making a functionalized nanoparticle comprising a superparamagnetic nanoparticle and one or more probe molecules attached to the nanoparticle, where the method comprising the steps of: a) silanizing at least a portion of a surface a superparamagnetic nanoparticle with one or more amine-based organosilane monomers, wherein said one or more monomers comprise a functional group having high chemoselectivity towards thiol-containing molecules; and b) reacting the silanized nanoparticle with a probe molecule or probe molecule precursor having a cysteine amino acid residue or a terminal thiol functional group. The probe molecule or probe molecule precursor is optionally a polypeptide having a terminal cysteine residue, and the functional group is optionally an allene functional group. In an embodiment, the one or more monomers preferably comprise N-(3(triethoxysilyl)propyl)buta-2,3-dienamide (BAPTES) and the probe molecule precursor comprises the amino sequence HWQIAYNEHQWQ-Cys (SEQ ID NO:2).

In an embodiment, the present invention provides a method for analyzing a cardiac protein in a sample, said method comprising the steps of:

a) adding functionalized nanoparticles to the sample containing the cardiac protein, wherein the functionalized nanoparticles comprise a superparamagnetic nanoparticle and one or more probe molecules attached to the superparamagnetic nanoparticle, wherein the one or more probe molecules are able to preferentially bind to the cardiac protein, thereby generating protein bound nanoparticles;
b) magnetically isolating the protein bound nanoparticles, thereby generating isolated nanoparticles;

c) eluting the cardiac protein from the isolated nanoparticles, thereby generating an enriched fraction of the cardiac protein able to be used for further chemical and/or biological analysis; and d) ionizing the enriched fraction of the cardiac protein and performing mass spectrometry (MS) analysis on the ionized cardiac protein.

The method optionally further comprises purifying the enriched fraction prior the MS analysis, such as by method including, but not limited to, various modes of liquid chromatography (LC) methods.

Preferably, the one or more probe molecules are able to preferentially bind to a cardiac protein having a molecular weight of 80 kDa or less, preferably 60 kDa or less, or 30 kDa or less, including but not limited to cardiac troponin I (cTnI) or cardiac troponin T (cTnT) as well as various proteoforms of cTnI and cTnT. The sample comprises blood, serum, plasma, tissue, or combinations thereof, taken from a subject (preferably a human subject).

In an embodiment, the sample is taken from a patient and a diagnosis of a cardiac disease (or cardiac diseases) is performed based on presence of the cardiac protein in the sample. The cardiac disease comprises ACS and non-ACS chronic diseases, including but not limited to AMI. Optionally, the cardiac protein is a selected proteoform of a cardiac protein, preferably a proteoform of cTnI, and the method comprises binding one or more proteoforms of the cardiac protein to the functionalized nanoparticles, magnetically isolating the protein bound nanoparticles, eluting the one or more proteoforms, and ionizing and performing MS analysis on the one or more proteoforms. The diagnosis of the cardiac disease is based on the relative amount of one proteoform to another proteoform from the sample, or to the amount of the proteoform compared to a control sample of a healthy population. Useful proteoforms for the diagnosis of cardiac diseases include, but are not limited to, phosphorylated proteoforms, unphosphorylated proteoforms, degraded proteoforms, glycosylated proteoforms, oxidized proteoforms, acetylated proteoforms, post-translational modified proteoforms, and combinations thereof.

In a further embodiment, the method further comprises taking a first sample from the patient at a first time period, taking one or more subsequent samples from the patient at one or more later time periods, and comparing the relative amounts of the one or more proteoforms from the first sample and the one or more subsequent samples.

Roman numerals correspond to N-terminally acetylated cTnI proteoforms following Met exclusion: (i) ppcTnI[1-207]; (ii) cTnI; (iii) pcTnI; (iv) ppcTnI; (v) cTnI[1-205]; (vi) pcTnI[1-205]; (vii) cTnI[1-206]; (viii) pcTnI[1-206]. cTnI proteoforms were identified using accurate intact mass measurement, using the most abundant mass based on the amino acid sequence of entry name TNNI3_human from the UniProtKB sequence database. M., protein marker; Std., endogenous cTnI protein standard. p., phosphorylation. pp., bisphosphorylation. A summary of the enriched proteoforms and their respective mass measurements by top-down MS are listed in Tables 3 and 4.

Figure 7:
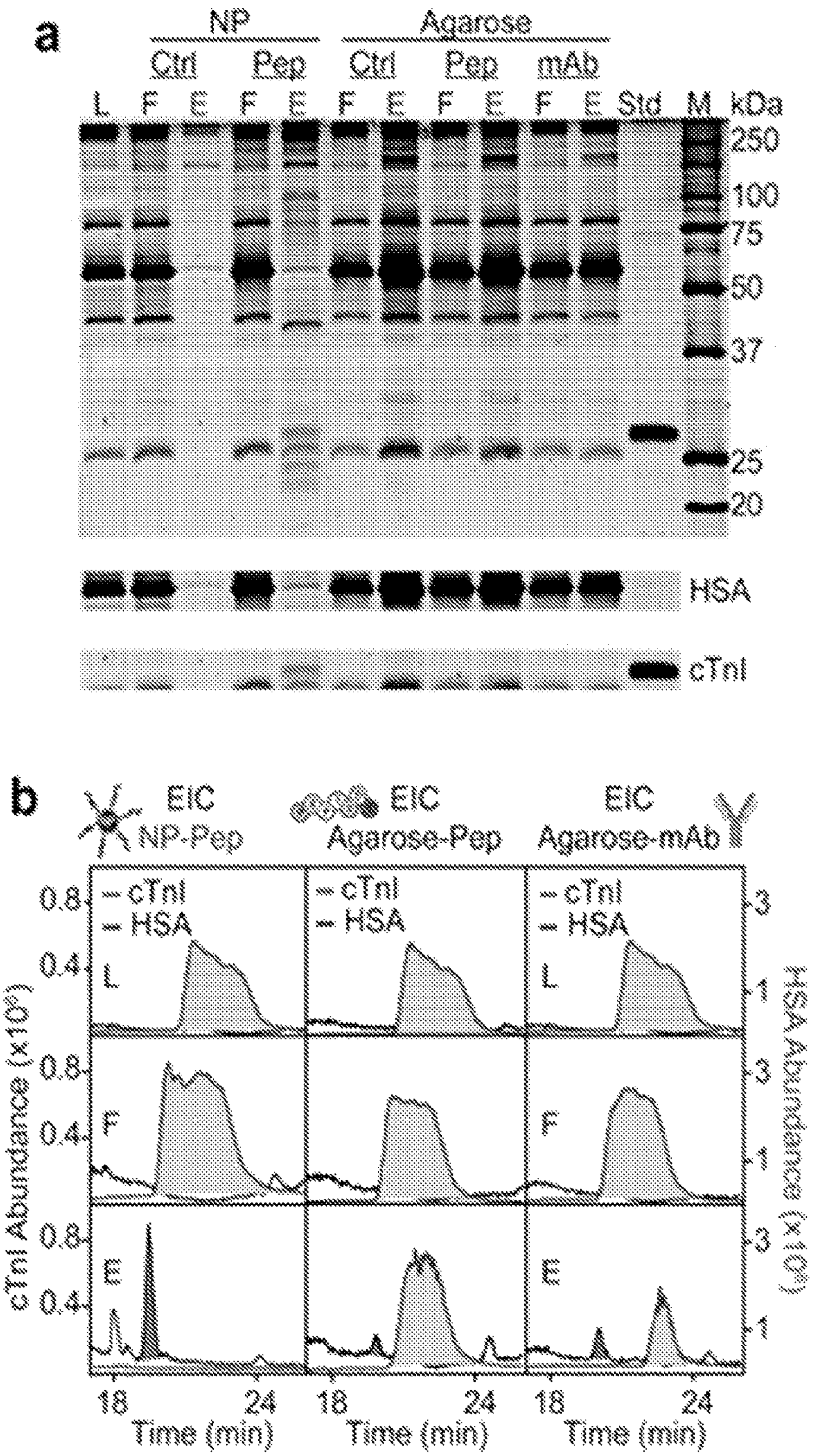

FIG. 7—Human serum with spike-in cTnI was used for the evaluation of cTnI enrichment performance using NP-Pep and the conventional agarose-mAb. a, SDS-PAGE visualizing the effectiveness of cTnI enrichment from human serum using different affinity platforms. The cTnI (306 ng) was obtained from a sarcomeric protein extract from a healthy donor heart and spiked into human serum (10 mg). Loading mixture (L), flow through (F), and elution mixture after enrichment (E) were equally loaded on the gel (500 ng) using NP-Ctrl, NP-Pep, Agarose-Ctrl, Agarose-Pep, and Agarose-mAb. The NP-Pep enabled nearly complete depletion of human serum albumin (HSA), allowing for more specific enrichment of cTnI from highly complex human serum. b, Normalized extracted ion chromatograms (EICs) of cTnI and HSA corresponding to the NP-Pep, Agarose-Pep, and Agarose-mAb shown in (a).

Figure 8:
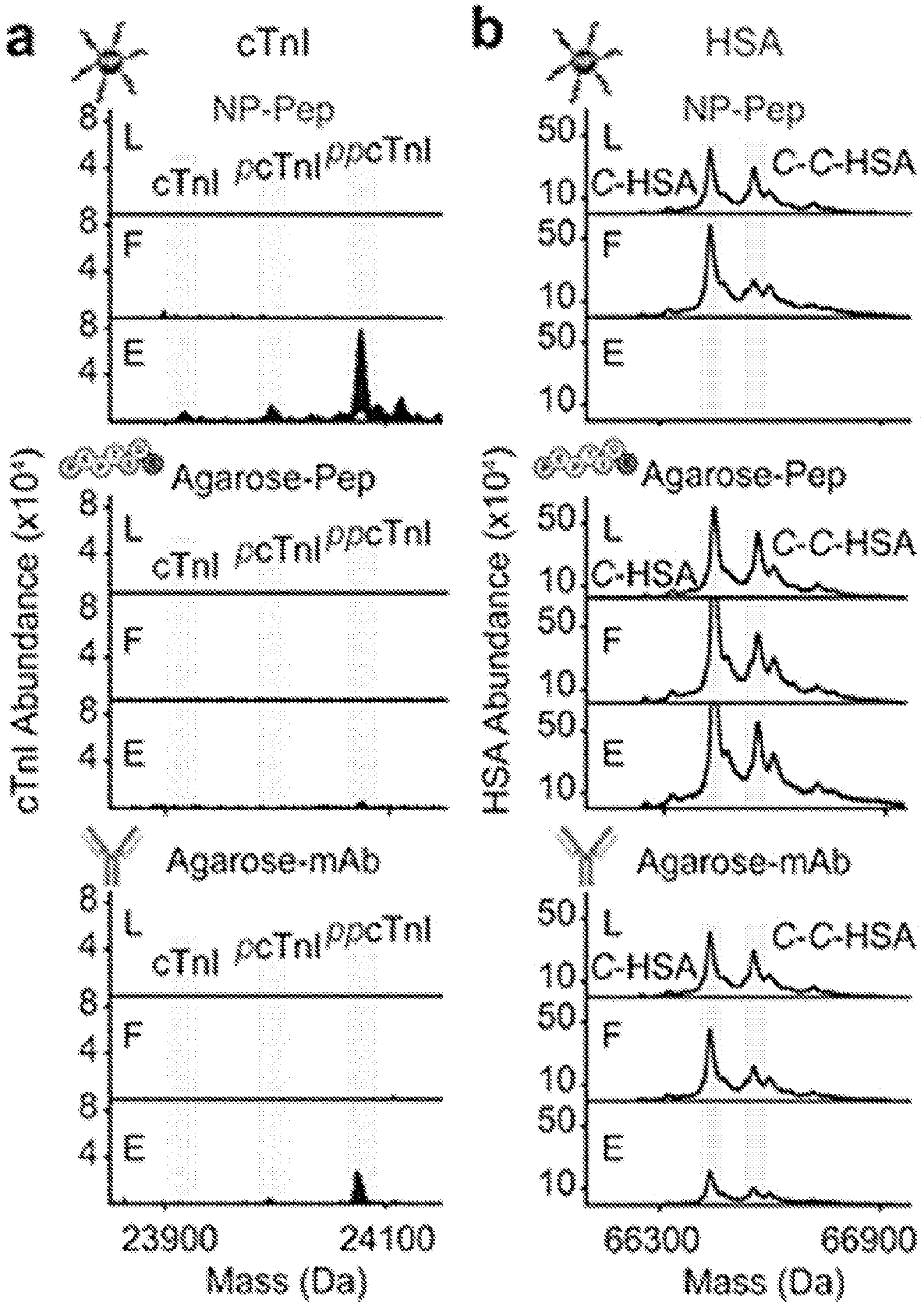

FIG. 8—Normalized deconvoluted mass spectra corresponding to enriched cTnI (a) and depleted HSA (b), illustrating the abundance of cTnI and HSA before and after enrichment using NP-Pep, Agarose-Pep, and Agarose-mAb corresponding to (FIG. 7).

Figure 9:
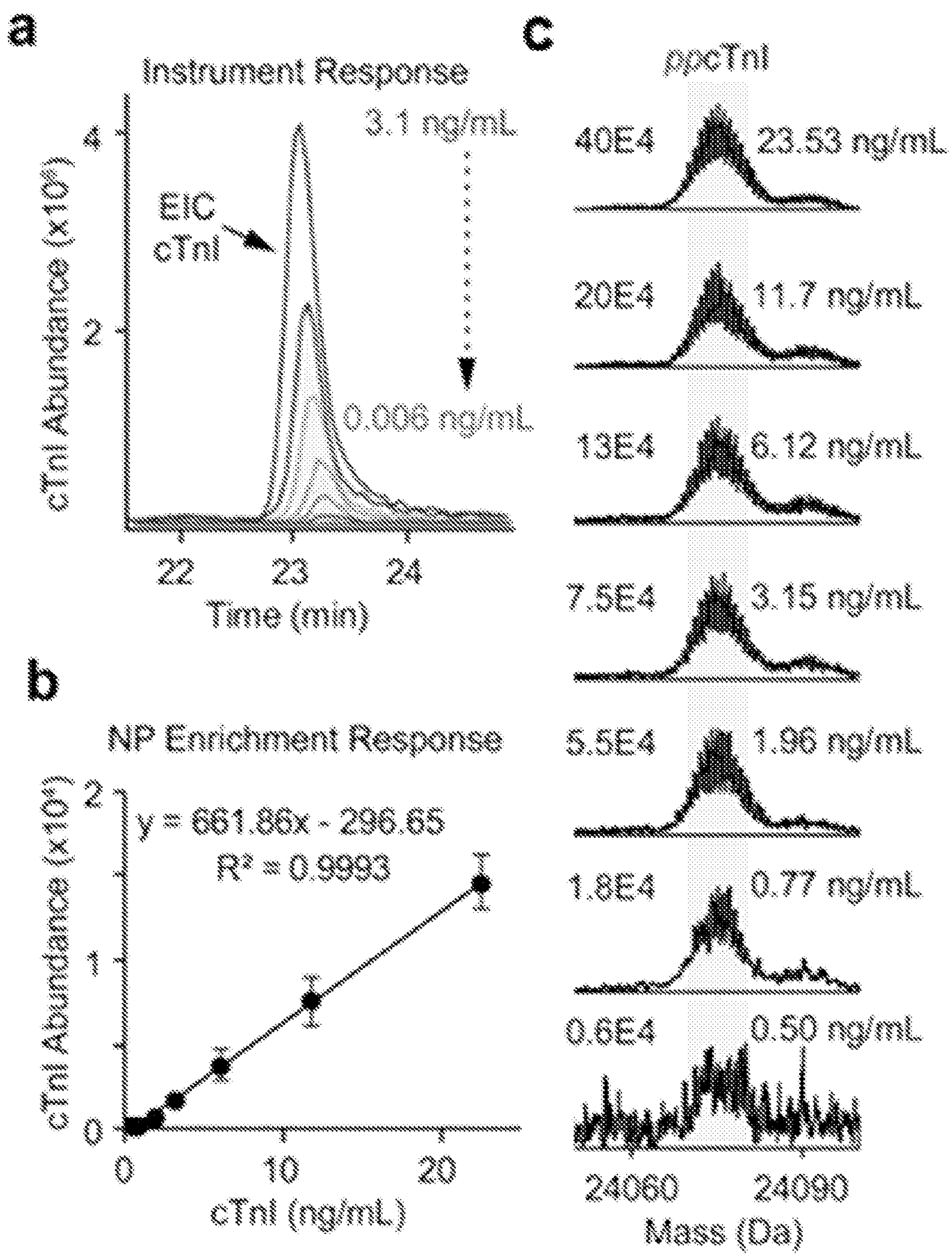

FIG. 9-*a*, Normalized EICs illustrating the MS response for cTnI (3.1 ng/ml to 0.006 ng/ml) obtained from a human heart tissue extract (n=2 independent experiments) using a Bruker maXis II ETD. b, Evaluation of the sensitivity performance of the nanoproteomics assay. MS response against cTnI concentration is shown for various NP-Pep enrichment fractions from serum mixtures spiked with cTnI (22.53-0.50 ng/mL). The deconvoluted peak intensities of ppcTnI were used for the analyses. Data are representative of n=3 independent experiments with error bars indicating standard error of the mean. c, Representative deconvoluted mass spectra illustrating the MS response for ppcTnI corresponding to the plot in (b). M., protein marker; Std., endogenous cTnI protein standard. p., phosphorylation. pp, bisphosphorylation. HSA, human serum albumin. C-HSA, cysteinylated human serum albumin. C-C-HSA, doubly cysteinylated human serum albumin. NP-Ctrl, unfunctionalized NP; NP-Pep, high affinity peptide-functionalized NP, Agarose-Ctrl, unfunctionalized agarose; Agarose-Pep, high affinity peptide-functionalized agarose; Agarose-mAb), antibody (mAb M46) functionalized with agarose.

Figure 10:
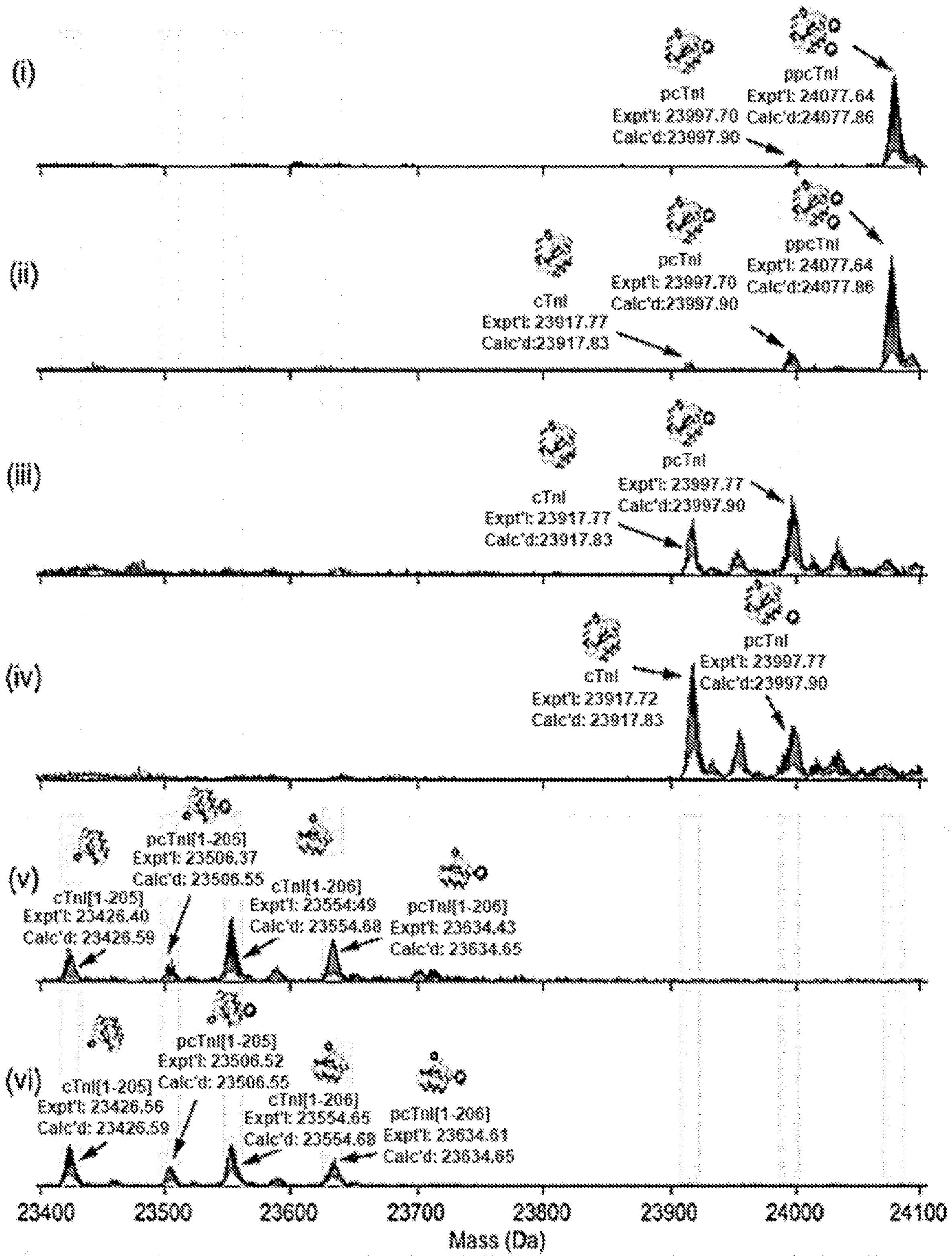

FIG. 10—Deconvoluted MS corresponding to cTnI proteoforms enriched from human serum. The cTnI (~10-20 ng/ml) spiked in the human serum (10 mg) are extracted from various human hearts: (i) and (ii), donor hearts; (iii) and (iv), diseased hearts with dilated cardiomyopathy, (v) and (vi), post-mortem hearts. cTnI proteoforms were identified using accurate intact mass measurement, using the most abundant mass based on the amino acid sequence of entry name TNNI3_human from the UniProtKB sequence database. p., phosphorylation. pp., bisphosphorylation. Data are representative of n=3 independent experiments. A summary of the enriched proteoforms from serum and their respective mass measurements by top-down MS are listed in Table 5.

Figure 11:
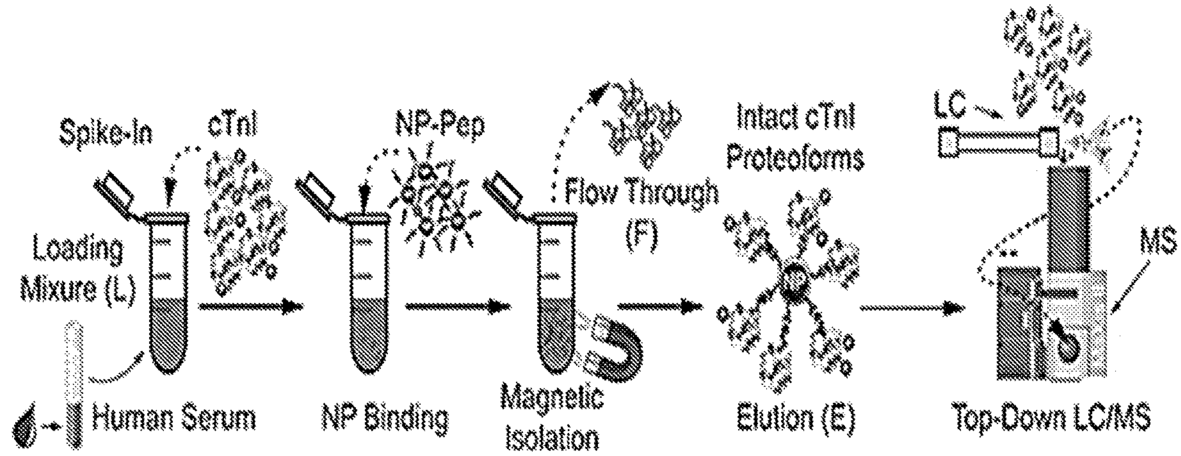

FIG. 11—Nanoproteomics assay utilizing NP-Pep for specific enrichment of cTnI from serum and subsequent top-down MS analysis of cTnI proteoforms. cTnI is first spiked into human serum to prepare the loading mixture (L). The NPs are then incubated with the serum loading mixture, the cTnI-bound NPs are magnetically isolated, the unwanted and nonspecific proteins are removed as flow-through (F). The captured cTnI is then eluted and the final elution fraction after enrichment is analyzed by top-down MS.

Figure 12:
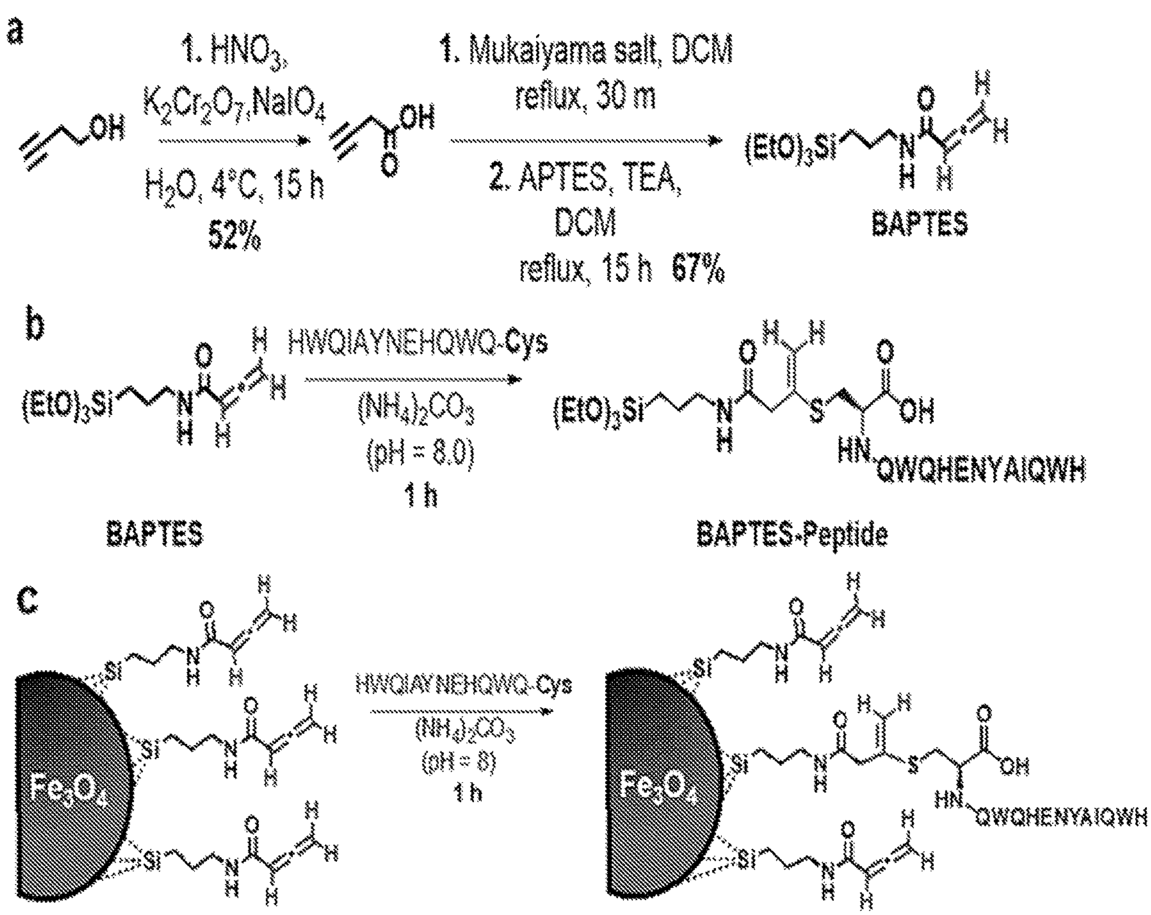

FIG. 12—Synthesis of N-(3-(triethoxysilyl)propyl)buta-2,3-dienamide (BAPTES) organosilane monomer and peptide modification with BAPTES. a, Scheme illustrating the facile synthesis of the BAPTES organosilane monomer used to silanize superparamagnetic 8 nm $Fe_3O_4$ NPs. ESI-MS for $C_{13}H_{25}NO_4Si$ $[M+H]^+$ observed: 288.16 m/z, $[M+H]^+$ calculated: 288.16 m/z. b, Cysteine modification of the high affinity cTnI-binding peptide (SEQ ID NO:1) with BAPTES monomer, illustrating potential functionalization of BAPTES surface-silanized NPs with cTnI-binding peptide. Yields are reported as the average of three independent synthesis experiments, c, Ligand exchange and subsequent peptide coupling on NP can be performed using allene functional group attached to additional Cys on the cTnI peptide (SEQ ID NO:1).

Figure 13:
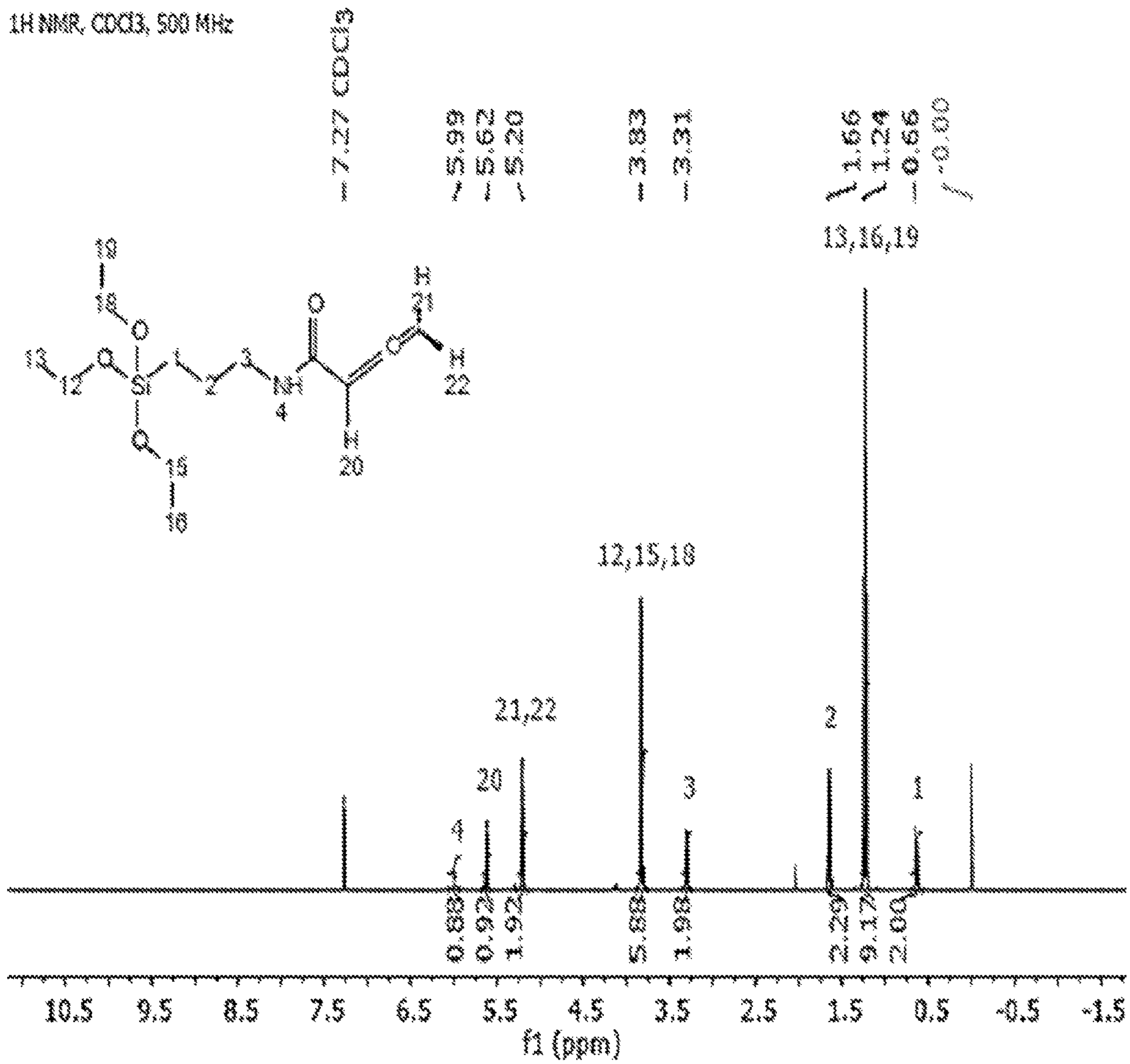

FIGS. 13-1H NMR of BAPTES monomer. $^1H$ NMR (500 MHz, Chloroform-d) δ (ppm) 5.99 (s, 1H), 5.62 (t, J=6.6 Hz, 1H), 5.20 (d, J=6.7 Hz, 2H), 3.83 (q, J=7.0 Hz, 6H), 3.31 (q, J=6.7 Hz, 2H), 1.66 (m, 2H), 1.24 (t, J=7.0 Hz, 9H), 0.66 (m, 2H). $^1H$ integrations confirm isolation and synthesis of BAPTES monomer.

Figure 14:
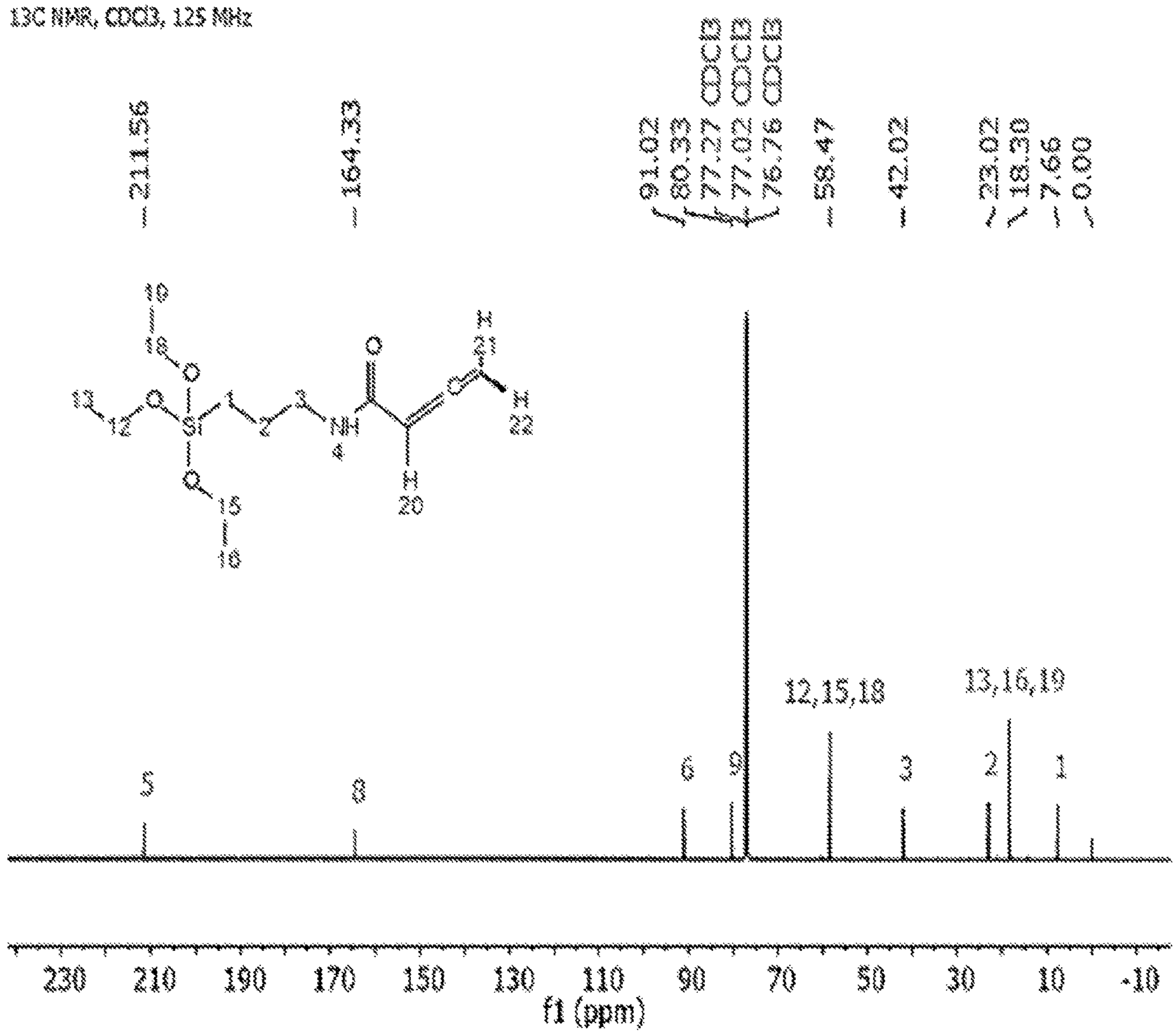

FIGS. 14—$^{13}C$ NMR of BAPTES monomer. 13C NMR (125 MHz, Chloroform-d) 0 (ppm) 211.56, 164.33, 91.02, 80.33, 58.47, 42.02, 23.02, 18.30, 7.66. $^{13}C$ NMR confirms the synthesis of the BAPTES monomer and the presence of 9 unique $^{13}C$ chemical environments.

Figure 15:
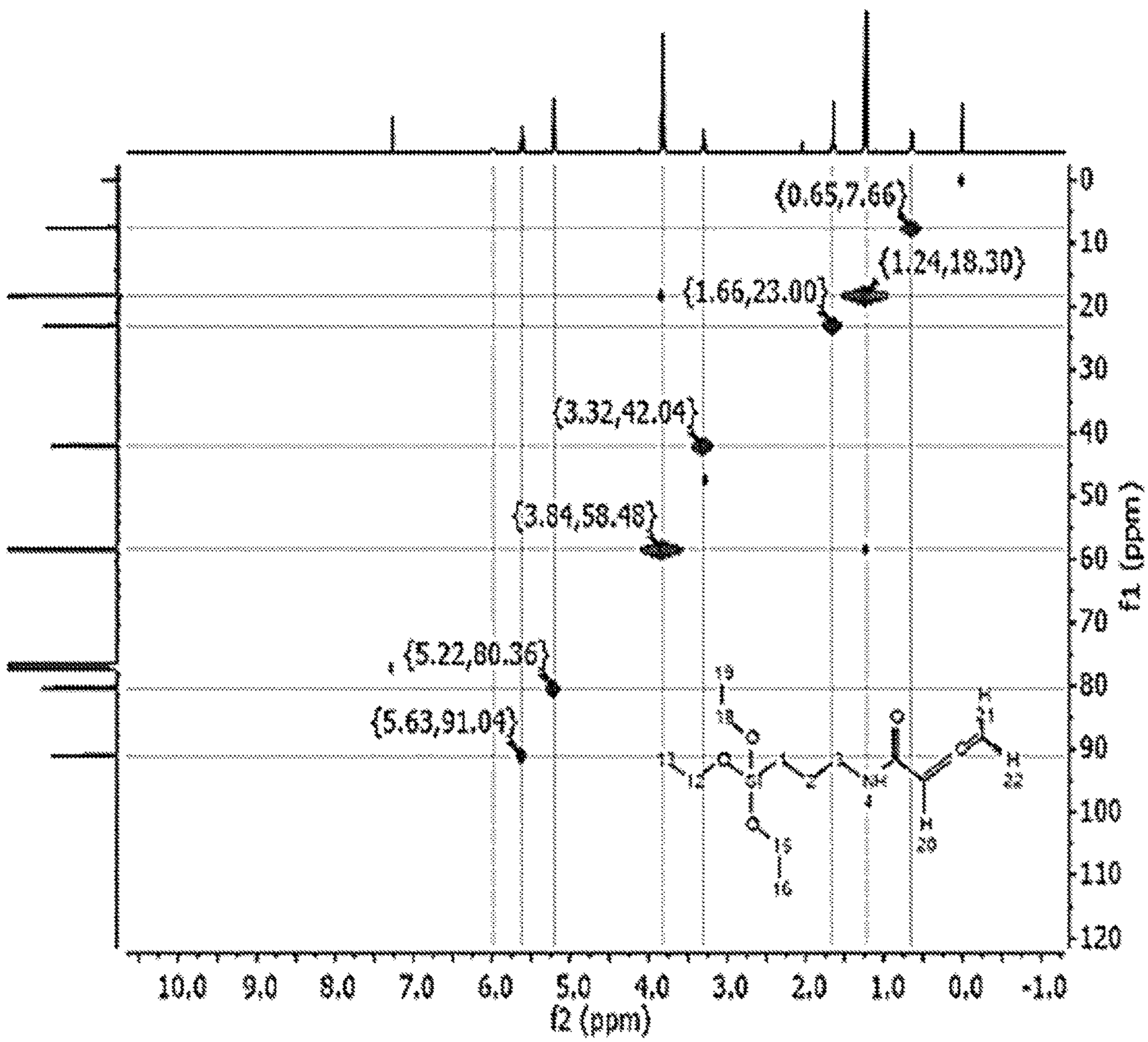

FIGS. 15—$^1H$-$^{13}C$ Heteronuclear Single Quantum Coherence (HSQC) NMR of BAPTES monomer. $^1H$-$^{13}C$ HSQC (500 MHz, Chloroform-d) correlates the observed $^1H$ and $^{13}C$ signals present in the BAPTES molecule, confirming purification and synthesis of BAPTES monomer.

Figure 16:
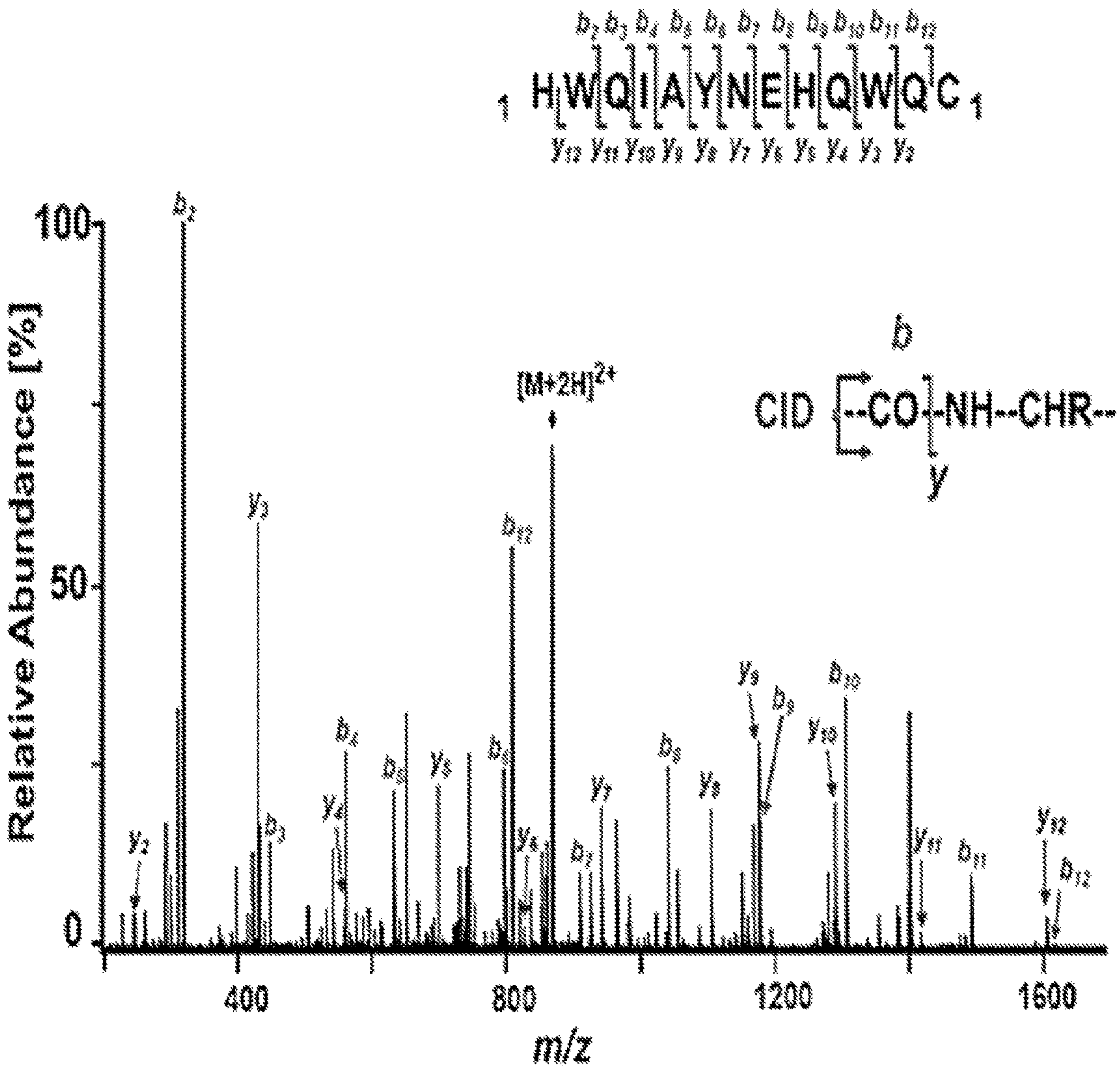

FIG. 16—ESI-MS of cTnI affinity peptide (SEQ ID NO: 2) showing full sequence coverage. The sequence of the cTnI affinity peptide is validated by tandem MS (MS/MS) with full sequence coverage, using a 12 T Bruker Fourier transform ion cyclotron resonance (FTICR) mass spectrometer. A mass accuracy cut-off of 10 ppm was used for MS/MS fragment ion assignments. All ion identifications were manually validated. ESI-MS for $C_{79}H_{103}N_{23}O_{21}S_1$ $[M+2H]^{2+}$ observed: 871.884 m/z, $[M+2H]^{2+}$ calculated: 871.878 m/z.

Figure 17:
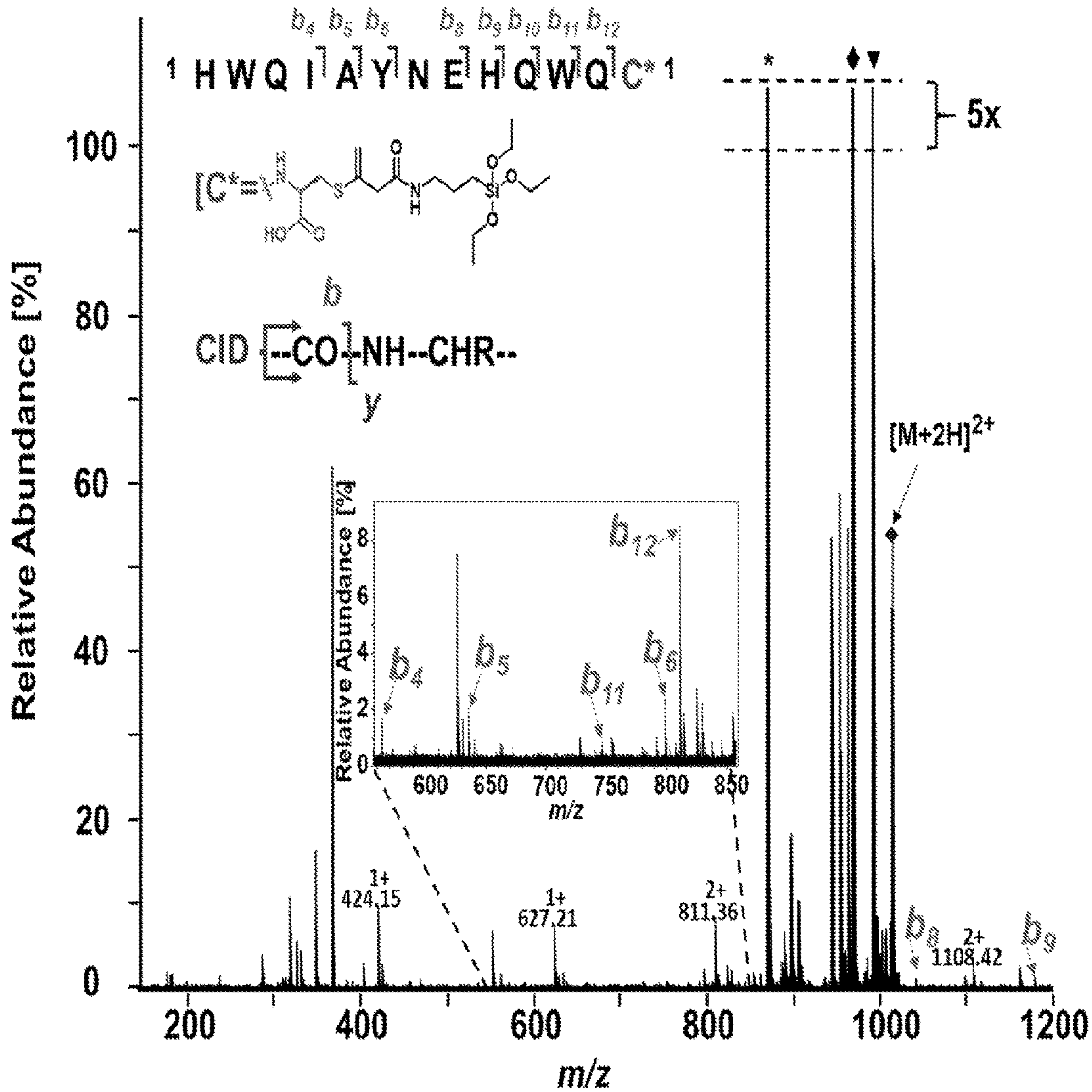

FIG. 17—ESI-MS of cTnI affinity peptide (SEQ ID NO: 2) coupled to BAPTES monomer showing site-specific addition of the peptide to the allenecarboxamide functional handle. The sequence of the BAPTES ($C_{13}H_{25}NO_4Si$)-modified cTnI affinity peptide is validated by tandem MS (MS/MS) sequence coverage using a 12 T Bruker Fourier transform ion cyclotron resonance (FTICR) mass spectrometer. Representative ions are denoted in the spectrum, with the inset showing an expansion of the 550-850 m/z range. A mass accuracy cut-off of 10 ppm was used for MS/MS fragment ion assignments. All ion identifications were manually validated. ESI-MS for $C_{92}H_{128}N_{24}O_{25}SiS$: $[M+2H]^{2+}$ observed: 1015.451 m/z, $[M+2H]^{2+}$ calculated: 1015.455 m/z. Neutral mass losses are denoted on spectra: ▼$[M+2H-C_2H_5OH]^{2+}$; ◇$[M+2H-2\ (C_2H_5OH)]^{2+}$; *$[M+2H-C_{13}H_{25}NO_4Si]^{2+}$.

Figure 18:
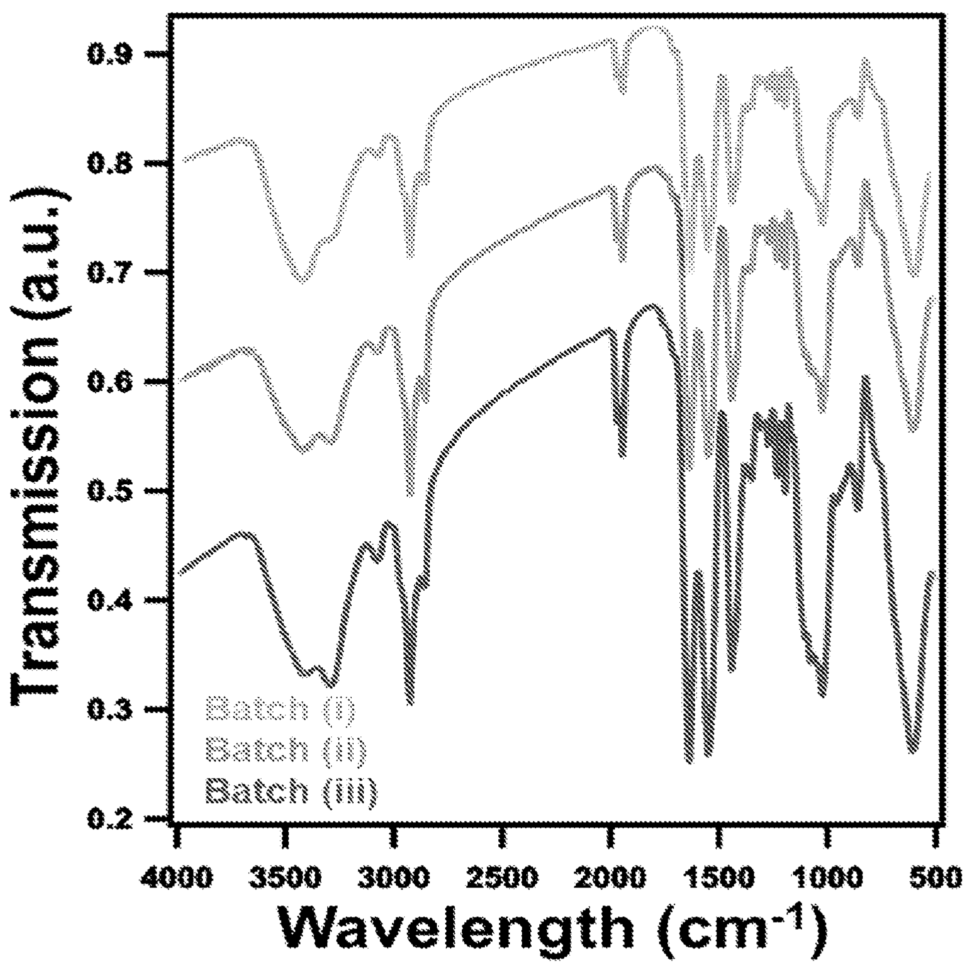

FIG. 18—Inter-batch reproducibility of surface functionalized NPs by Fourier transform infrared (FTIR) analysis. FTIR traces of three representative batches (i-iii) of $Fe_3O_4$-BAPTES NPs synthesized under the same reaction conditions. Traces are offset along the y-axis for clarity.

Figure 19:
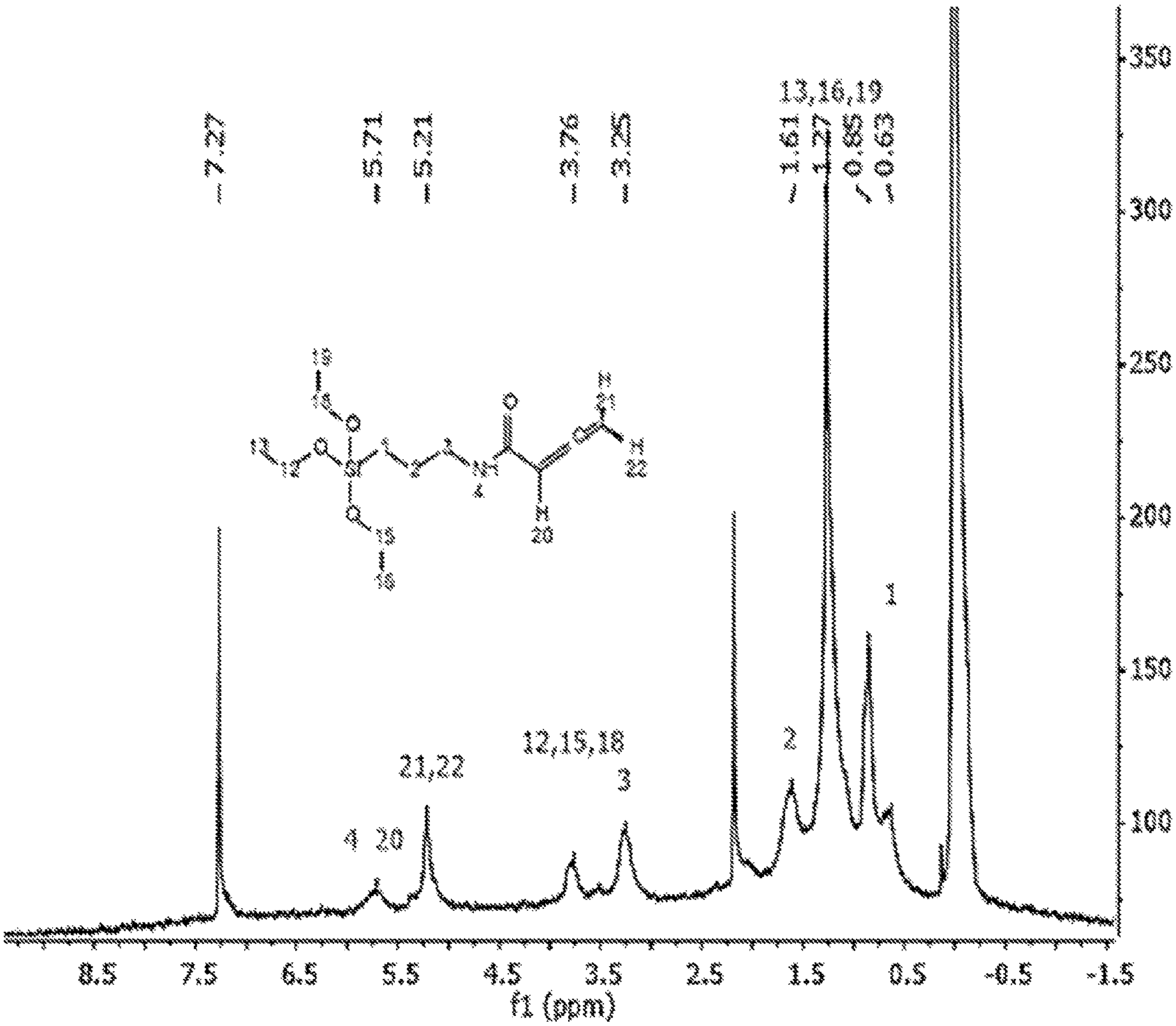

FIG. 19—High resolution magic angle spinning nuclear magnetic spectroscopy (HRMAS) analysis of silanized NPs. 1H NMR spectrum of $Fe_3O_4$-BAPTES NPs performed in Chloroform-d at a 9 kHz magic angle spinning (MAS) rate. 0 (ppm) 5.71, 5.21, 3.76, 3.25, 1.61, 1.27, 0.85, 0.63. Characteristic allenecarboxamide signatures belonging to the BAPTES monomer indicate the successful surface silanization of the starting $Fe_3O_4$-OA NPs to the $Fe_3O_4$-BAPTES NPs (i.e., unfunctionalized NPs, later referred to as NP-Ctrl).

Figure 20:
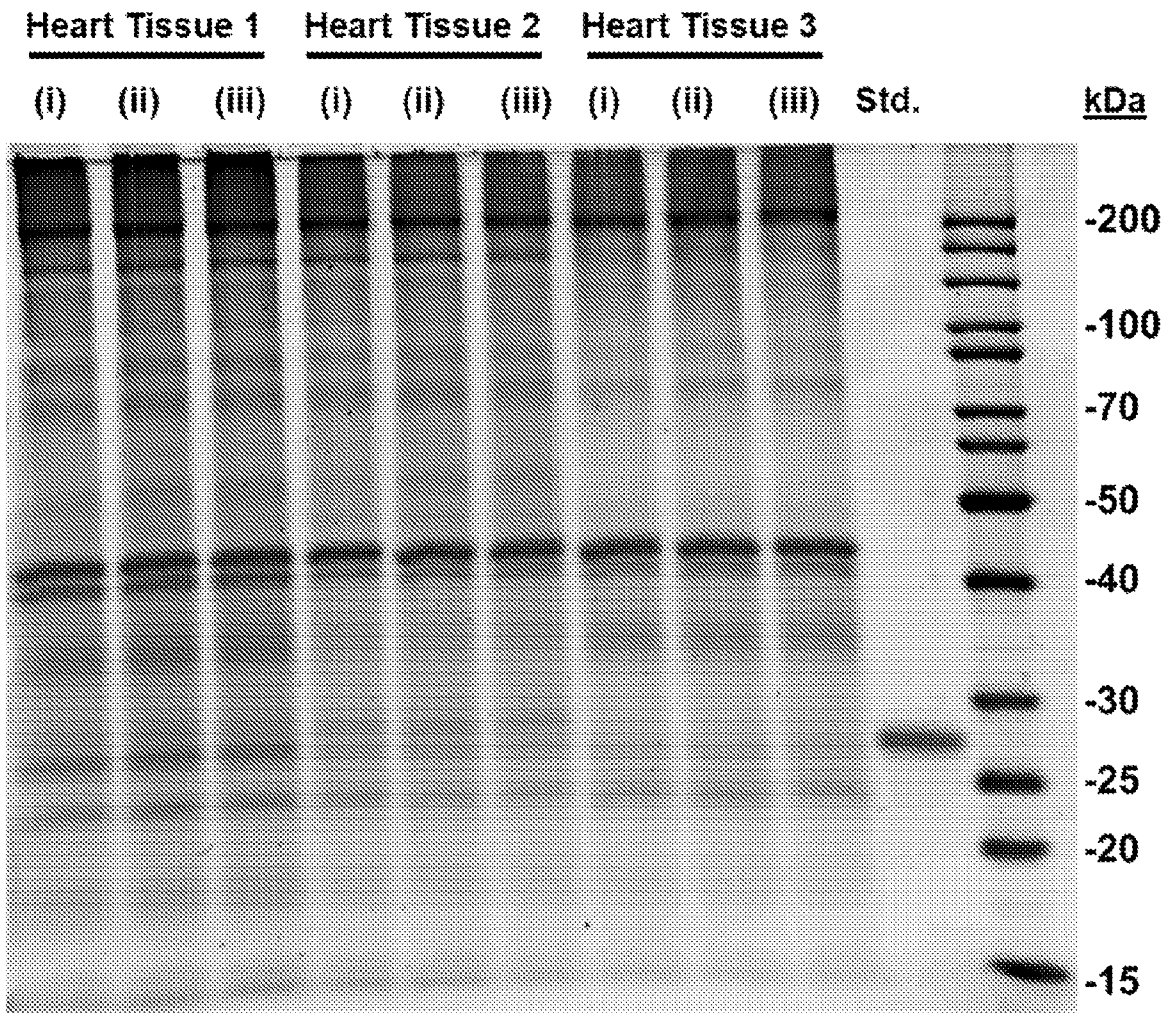

FIG. 20—Reproducibility of protein extractions from heart tissue. SDS-PAGE stained with SYPRO Ruby visualizing sarcomeric proteins obtained from the heart tissue protein extraction procedure. The heart tissue protein extraction procedure is listed in Table 2. Three independent protein extractions (i-iii) were performed on three different heart tissue samples (1, donor tissue; 2, ischemic tissue; 3, post-mortem tissue). Equal protein amount (1 μg) was loaded in each lane, demonstrating the reproducibility of protein extractions within three biological samples. Std., human cTnI protein standard.

Figure 21:
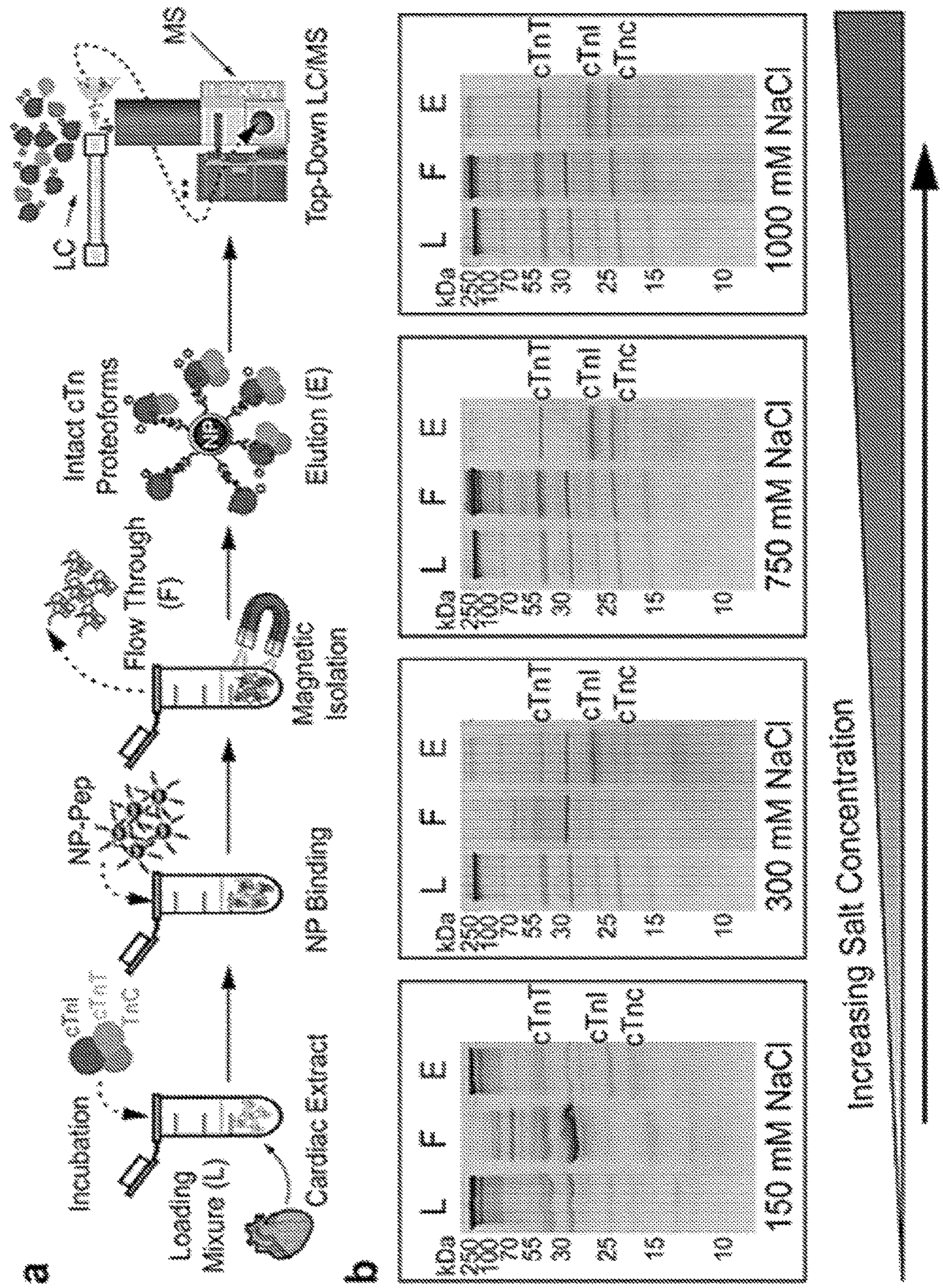

FIG. 21—Optimization of salt concentration in wash buffer for effective cTnI enrichment. a, Schematic illustration of the nanoproteomics strategy for enrichment of cTnI and its associating protein-protein interactors and top-down LC/MS analysis of proteins associated with cTnI. b, SDS-PAGE stained with Coomassie blue, visualizing that human cardiac sarcomere protein interacting partners of cTnI can be obtained during enrichment by simply tuning the salt concentration (150-750 mM NaCl) during the enrichment workflow. Equal amount (2 μg) of the loading mixture (L), flow-through (F), and elution mixture (E) after enrichment was loaded on the gel.

Figure 22:
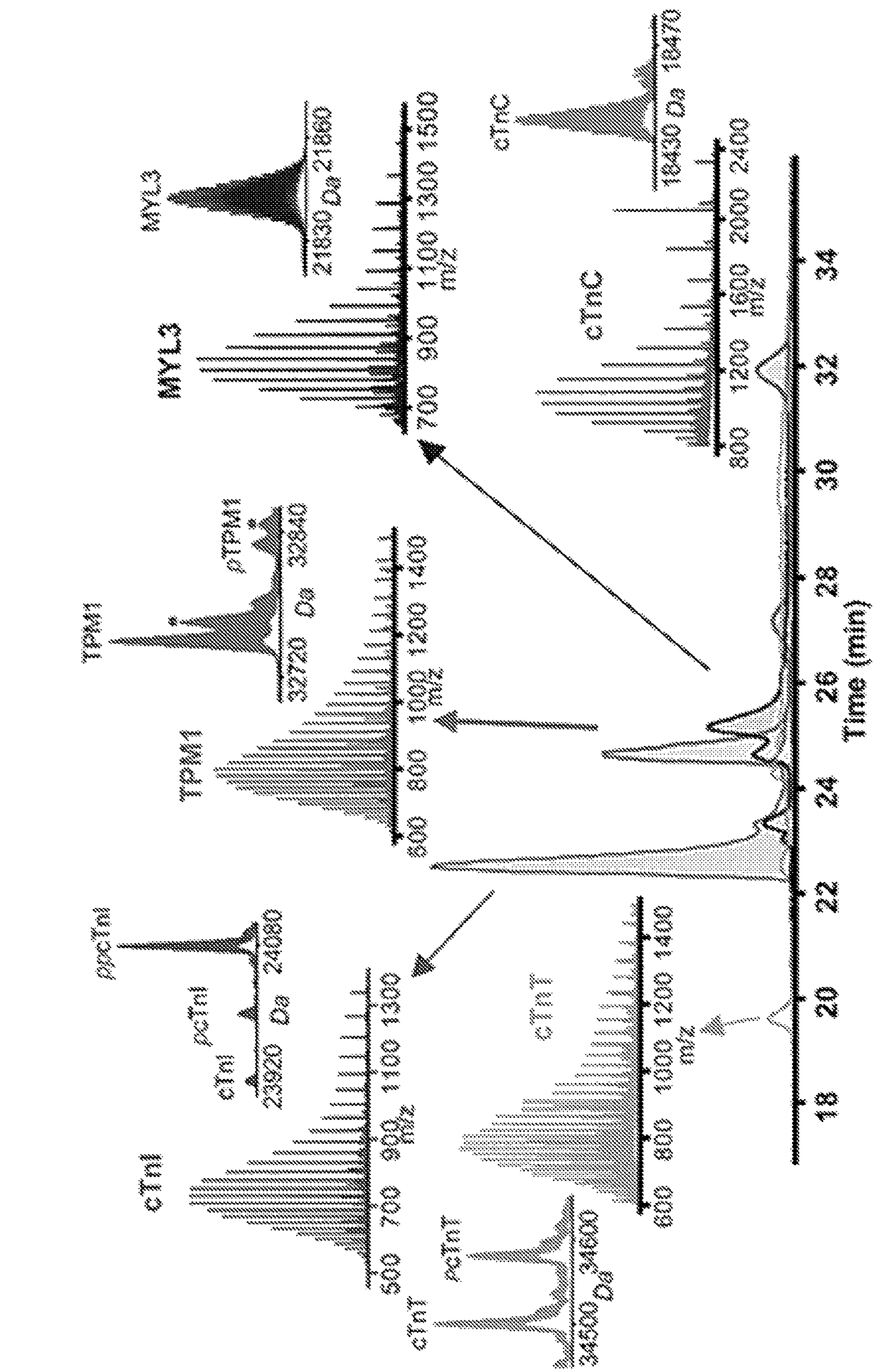

FIG. 22—Normalized extracted ion chromatograms and MS analysis of sarcomeric proteins obtained from the elution fraction after NP-Pep enrichment using 300 mM NaCl washing buffer. Deconvoluted MS for each protein is presented. 300 mM NaCl was ultimately used for all sarcomeric protein extract enrichment as it provided an optimal balanced between cTnI enrichment specificity and overall cTnI recovery. TMP1 (α-tropomyosin), and MYL3 (myosin light chain 3) are named from the UniProtKB sequence database. Squares indicate +16 Da proteoform. p., phosphorylation; pp., bisphosphorylation.

Figure 23:
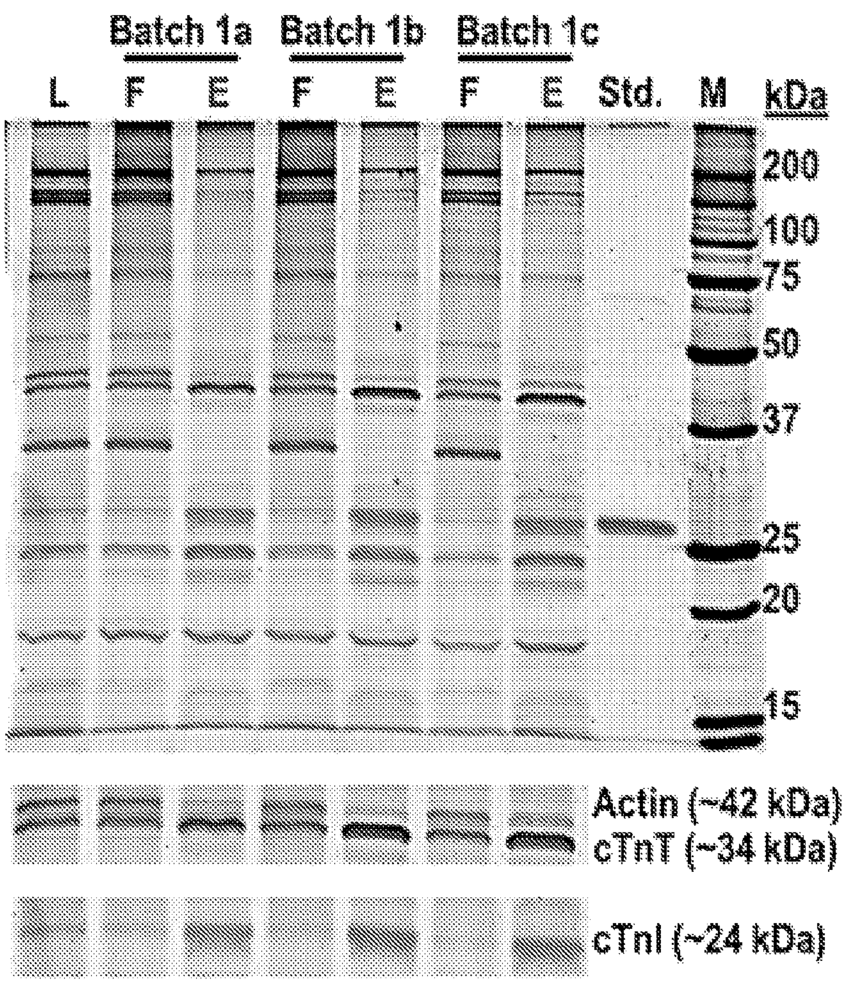

FIG. 23—SDS-PAGE stained with SYPRO Ruby visualizing the cTnI enrichment performance and demonstrating the high reproducibility obtained from the same synthesis batch of $Fe_3O_4$-BAPTES NPs (intra-batch). Equal amounts of NP-Pep (5 mg) from the same synthesis batch were used for cTnI enrichment from sarcomeric protein extracts (300 μg) containing 0.3% cTnI obtained from a human donor heart. Equal protein amount (500 ng) of the loading mixture (L), flow-through (F), and elution mixture after enrichment (E) was loaded on the gel. Lower panels display enlarged SDS-PAGE strips highlighting NP enrichment of cTnI (~24 kDa) and cTnT (~34 kDa) from the sarcomeric protein loading mixture.

Figure 24:
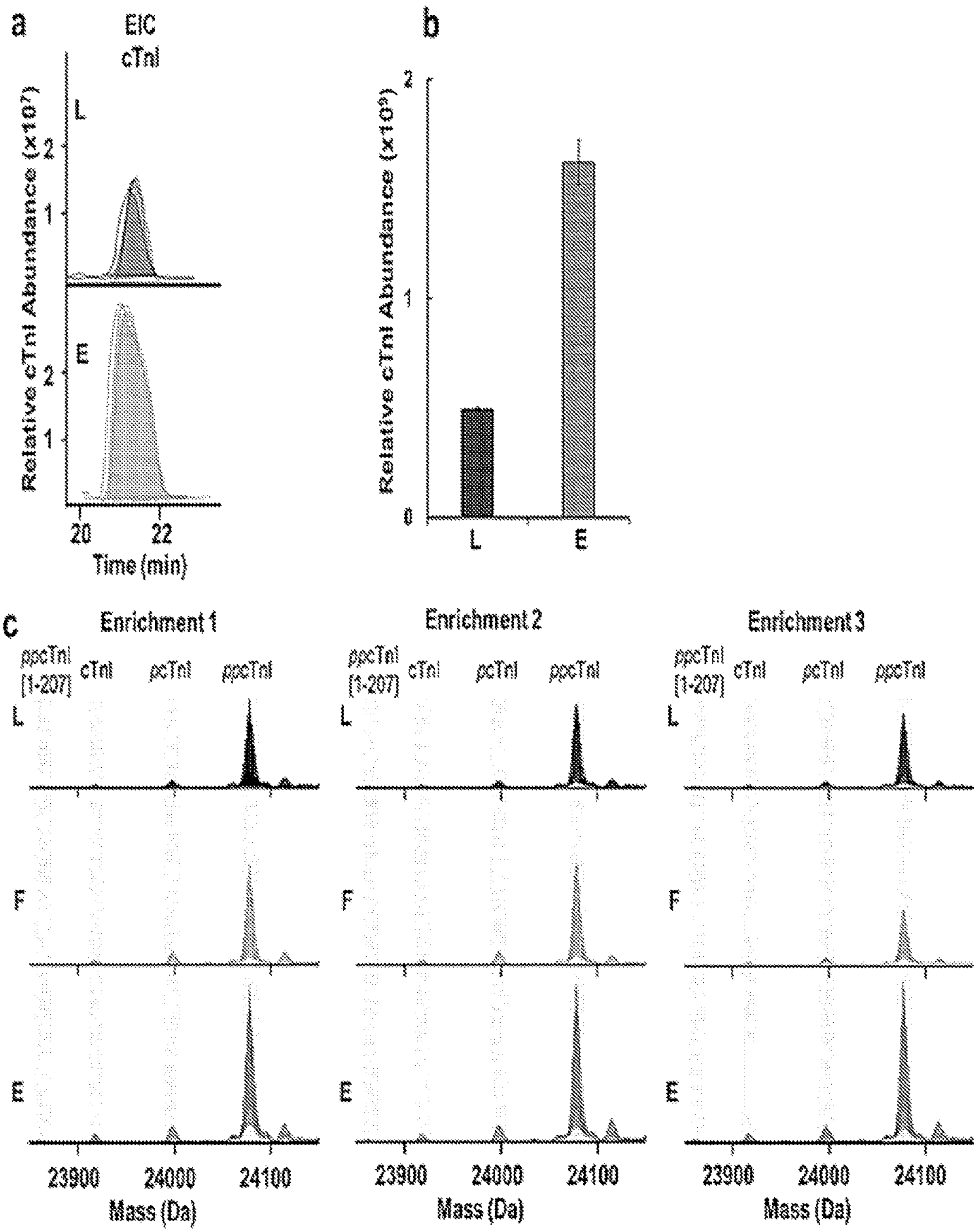

FIG. 24-*a*, Normalized extracted ion chromatograms (EIC) of cTnI from the sarcomeric protein loading mixture (L) and elution mixture (E). b, Relative abundance of cTnI from L and E when normalizing for 500 ng total protein loading, demonstrating significant enrichment of cTnI in E. c, Normalized deconvoluted mass spectra of cTnI present in the L, F, and E solutions, demonstrating consistency of cTnI enrichment across three enrichment replicates performed using nanoparticles synthesized from a single batch (intra-batch). N-terminally acetylated cTnI proteoforms following Met exclusion were identified using accurate intact mass measurement, using the most abundant mass based on the amino acid sequence of entry name TNNI3_human from the UniProtKB sequence database. p., phosphorylation; pp., bisphosphorylation. Std., human cTnI protein standard; M., protein marker.

Figure 25:
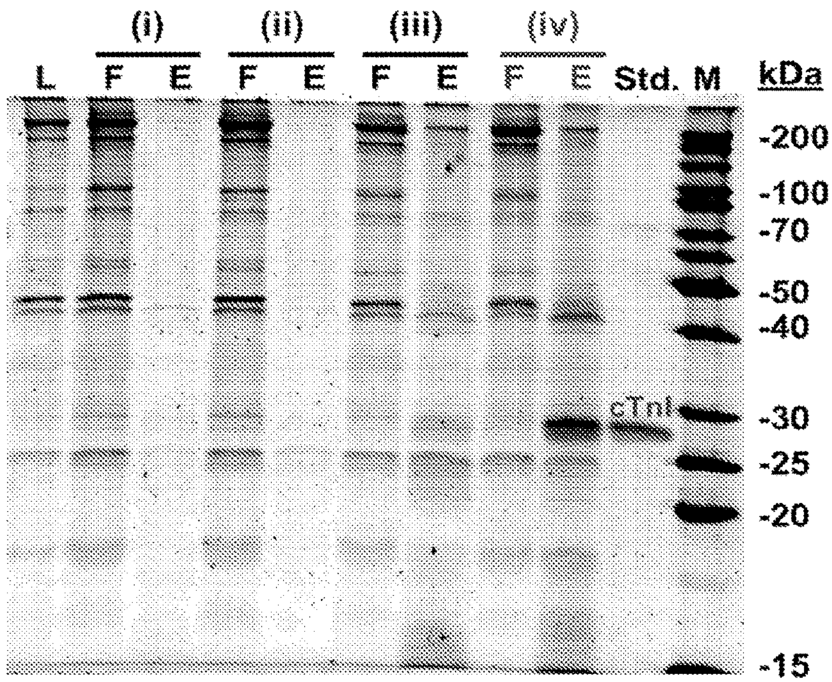

FIG. 25—SDS-PAGE stained with SYPRO Ruby was used to compare the cTnI enrichment performance of unfunctionalized $Fe_3O_4$-BAPTES NPs with no peptide coupled (NP-Control, i); $Fe_3O_4$-BAPTES NPs incubated with high affinity cTnI peptide (SEQ ID NO: 2) at pH 5.0 (NP, peptide pH 5.0, ii); $Fe_3O_4$-BAPTES NPs functionalized with a cTnI-negative control peptide (SEQ ID NO: 3) at pH 8.0 (Neg-Pep, iii); and the $Fe_3O_4$-BAPTES NPs functionalized with the high affinity cTnI peptide (SEQ ID NO: 2), pH 8.0 (NP-Pep, iv). In (i), the unfunctionalized NPs do not appreciably enrich protein as seen in NP-control elution lane, demonstrating the resistance of the NPs to non-specific protein adsorption. In (ii), the reaction of the cysteine-thiol with BAPTES is inhibited at acidic pH (pH 5.0), leading to poor NP-peptide conjugation and downstream enrichment of cTnI. In (iii), the reaction of the cysteine-thiol with BAPTES occurs readily and specifically at slightly alkaline pH (pH 8.0), leading to NP-peptide conjugation. However, the use of a negative-binding sequence peptide in (iii) results in poor cTnI enrichment. In (iv), the addition and use of the high-affinity cTnI binding peptide at slightly alkaline (pH 8.0) coupling conditions results in effective cTnI enrichment. All NP samples were subjected to the same enrichment workflow. Equal protein amount (500 ng) of the loading mixture (L), flow-through (F), and elution mixture after enrichment (E) was loaded on the gel. 200 ng loading of endogenous human cTnI standard (Std.) was loaded on the gel as a reference.

Figure 26:
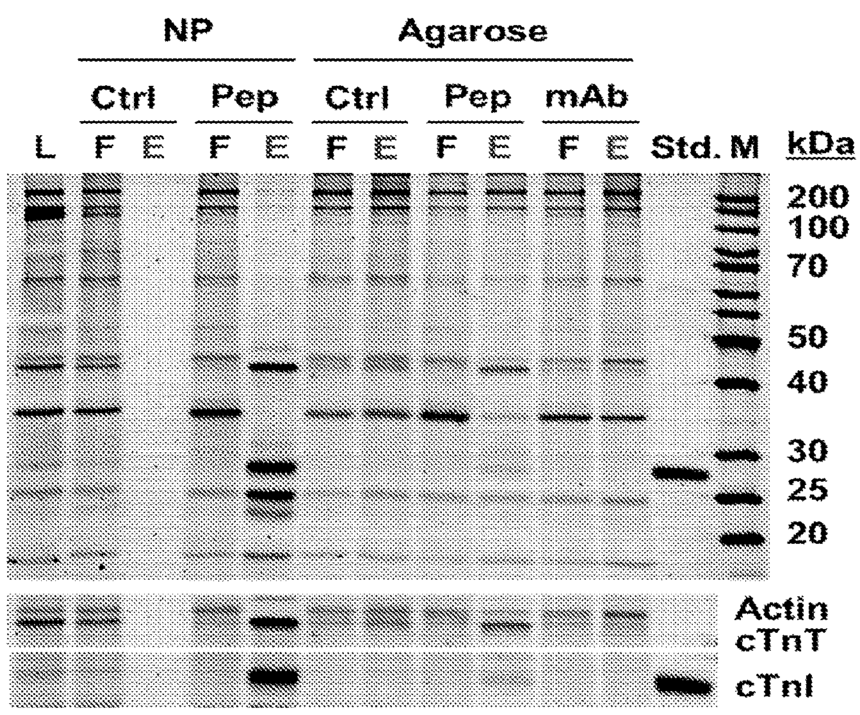

FIG. 26—Comparison of cTnI enrichment performance between NP and Agarose platforms using sarcomeric protein mixtures extracted from a human donor heart. SDS-PAGE stained with SYPRO Ruby visualizing the enrichment performance of the NP control (NP-Ctrl, no peptide), high affinity peptide-functionalized NP (NP-Pep), agarose-control (Agarose-Ctrl), high affinity peptide-functionalized agarose (Agarose-Pep), and antibody (mAb M46) functionalized agarose (Agarose-mAb). Sarcomeric protein extract (100 μg) obtained from a human donor heart was used as the loading mixture, such that cTnI (608 ng) was not loaded in excess relative to the targeting ligands functionalized on the NPs or agarose. Lower panels display enlarged SDS-PAGE strips focusing on enrichment of cTnT and cTnI from (L). Equal amount (500 ng) of the loading mixture (L), flow-through (F), and elution mixture after enrichment (E) was loaded on the gel. The NP-Pep demonstrates effective enrichment across the different platforms examined here.

Figure 27:
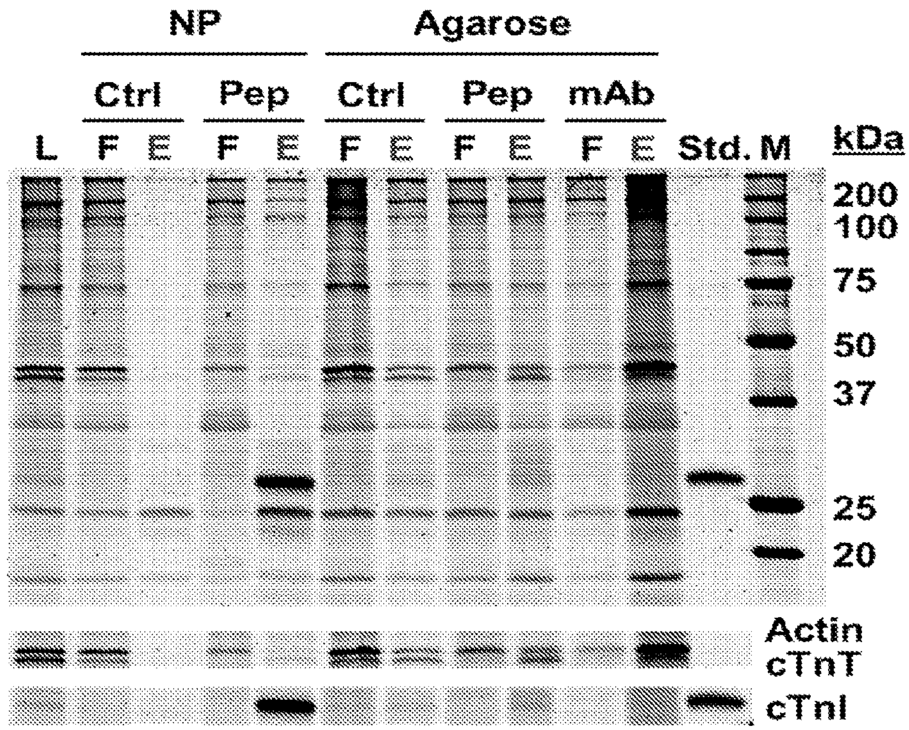

FIG. 27—SDS-PAGE stained with SYPRO Ruby visualizing the enrichment performance of the NP control (NP-Ctrl, no peptide), high affinity peptide-functionalized NP (NP-Pep), agarose-control (Agarose-Ctrl), high affinity peptide-functionalized agarose (Agarose-Pep), and antibody (mAb M46) functionalized agarose (Agarose-mAb). Sarcomeric protein extract (100 μg) obtained from a dilated cardiomyopathy heart was used as the loading mixture, such that cTnI (306 ng) was not loaded in excess relative to the targeting ligands functionalized on the NPs or agarose. Lower panels display enlarged SDS-PAGE strips focusing on enrichment of cTnT and cTnI from (L). Equal amount (500 ng) of the loading mixture (L), flow-through (F), and elution mixture after enrichment (E) was loaded on the gel. The NP-Pep demonstrates effective enrichment across the different platforms examined here.

Figure 28:
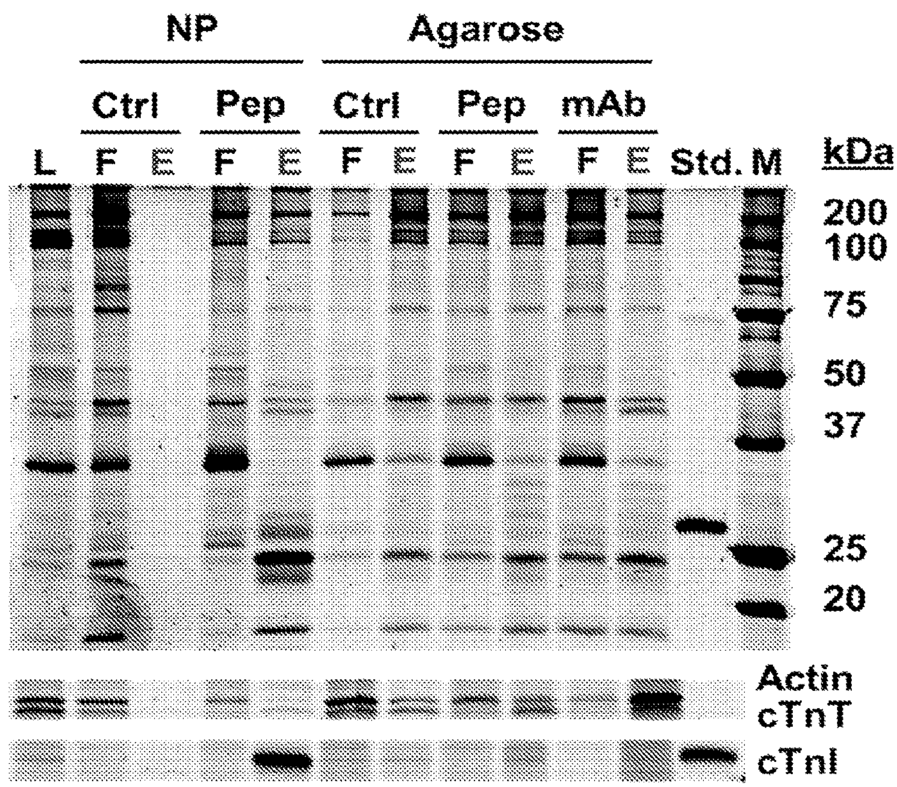

FIG. 28—SDS-PAGE stained with SYPRO Ruby visualizing the enrichment performance of the NP control (NP-Ctrl, no peptide), high affinity peptide-functionalized NP (NP-Pep), agarose-control (Agarose-Ctrl), high affinity peptide-functionalized agarose (Agarose-Pep), and antibody (mAb M46) functionalized agarose (Agarose-mAb). Sarcomeric protein extract (100 μg) obtained from a post-mortem heart was used as the loading mixture, such that cTnI (482 ng) was not loaded in excess relative to the targeting ligands functionalized on the NPs or agarose. Lower panels display enlarged SDS-PAGE strips focusing on enrichment of cTnT and cTnI from (L). Equal amount (500 ng) of the loading mixture (L), flow-through (F), and elution mixture after enrichment (E) was loaded on the gel. The NP-Pep demonstrates effective enrichment across the different platforms examined here.

Figure 29:
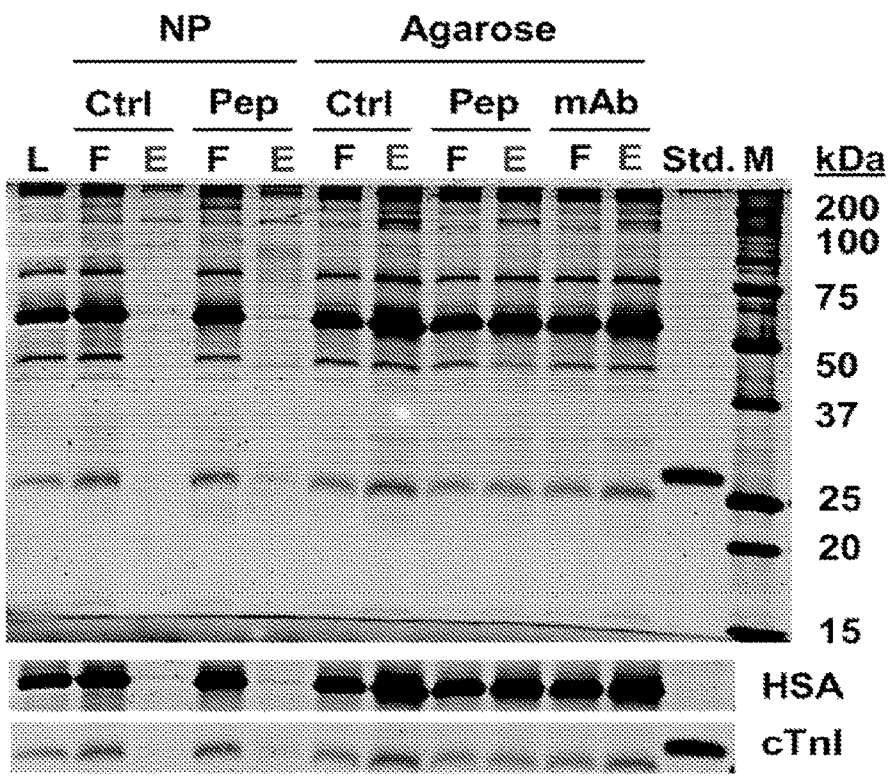

FIG. 29—SDS-PAGE stained with SYPRO Ruby visualizing the enrichment performance of the NP control (NP-Ctrl, no peptide), high affinity peptide-functionalized NP (NP-Pep), agarose-control (Agarose-Ctrl), high affinity peptide-functionalized agarose (Agarose-Pep), and antibody (mAb M46) functionalized agarose (Agarose-mAb). Sarcomeric protein extract (100 μg) containing cTnI (306 ng) obtained from a dilated cardiomyopathy heart was spiked in human serum (10 mg) and used as the loading mixture, such that cTnI was not loaded in excess relative to the targeting ligands functionalized on the NPs or agarose. Lower panels display enlarged SDS-PAGE strips focusing on depletion of HSA from the NP elution, and enrichment of cTnI. With 500 ng equal loading per lane, NP-Pep demonstrates effective enrichment across the different platforms examined here.

Figure 30:
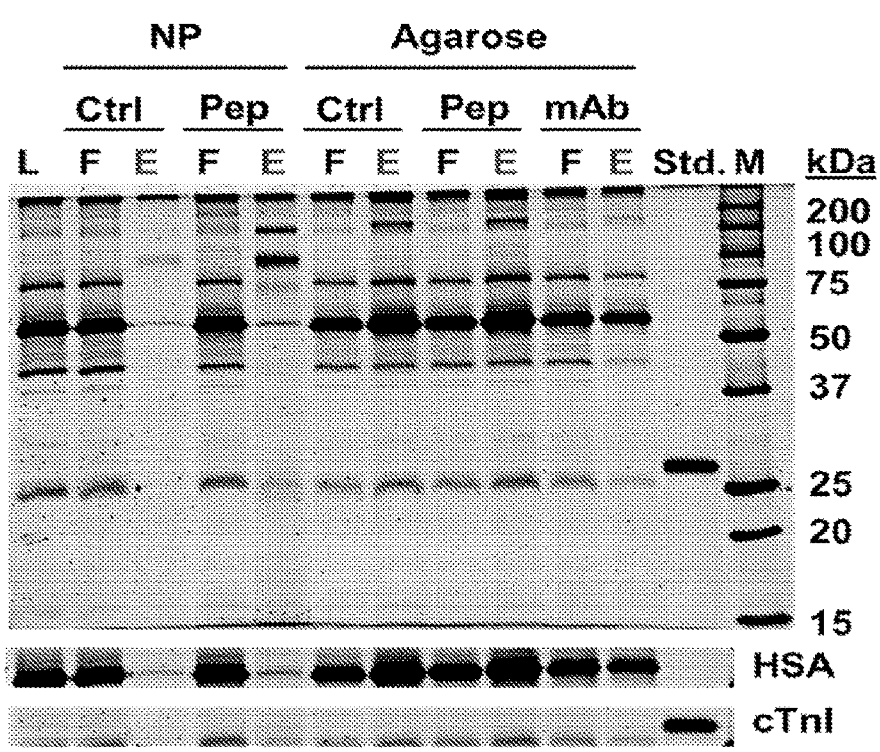

FIG. 30—SDS-PAGE stained with SYPRO Ruby visualizing the enrichment performance of the NP control (NP-Ctrl, no peptide), high affinity peptide-functionalized NP (NP-Pep), agarose-control (Agarose-Ctrl), high affinity peptide-functionalized agarose (Agarose-Pep), and antibody (mAb M46) functionalized with agarose (Agarose-mAb). Sarcomeric protein extract (100 μg) containing cTnI (482 ng) obtained from a post-mortem heart was spiked in human serum (10 mg) and used as the loading mixture, such that cTnI was not loaded in excess relative to the targeting ligands functionalized on the NPs or agarose. Lower panels display enlarged SDS-PAGE strips focusing on depletion of HSA from the NP elution, and enrichment of cTnI. With 500 ng equal loading per lane, NP-Pep demonstrates effective enrichment across the different platforms examined here.

Figure 31:
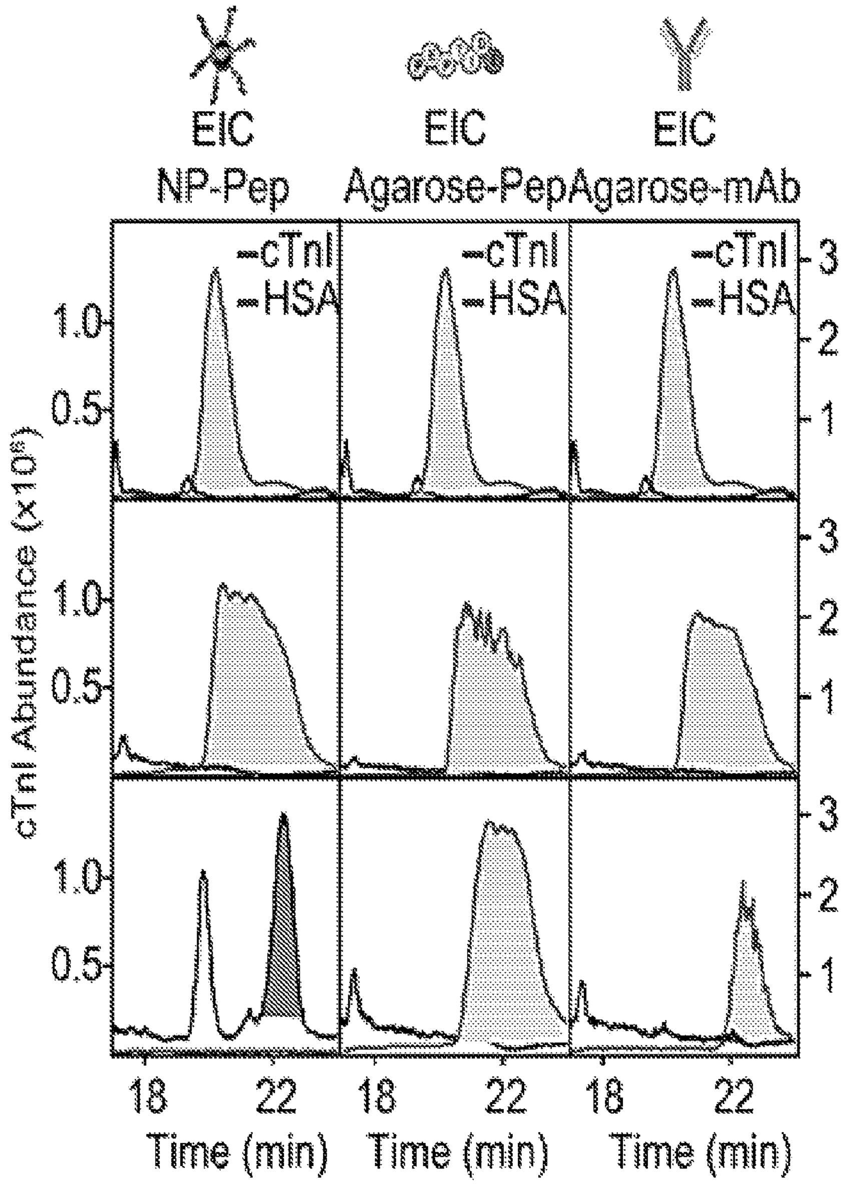

FIG. 31—Normalized extracted ion chromatograms (EICs) of cTnI (black) and HSA (red) corresponding to high affinity peptide-functionalized NP (NP-Pep), high affinity peptide-functionalized agarose (Agarose-Pep), and mAb-functionalized agarose (Agarose-mAb) enrichment from a human serum mixture with spike-in cTnI. cTnI (482 ng) from a human dilated cardiomyopathy heart extract was spiked into human serum (10 mg).

Figure 32:
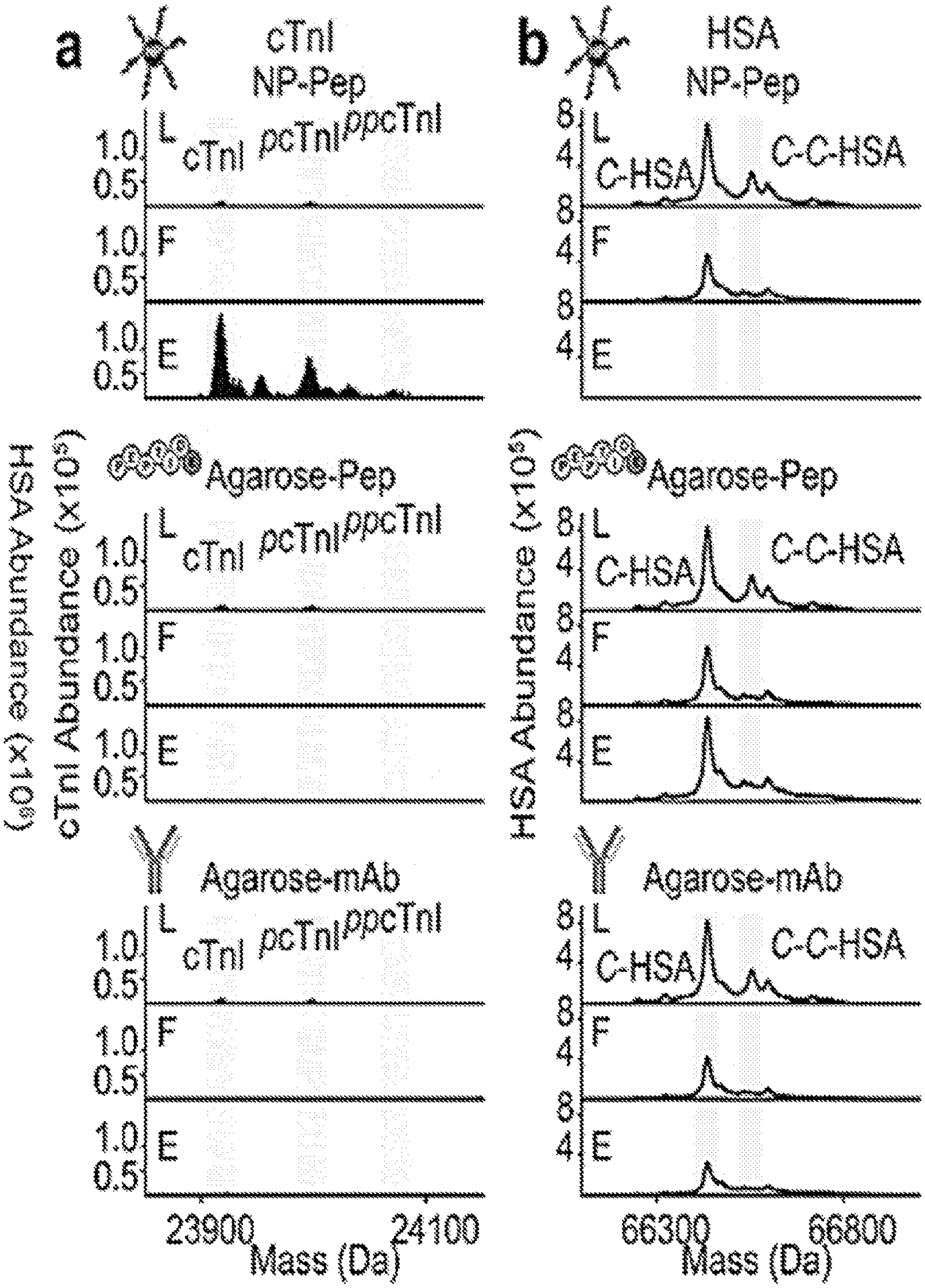

FIG. 32-*a*, Normalized deconvoluted mass spectra of cTnI obtained from the L, F, and E mixtures, corresponding to the data presented in FIG. 31. The high affinity peptide functionalized NPs (NP-Pep) show superior cTnI enrichment from human serum compared to the agarose functionalized with either the same high affinity peptide or a mAb targeting for the same epitope region as the peptide. b, Normalized deconvoluted mass spectra of HSA obtained from the L, F, and E mixtures and corresponding to the data presented in FIG. 31. The NP-Pep demonstrates superior resistance to non-specific HSA adsorption compared to Agarose-Pep and Agarose-mAb. cTnI proteoforms (N-terminally acetylated following Met excision) were identified using accurate intact mass measurement, using the most abundant mass based on the amino acid sequence of entry name TNNI3_human from the UniProtKB sequence database. (L), loading mixture; (F), flow-through; (E), elution mixture; p., phosphorylation; pp., bisphosphorylation. C-HSA, cysteinylated human serum albumin; C-C-HSA, doubly-cysteinylated human serum albumin.

Figure 33:
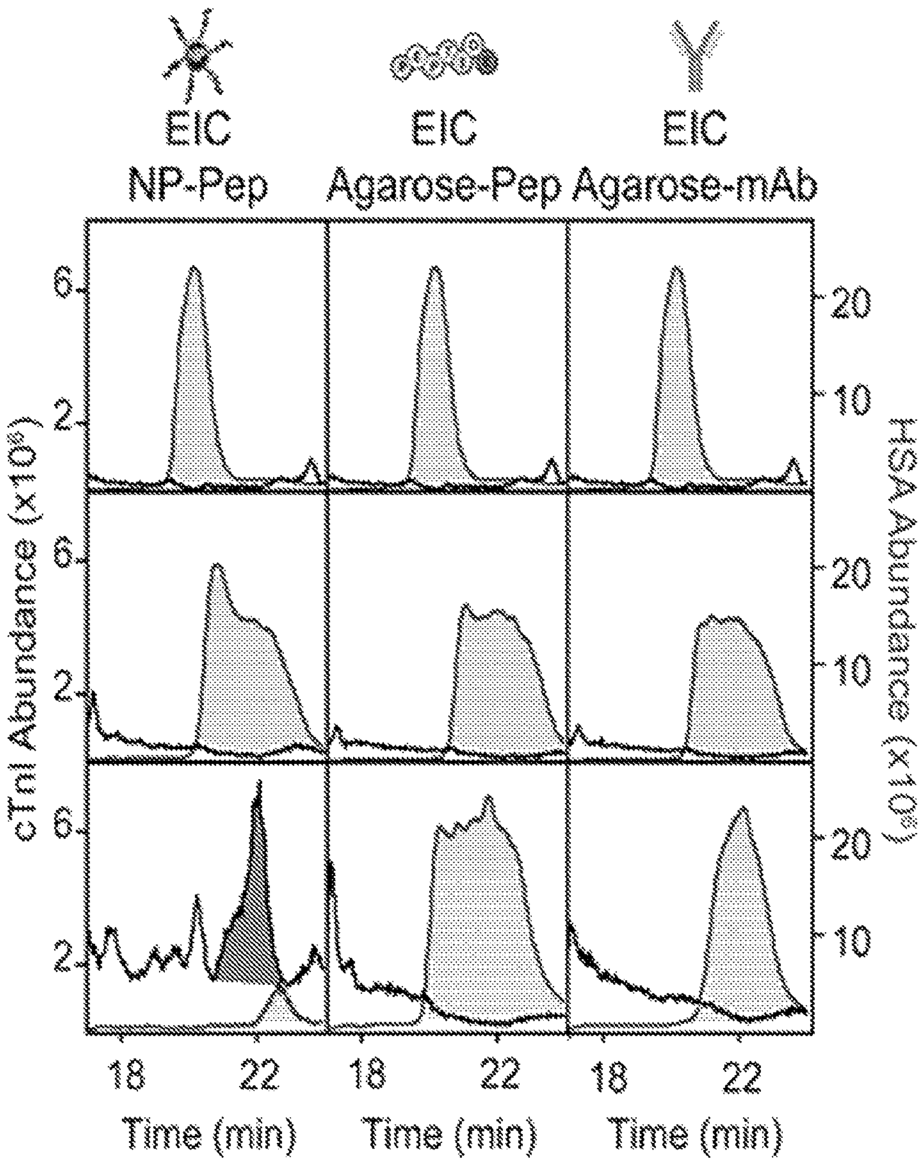

FIG. 33—Normalized extracted ion chromatograms (EICs) of cTnI (black) and HSA (red) corresponding to high affinity peptide-functionalized NP (NP-Pep), high affinity peptide-functionalized agarose (Agarose-Pep), and mAb-functionalized agarose (Agarose-mAb) enrichment from a human serum mixture with spike-in cTnI. cTnI (465 ng) from a post-mortem heart extract was spiked into human serum (10 mg).

Figure 34:
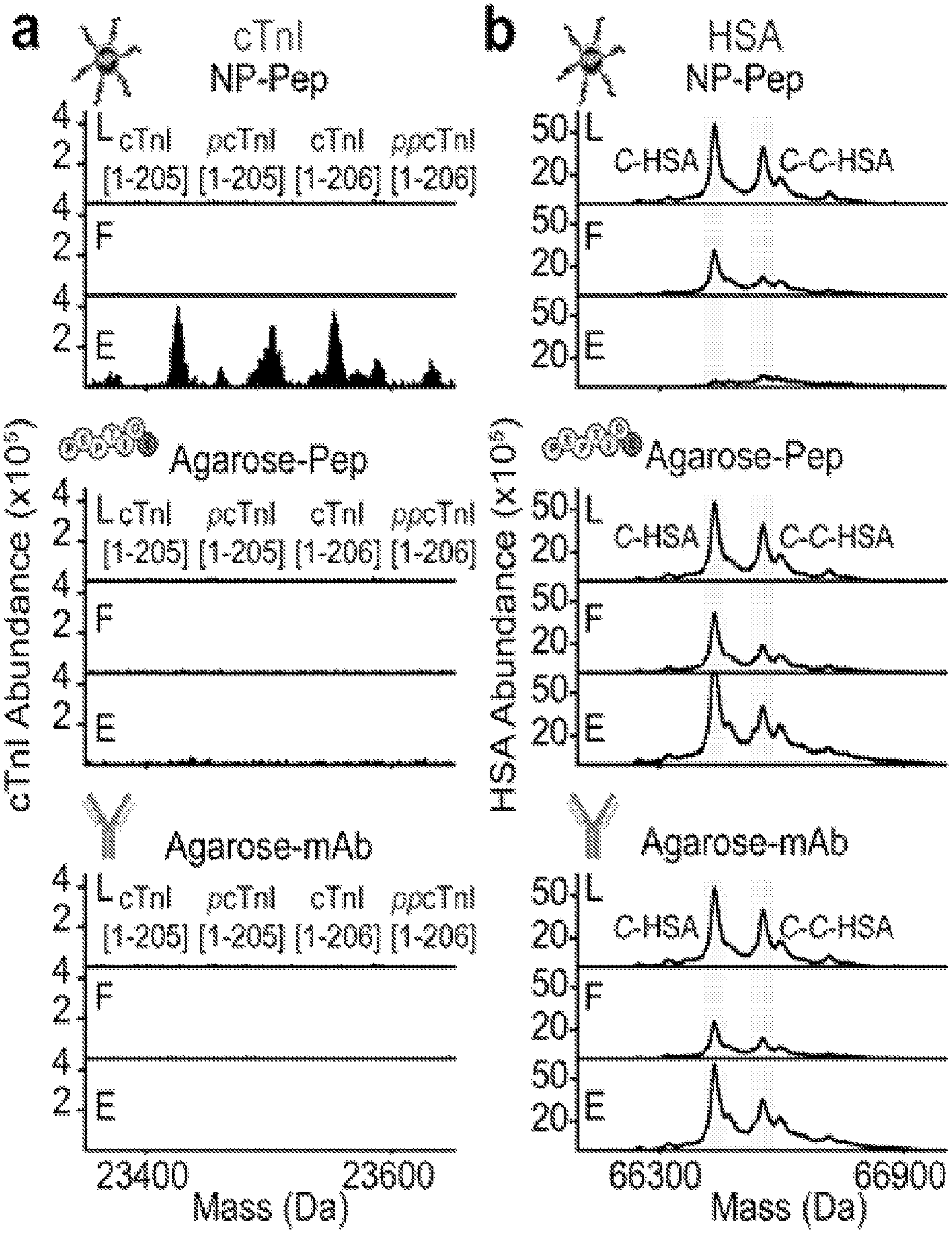

FIG. 34-*a*, Normalized deconvoluted mass spectra of cTnI obtained from the L, F, and E mixtures, corresponding to the data presented in FIG. 33. The high affinity peptide functionalized NPs (NP-Pep) show superior cTnI enrichment from human serum compared to the agarose functionalized with either the same high affinity peptide or a mAb targeting for the same epitope region as the peptide. b, Normalized deconvoluted mass spectra of HSA obtained from the L, F, and E mixtures and corresponding to the data presented in FIG. 33. The NP-Pep demonstrates superior resistance to non-specific HSA adsorption compared to Agarose-Pep and Agarose-mAb. cTnI proteoforms (N-terminally acetylated following Met excision) were identified using accurate intact mass measurement, using the most abundant mass based on the amino acid sequence of entry name TNNI3_human from the UniProtKB sequence database. (L), loading mixture; (F), flow-through; (E), elution mixture; p., phosphorylation; pp., bisphosphorylation. C-HSA, cysteinylated human serum albumin; C-C-HSA, doubly-cysteinylated human serum albumin.

Figure 35:
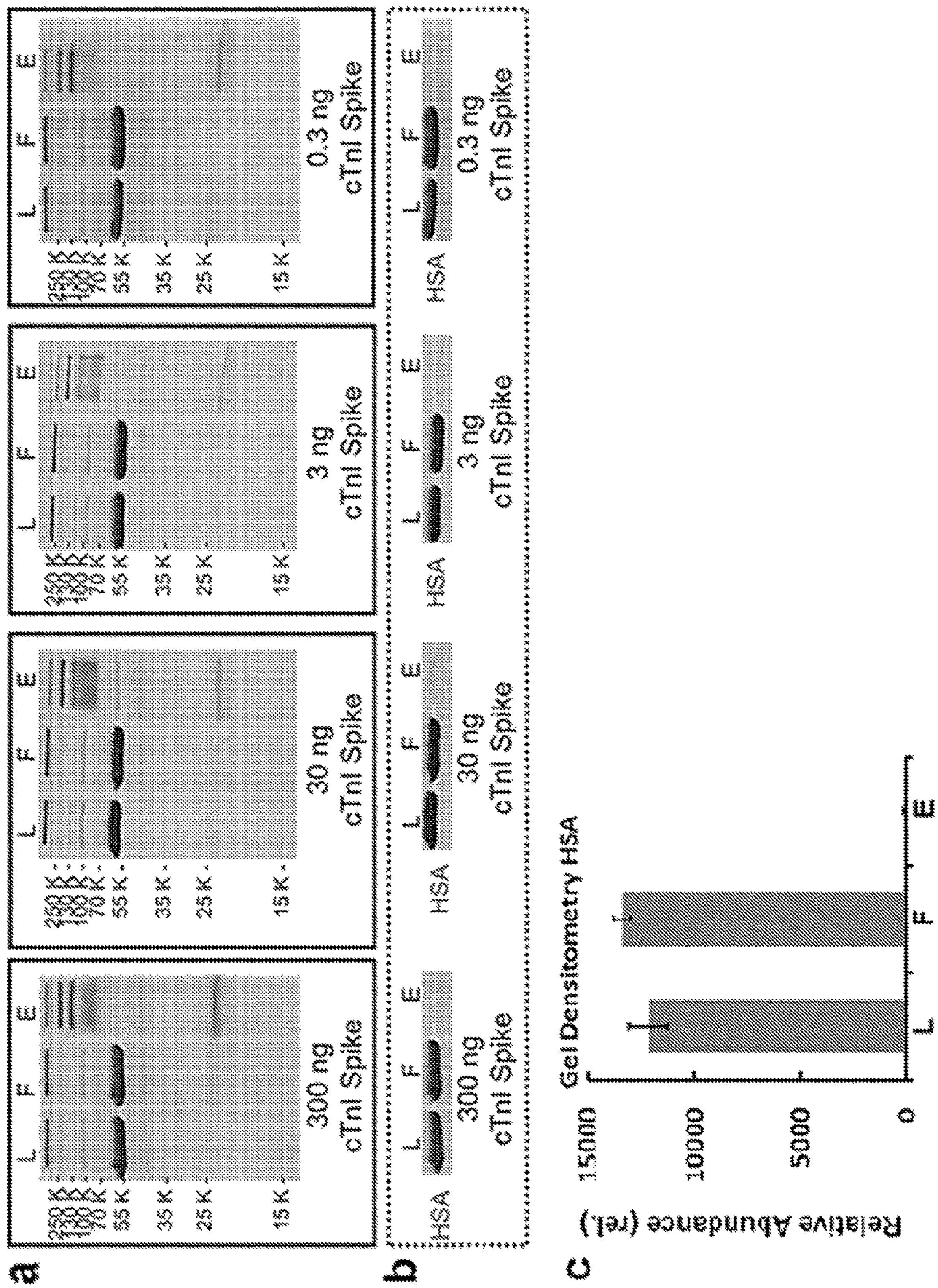

FIG. 35—Simultaneous depletion of human serum albumin (HSA) from protein mixture during NP-Pep enrichment of cTnI. a, SDS-PAGE stained with Coomassie blue demonstrating simultaneous HSA depletion during cTnI enrichment using the NP platform from human serum (20 mg) at various spike-in cTnI concentrations (0.3 to 300 ng/ml). Equal amount (5 μg) of the loading mixture (L), flow-through (F), and elution mixture after enrichment (E) was loaded on the gel. b, Zoom-in of the HSA lane corresponding to (a). c, Gel densitometry relative quantitation of HSA depletion corresponding to the results shown in (a) and (b). HSA was depleted ~215-fold relative to the loading mixture following NP enrichment by ImageJ analysis. Data is representative of n=4 independent experiments and error bars indicate standard deviation from the mean.

Figure 36:
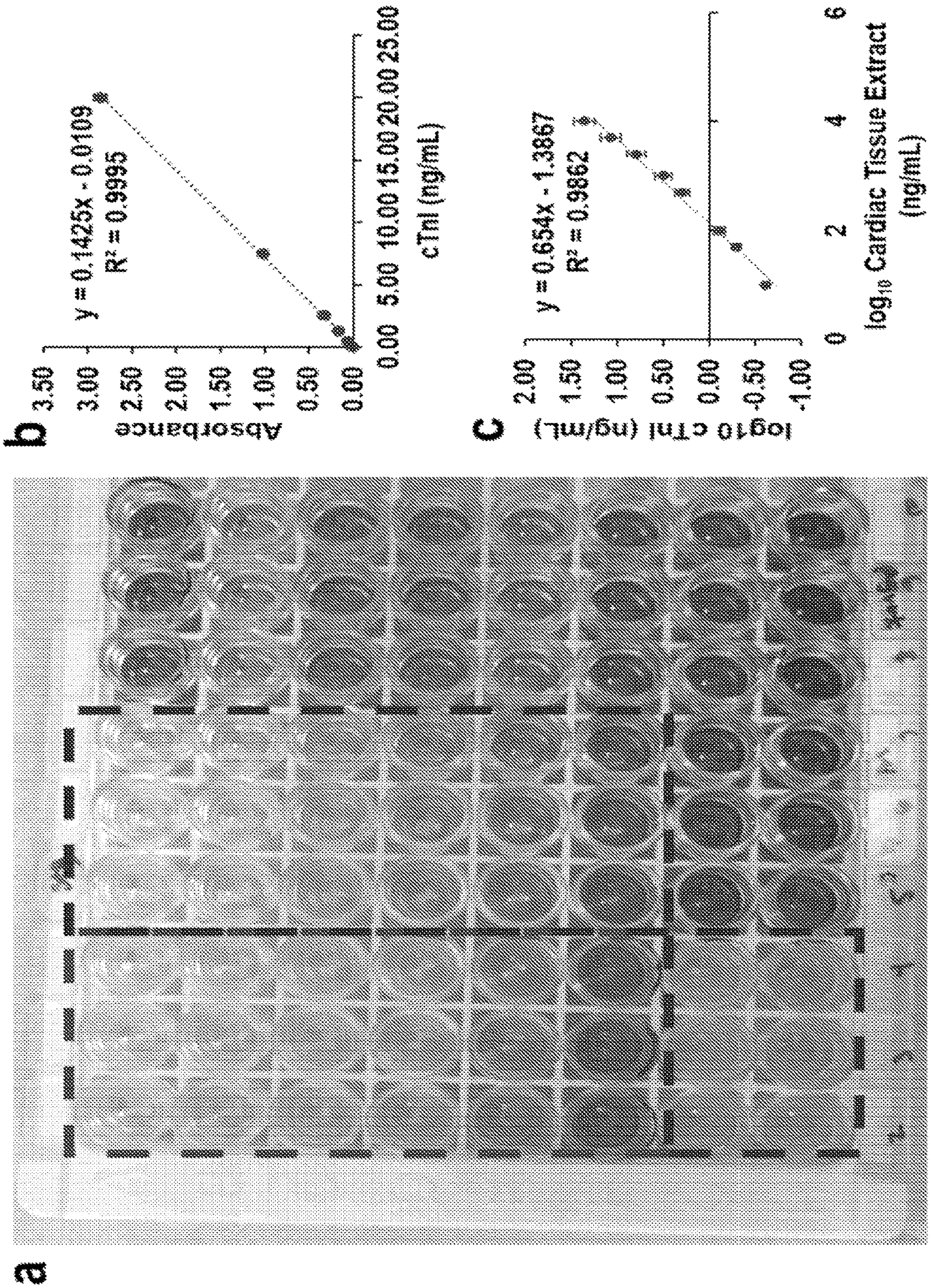

FIG. 36-*a*, ELISA-based colorimetric quantification of cTnI standards (left dashed box) and serum samples incrementally spike-in with sarcomeric protein extracts containing cTnI (bottom and right dashed boxes). All samples were dispensed in triplicate and the assay was performed according to the manufacturer's instructions. The ELISA assay uses capture antibodies targeting cTnI amino acids 18-28 and 86-90, with detection antibodies targeting cTnI amino acids 41-49. b, ELISA-based standard curve (0 ng, 0.4 ng, 1.25 ng, 2.5 ng, 7.5 ng, 20 ng) used for quantification of cTnI spike-in human serum, and quantification of MS-based sensitivity of cTnI detection. c, Log-log plot of cTnI concentration (ng/ml) quantified by ELISA, as a function of total sarcomeric protein spiked into serum (ng/ml) quantified by Bradford protein assay. Approximately 1 μg of sarcomeric protein extract contains 3 ng of cTnI. Data is representative of n=3 independent experiments and error bars indicate standard deviation from the mean.

Figure 37:
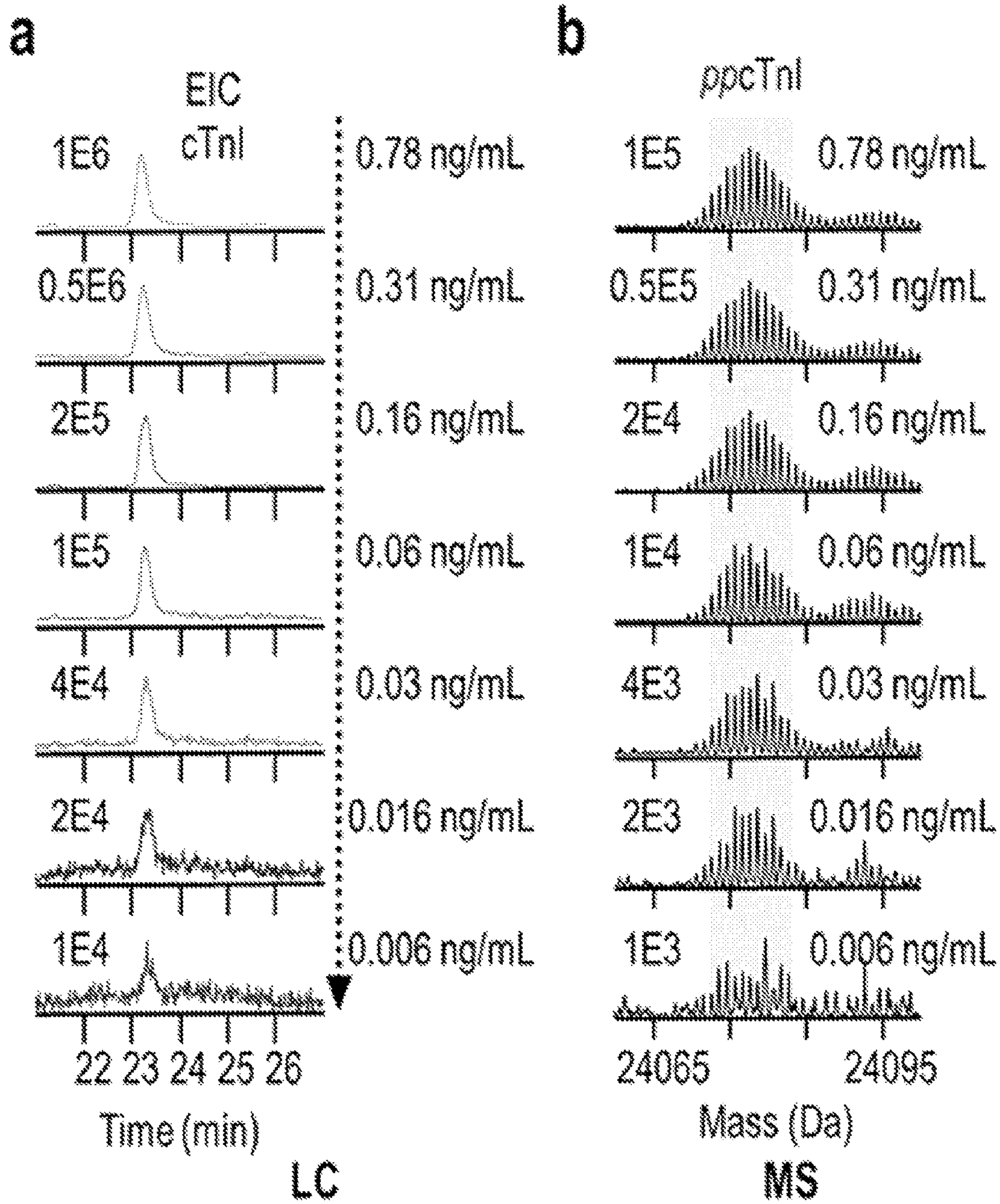

FIG. 37-*a*, Extracted ion chromatograms (EICs) for cTnI at various loading amounts (3.1-0.006 ng/ml) obtained from a heart tissue extract from a healthy donor heart tissue. Data corresponds to the same data presented in FIG. 7, panel b. b, Deconvoluted mass spectra corresponding to the same data presented in (a). ppcTnI is the most abundant proteoform of cTnI and is highlighted to illustrate the linear decrease in raw signal abundance as a function of concentration 3.1-0.006 ng/ml.

Figure 38:
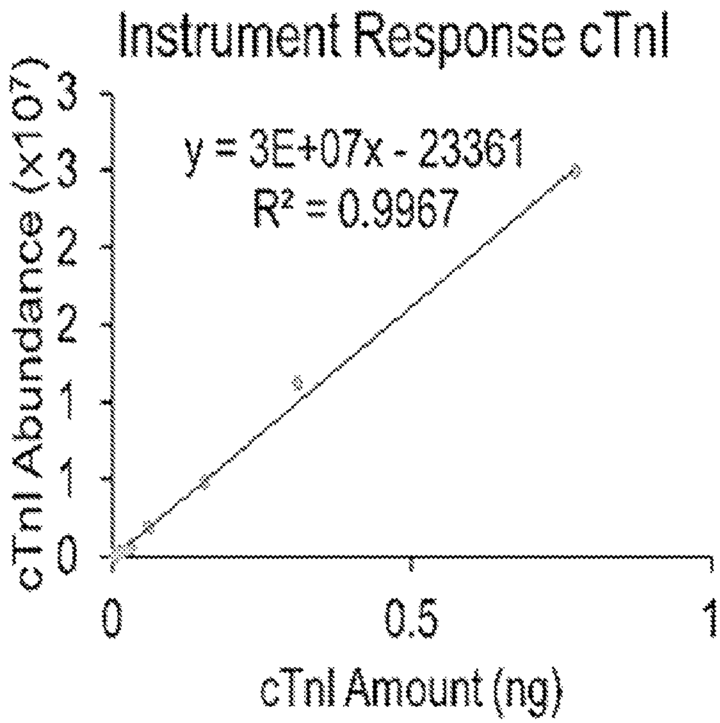

FIG. 38-*a*, Plot of relative cTnI abundance obtained from (a) at the various loadings tested demonstrating linearity of MS-detection and response. LOD (3.3/s) 0.06 ng/ml; LOQ (10 σ/s): 0.2 ng/ml. b, Table summarizing the MS analysis of the data presented in (a) and FIG. 37. The mass accuracy (monoisotopic mass) at each tested cTnI loading is shown. All data is representative of n=2 independent experiments.

Figure 39:
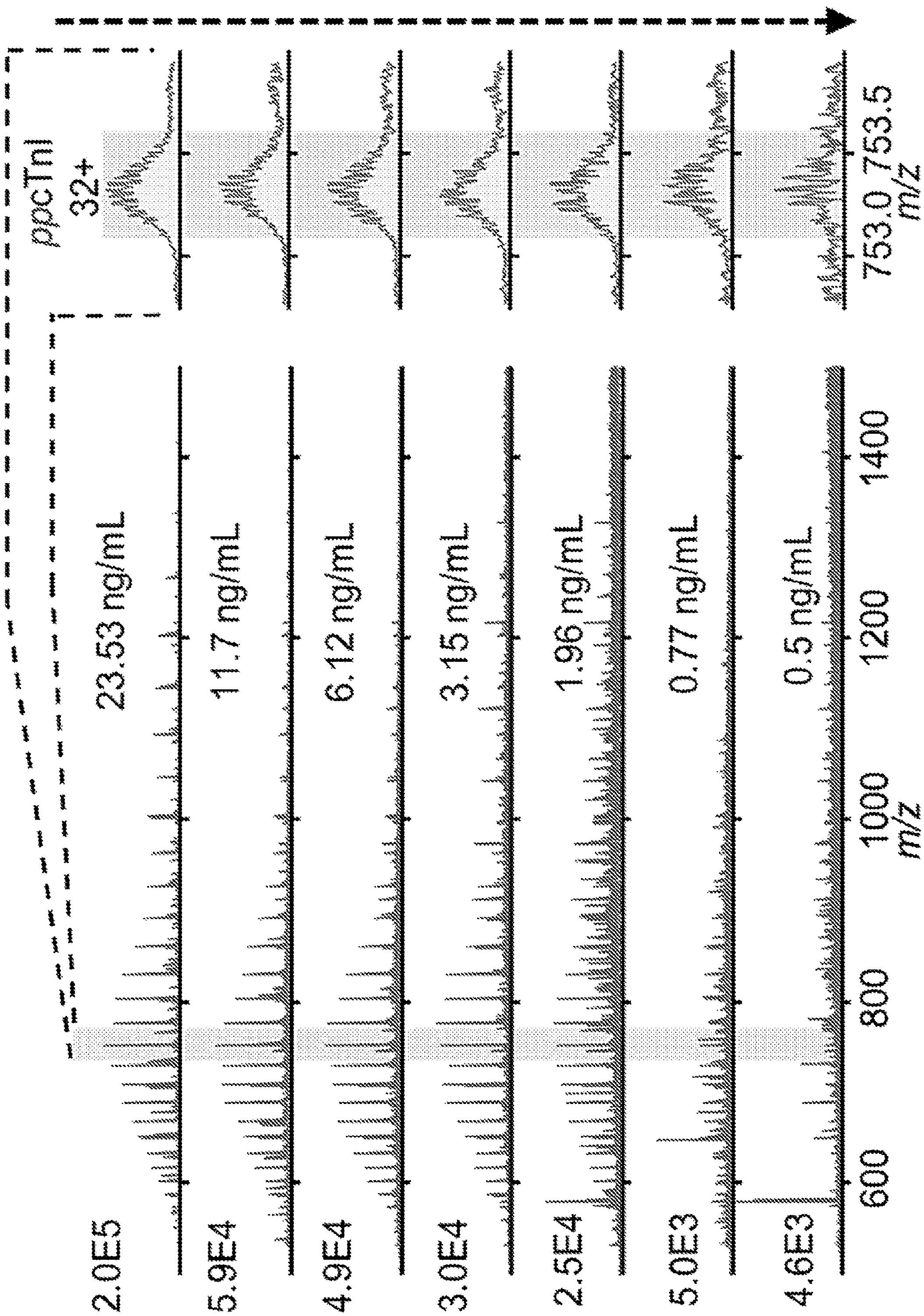

FIG. 39—Sensitivity of Top-Down MS-based cTnI assay using the nanoproteomics platform. Normalized raw mass spectra corresponding to the same data presented in FIGS. 7-9. The most abundant signal, ppcTnI charge state 32+, is highlighted to illustrate the raw signal abundance as a function of concentration 22.53 ng/ml to 0.50 ng/ml. pp, bisphosphorylation.

Figure 40:
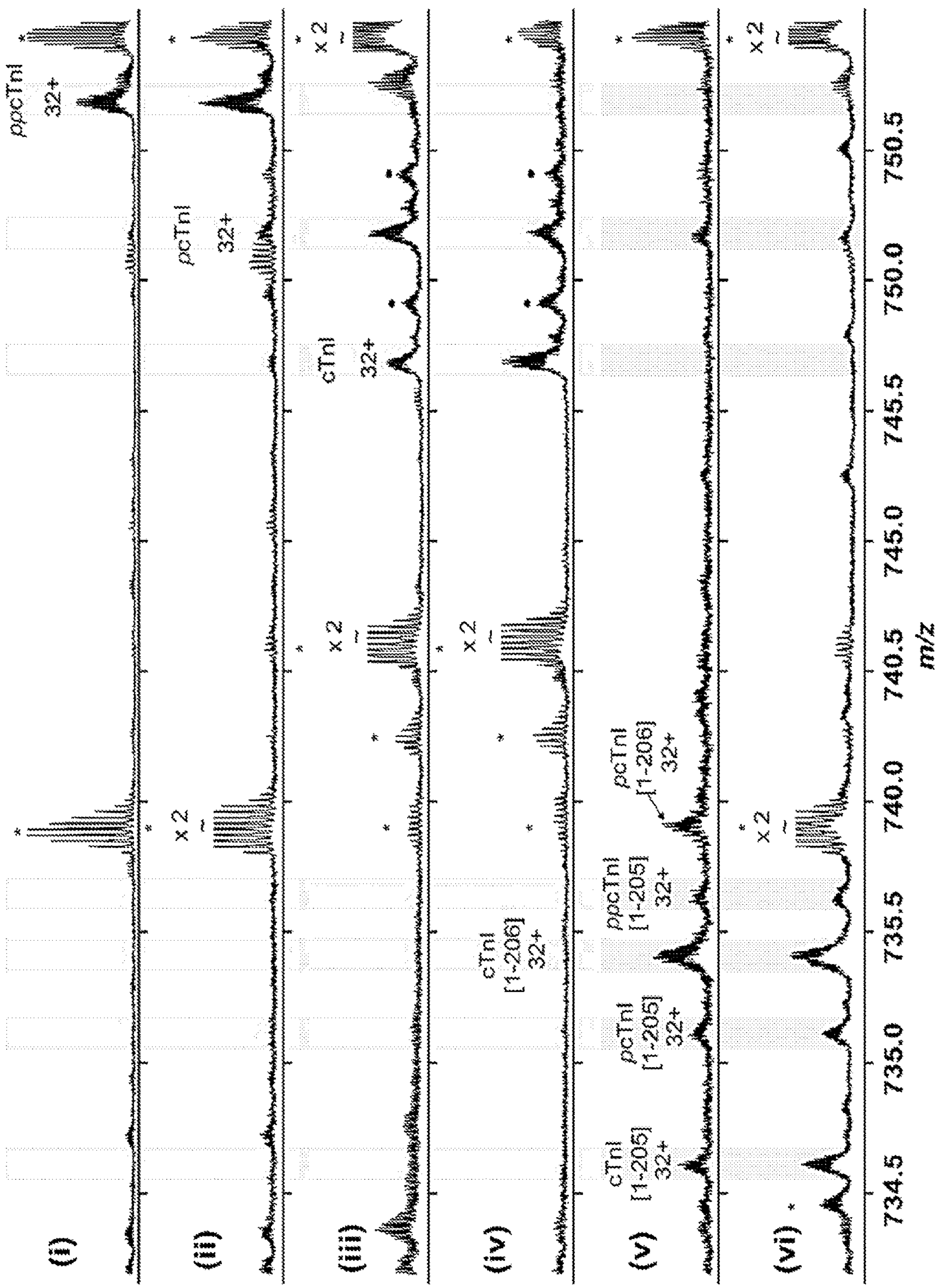

FIG. 40—LC/MS analysis of cTnI proteoforms enriched directly from human serum by NP-Pep. Normalized raw mass spectra data corresponding to deconvoluted mass spectra shown in FIG. 10. The cTnI (~10-20 ng/ml) spiked in the human serum (10 mg) are extracted from various human hearts: (i) and (ii), donor hearts; (iii) and (iv), diseased hearts with dilated cardiomyopathy, (v) and (vi), post-mortem hearts. p., phosphorylation. pp., bisphosphorylation. Data is representative of n=3 independent experiments. Asterisks "*" indicate coeluting serum proteins and circles "." indicate other cTnI proteoforms. A summary of the enriched proteoforms from serum and their respective mass measurements by top-down MS are listed in Table 5.

Figure 41:
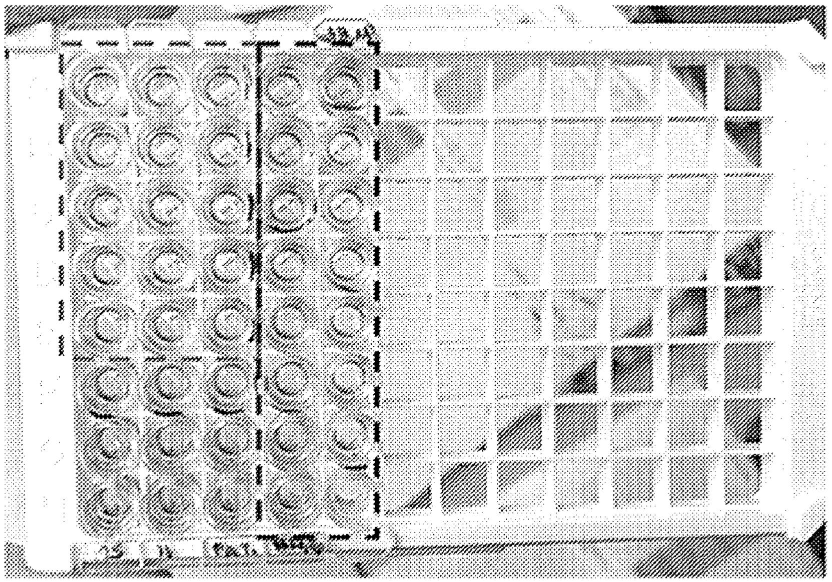
Figure 41:
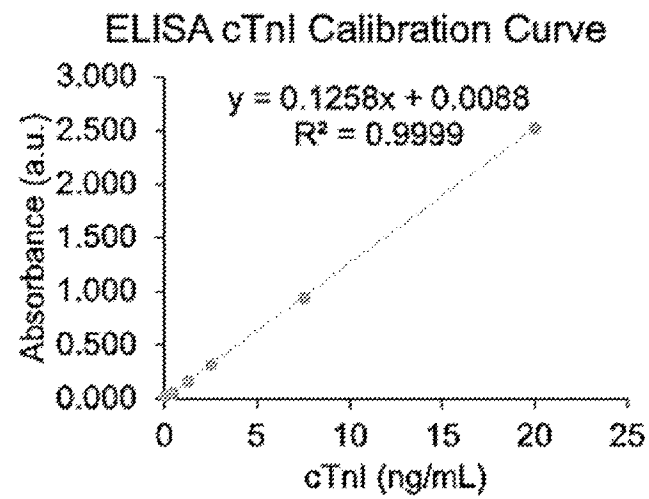

FIG. 41-*a*, ELISA-based colorimetric quantification of cTnI standards (left dashed box) and enrichment samples (right dashed box). b, ELISA-based standard curve (0 ng, 0.4 ng, 1.25 ng, 2.5 ng, 7.5 ng, 20 ng) used for quantification of cTnI amount before enrichment and after enrichment by NP-Pep or Agarose-mAb. c, Summary of enrichment performance results for NP-Pep (tissue/serum) and Agarose-mAb (serum).

Figure 42:
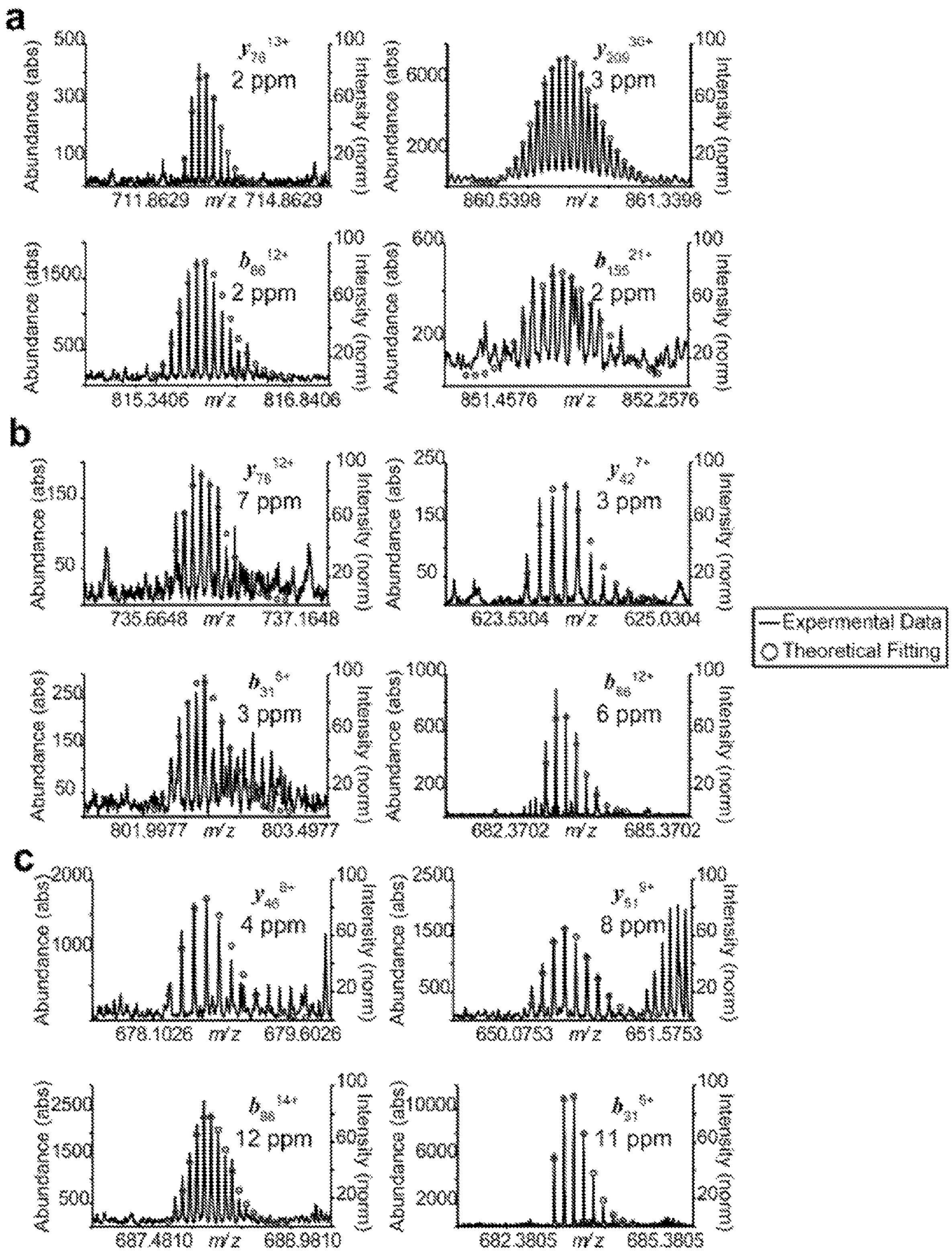

FIG. 42-*a-c*, Representative CID fragment ions obtained from cTnI arising from donor heart $$\left(y_{76}^{13+},\ y_{209}^{30+},\ b_{86}^{12+},\text{ and }b_{155}^{21+}\right),$$

diseased heart $$\left(y_{76}^{12+},\ y_{42}^{7+},\ b_{31}^{5+},\text{ and }b_{86}^{12+}\right),$$

and post-mortem heart $$\left(y_{76}^{8+},\ y_{51}^{9+},\ b_{86}^{14+},\text{ and }b_{31}^{5+}\right)$$

sources.

Figure 43:
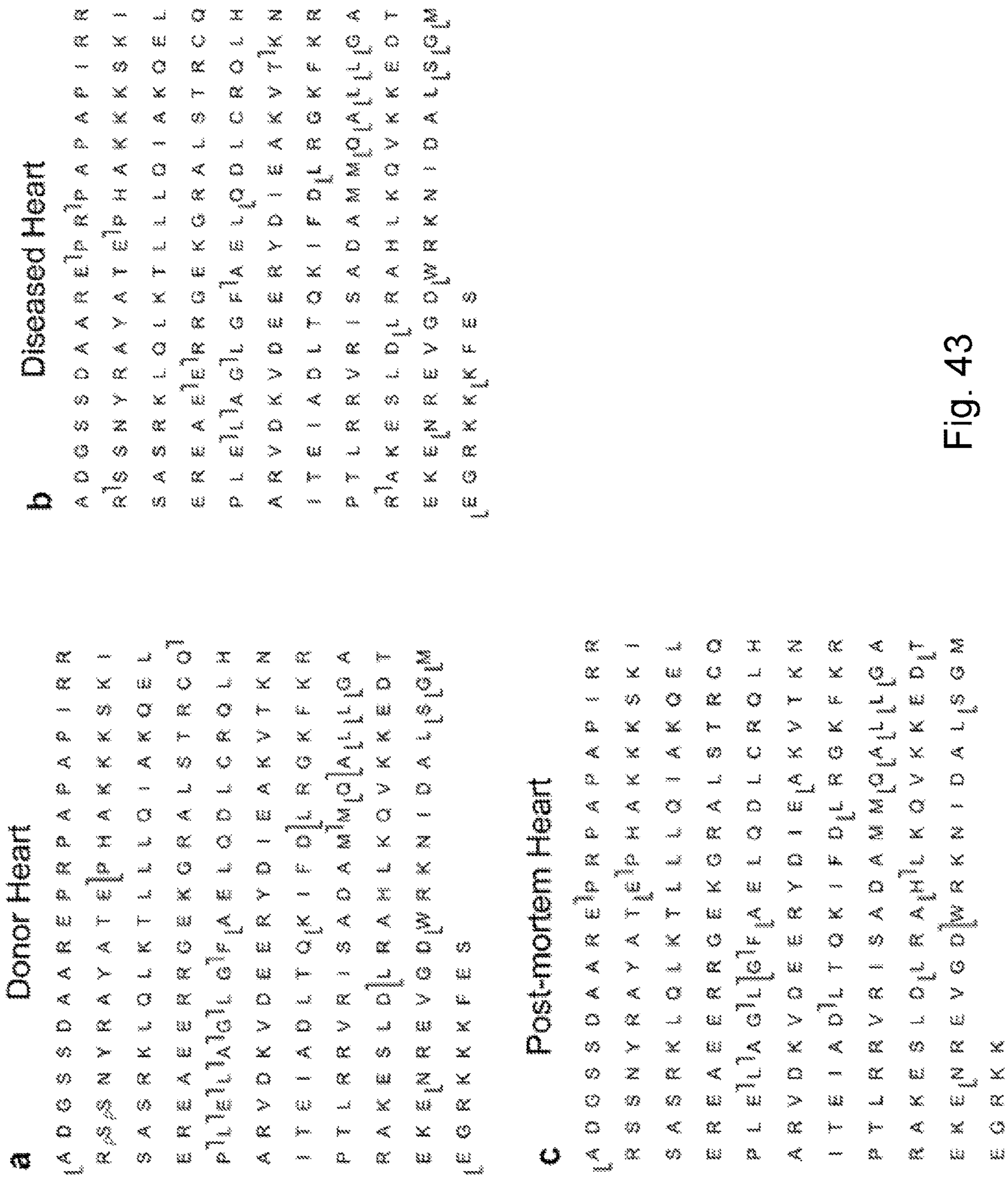

FIG. 43-*a-c*, Protein sequence fragmentation mapping of the specific proteoform of cTnI corresponding to the fragment ion data obtained from each cTnI source (FIG. 42) (SEQ ID NOs: 4-6). CID fragmentations are shown as cleavages. Amino acid sequence was based on the entry name TNNI3_human obtained from the UniProtKB sequence database (SEQ ID NO: 4).

Figure 44:
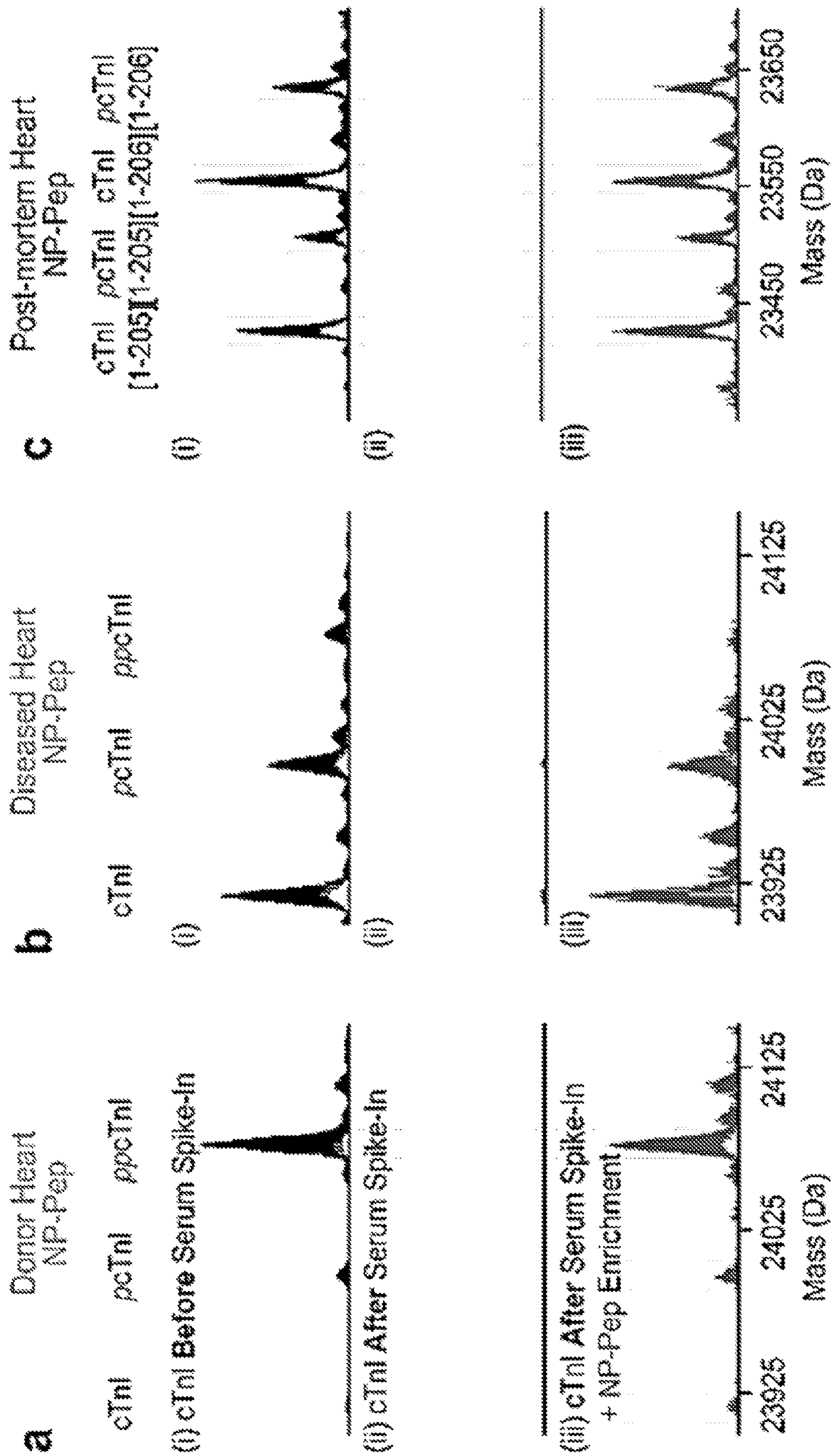

FIG. 44—Representative deconvoluted mass spectra corresponding to cTnI proteoforms originating from a donor heart (a), a diseased dilated cardiomyopathie heart (b), and a post-mortem heart (c) before serum spike-in (i), after serum spike-in (ii), and after NP-Pep enrichment of human serum spiked with cTnI (iii). p=phosphorylation; pp=bisphosphorylation.

DETAILED DESCRIPTION OF THE INVENTION

Cardiovascular diseases are the leading causes of death globally (Benjamin et al., 2018, Circulation, 137: e67-e492), account for approximately one out of every four deaths in the United States, and further place an enormous financial burden on the healthcare system. Early and accurate diagnosis of heart failure enables successful patient outcomes and reduces the need for excessive and costly testing.

Cardiac troponin I (cTnI) is an important protein in cardiomyocytes that regulates cardiac muscle contraction (Lemos et al., 2013, JAMA, 309:2262). cTnI is also clinically recognized as a sensitive and specific 'gold-standard' protein biomarker for acute coronary syndrome because it has an amino acid sequence specific to the cardiac tissue and is released into the bloodstream following cardiac injury (Missov et al., 1997, Circulation, 96:2953-2958) with an increased circulating cTnI concentration correlated to the onset of cardiac damage (Thygesen et al., 2018, Journal of the American College of Cardiology, 25285; Westermann et al., 2017, Nature Reviews Cardiology, 14: 472; Antman et al., 1996, New England Journal of Medicine 335: 1342-1349). Increased cTnI levels in the bloodstream are associated with myocardial injuries such as AMI and ischemia. To date, antibody-based assays testing for elevated levels of cTnI in the bloodstream are the primary tests used to diagnose AMI.

However, high-sensitivity immunoassays used to detect elevated cTnI levels often yield inconsistent results and contribute to false observations of elevated cTnI levels in non-AMI patients. While current cTnI assays have a high negative predictive value (>99%) leading to very few cases of "false-negative" AMI diagnosis, the positive predictive value (28.8%) is low. As a result, current cTnI antibody-based immunoassays contribute to increased cardiology consultation and medical testing. Thus, an improved assay for accurately detecting cTnI is of interest for accurate diagnosis, risk stratification, and outcome assessment for patients with ACS and non-ACS myocardial injury.

Additionally, circulating cTnI in the blood exists in low abundance and in myriad proteoforms (Smith et al., 2013, Nature Methods 10: 186), such as phosphorylated, truncated, acetylated, and oxidized proteoforms, that are known to reflect pathophysiological processes (Bates et al., 2010, Clinical Chemistry, 56: 952; Madsen Lene et al., 2006, Circulation Research, 99: 1141-1147; and Soetkamp et al., 2017, Expert Review of Proteomics 14: 973-986). Current antibody-based enzyme-linked immunosorbent assays (ELISAs) for cTnI are incapable of distinguishing these modified cTnI proteoforms, and elevated cTnI concentrations indirectly quantified by ELISA are not indicative of the pathology underlying cardiac myocyte injury (Soetkamp et al., 2017, Expert Review of Proteomics 14: 973-986; and Labugger et al., 2000, Circulation, 102: 1221-1226). Moreover, the intrinsic limitations of immunoassays such as batch-to-batch variation, heterophilic antibody interference, and lack of standardization in the use of antibodies targeting different epitopes yield inconsistent results across laboratories and a high false discovery rate (Twerenbold et al., 2017, Journal of the American College of Cardiology 70: 996-1012; and Tighe et al., 2015, PROTEOMICS—Clinical Applications 9: 406-422). This further contributes to unnecessary and costly health care expenditures.

To address these problems, the examples below provide a proteoform-resolved comprehensive cTnI assay enabled by an integrated nanoproteomics strategy for the specific capture and enrichment of cTnI using functionalized nanoparticles (NPs) followed by top-down mass spectrometry (MS) analysis of various cTnI proteoforms. This nanoproteomics strategy is antibody-free, simple, scalable, and highly reproducible with negligible batch-to-batch variations. The examples demonstrate specific enrichment of cTnI from serum while simultaneously depleting highly abundant serum proteins and importantly, direct detection and quantification of cTnI proteoforms from serum with a limit of detection as low as 0.75 ng/ml. Such proteoform-resolved cTnI assay reveals previously unachievable in-depth molecular details of cTnI as proteoform-specific biomarkers for diagnosis of cardiac diseases with high accuracy.

The nanoparticle strategy described herein for cTnI enrichment is superior to existing method based on antibody-conjugated microparticles for the following reasons: (1) nanoparticles (NPs) are comparable in size to typical proteins to enhance protein capture and enrichment and can penetrate better in complex protein mixtures, leading to a higher interaction rate; (2) this platform enables modular functionalization of the NP surface by accessing the unique reactivity of the allenecarboxamide motif for specific thiol-conjugation of biomolecular recognition molecules and various other small molecules; (3) as biomolecular recognition elements, peptides are synthesized easily and reproducibly at low cost, are pH and temperature stable, and have considerably longer shelf-life compared to antibody-based reagents; and (4) these functionalized NP reagents can be synthesized in large scale with good quality control, which could significantly lower the cost and further minimize the batch-to-batch variation common to antibody production.

Example 1-A Proteoform-Resolved Comprehensive Cardiac Troponin I Assay Enabled by Nanoproteomics Recent studies have convincingly shown that cTnI is heavily modified and its proteoforms arising from various post-translational modifications (PTMs) can provide new insights to the molecular mechanisms underlying various cardiovascular diseases (Soetkamp et al., 2017, Expert Review of Proteomics 14: 973-986; and Labugger et al., 2000, Circulation, 102: 1221-1226). Therefore, a comprehensive and accurate proteoform-resolved cTnI assay is urgently needed. Top-down MS proteomics is ideally suited for this major challenge because it analyzes intact proteins and is the most powerful method to comprehensively characterize proteoforms and decipher PTMs (Chen et al., 2018, Analytical Chemistry, 90: 110-127; Siuti et al., 2007, Nature Methods, 4: 817-821). However, the high dynamic range of the blood proteome (1012) makes detection of low-abundance proteins (such as cTnI) extremely difficult, especially directly from blood serum samples in the presence of many highly abundant proteins such as human serum albumin (HSA) (Anderson et al., 2002, History, Character, and Diagnostic Prospects 1: 845-867). Therefore, protein enrichment is required prior to MS analysis (Anderson et al., 2002, History, Character, and Diagnostic Prospects 1: 845-867; Xie et al., 2009, Expert review of proteomics 6, 573-583; and Smith et al., 2017 Circulation 135: 1651-1664). The following nanoproteomics strategy was therefore developed using surface functionalized magnetic NPs that can capture and enrich cTnI directly from human serum, followed by top-down MS to enable a comprehensive proteoform-resolved cTnI assay.

Figure 1:
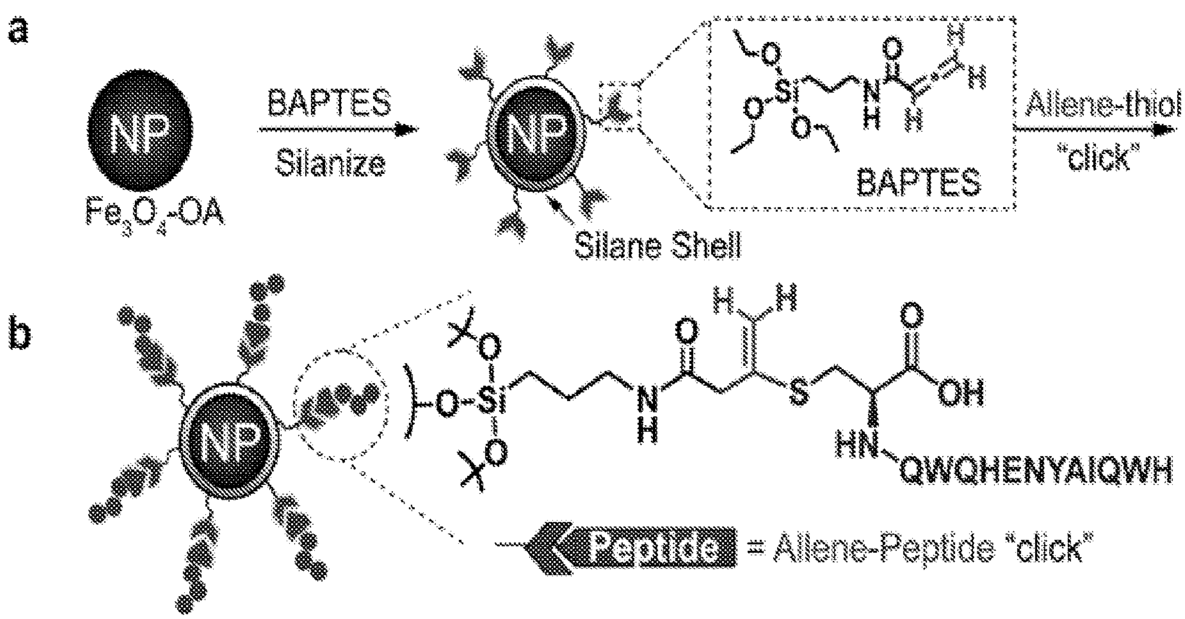
FIG. 1—Design, synthesis, and characterization of surface functionalized magnetic nanoparticles (NPs) for capturing cTnI. Panel a, Silanization of $Fe_3O_4$NPs using an allenecarboxamide-based organosilane monomer (BAPTES) for cysteine thiol-specific bioconjugation. b, Illustration of the rationally designed NPs that are surface functionalized with a 13-mer peptide (SEQ ID NO: 2) that has a high affinity for cTnI (NP-Peptide) for cTnI enrichment. The 13-mer peptide possesses a C-terminal cysteine that selectively reacts with the allenecarboxamide moiety on the silanized NPs (thereby attaching the polypeptide of SEQ ID NO: 1 to the nanoparticle).

Firstly, a surface-functionalized superparamagnetic iron oxide (magnetite, $Fe_3O_4$) NPs (Park et al., 2004, Nature Materials, 3: 891-895) was designed for the capture and specific enrichment of cTnI from complex mixtures (FIG. 1). A novel organosilane ligand N-(3(triethoxysilyl)propyl) buta-2,3-dienamide (see FIG. 1 panel a, and FIGS. 12-15), hereinafter referred to as "BAPTES", was synthesized which was used to silanize the oleic acid coated $Fe_3O_4$ NPs, following a method for reproducible surface silanization (Roberts et al., 2019, Nano Research, 12: 1473-1481). The allenecarboxamide functional group of the BAPTES ligand possesses high chemoselectivity towards the thiol sidechain of cysteine (Cys), and forms a stable and irreversible conjugate that is not prone to hydrolysis (Abbas et al., 2014, Angewandte Chemie International Edition 53: 7491-7494).

Instead of using antibodies to target cTnI, a short, linear peptide was chosen which was evolved for high cTnI affinity by phage display and in silico evolution (Xiao et al., 2018, ACS Sensors 3: 1024-1031). The use of peptides offers attractive properties for protein enrichment in comparison with antibodies, such as improved chemical stability to changes in pH and reducing environments, thermal stability, scalability using solid-phase peptide synthesis, and batch-to-batch reproducibility. This specific peptide (HWQIAYNEHQWQ-SEQ ID NO:1) not only exhibits an impressive binding affinity ($K_d$) of 270 μM comparable to that of antibodies (Xiao et al., 2018, ACS Sensors 3: 1024-1031), but also targets a central portion of cTnI (amino acid residues 114-144) that is less susceptible to proteolysis and postulated to be an optimal targeting epitope to detect all forms of cTnI present in blood circulation (Bates et al., 2010, Clinical Chemistry 56: 952; Katrukha et al., 1998, Clinical Chemistry 44:2433; and Apple et al., 2012, Clinical Chemistry 58: 54).

To evaluate the peptide functionalization approach, the reaction of BAPTES with a C-terminal Cys-modified derivative of the high affinity peptide (HWQIAYNEHQWQC-SEQ ID NO: 2) was first analyzed using high-resolution tandem MS (MS/MS). The peptide-Cys' reaction with BAPTES occurred exclusively even in the presence of other biologically relevant nucleophiles, such as hydroxyls, amines, and carboxylates (FIGS. 16-17).

Figure 2:
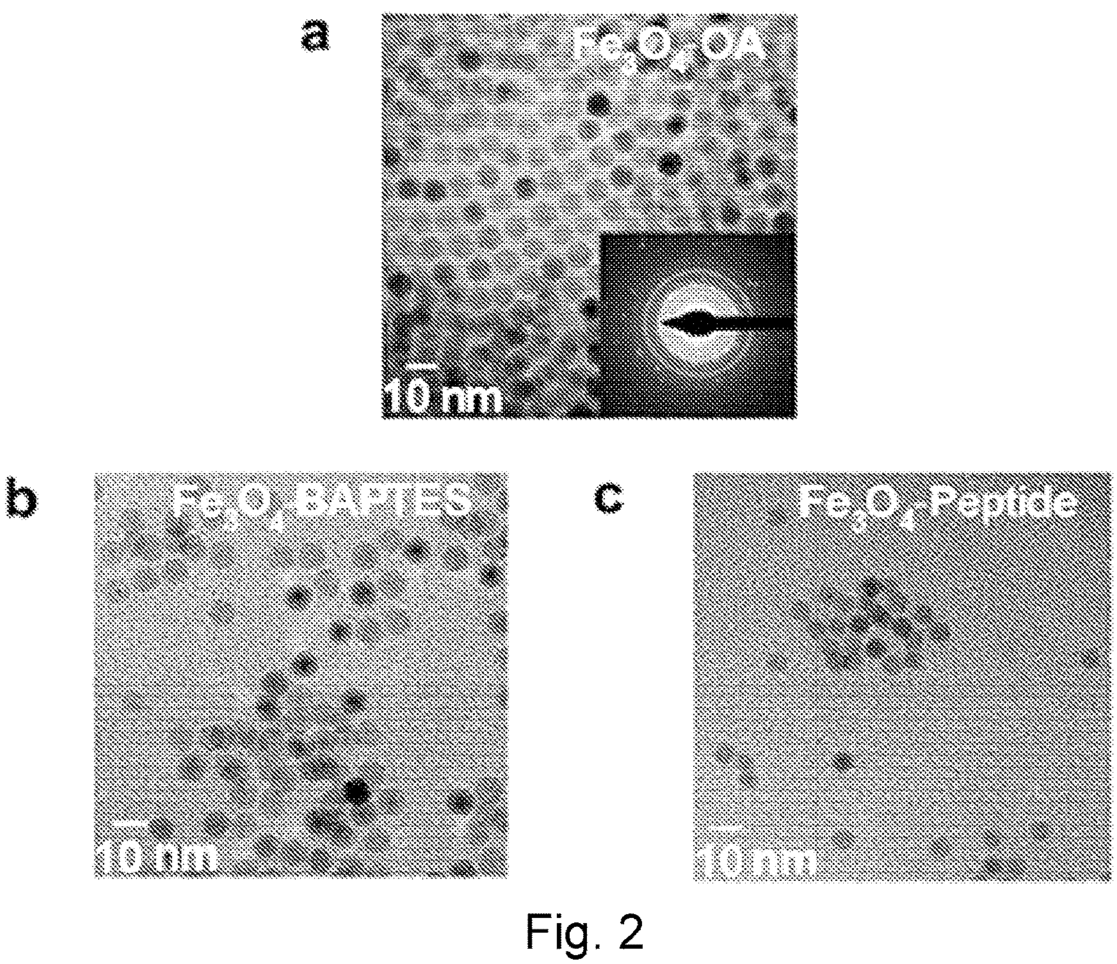
FIG. 2—Representative TEM analysis of surface functionalized NPs: $Fe_3O_4$—OA NPs (a) (inset shows the selected area electron diffraction pattern), $Fe_3O_4$-BAPTES NPs (b), and $Fe_3O_4$-Peptide NPs (c).
Figure 3:
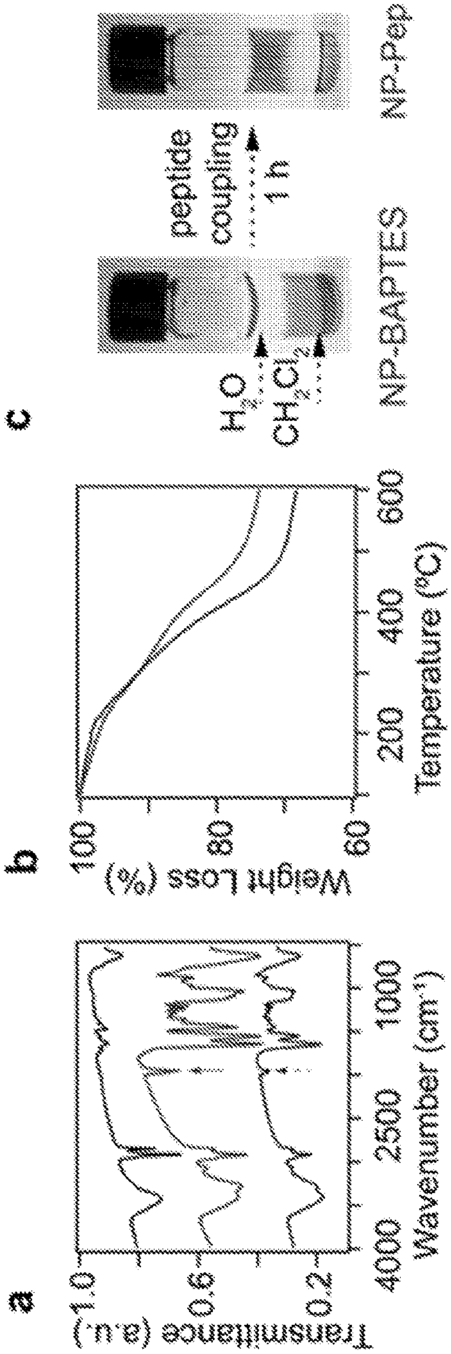
FIG. 3—Representative FTIR spectra (a) and TGA analysis (b) of various NPs: $Fe_3O_4$—OA NPs (top line), $Fe_3O_4$-BAPTES NPs (middle), and $Fe_3O_4$-peptide NPs (bottom). FTIR spectra are offset along the y-axis for clarity, with arrows denoting the characteristic allene (C═C═C) vibrational modes (1971, 1947 cm-1) corresponding to the silanized NPs. TGA analysis reveals increased organic content on NPs after peptide coupling. c, photographs of functionalized NPs in a biphasic mixture of dichloromethane and water, showing the change in NP-solvent compatibility before and after cTnI-peptide conjugation. NP-BAPTES is referred to as NP-Ctrl in the subsequent figures and text. Data are representative of n=3 independent experiments.

Following confirmation of such allenecarboxamide coupling chemistry, the BAPTES silanized NPs (NP-BAPTES) were then functionalized with the high affinity cTnI binding-peptide onto the NP surface, which is referred to as NP-Pep hereafter (FIG. 1 panel b). Transmission electron microscopy (TEM) revealed the uniformity and monodispersity of as-synthesized $Fe_3O_4$-oleic acid ($Fe_3O_4$-OA) NPs with an average diameter of 8.0±0.3 nm (FIG. 2 panel a) and confirmed that the morphology did not change significantly after BAPTES silanization (FIG. 2 panel b) and peptide surface functionalization (FIG. 2 panel c). Physicochemical properties of the surface functionalized NPs were measured at each reaction step to confirm the proper functionalization and elucidate the surface properties of the NPs. Fourier transform infrared spectroscopy (FTIR) analysis of the NP-BAPTES revealed strong peak intensities at 1970 and 1947 cm-1 characteristic of the allene-containing molecules (C═C═C) (Es-sebbar et al., 2014, Journal of Molecular Spectroscopy 305: 10-16) (FIG. 3 panel a). Moreover, the IR signatures of the as-synthesized NP-BAPTES were consistent and reproducible across different synthesis batches (FIG. 18). High-resolution magic angle spinning nuclear magnetic spectroscopy (HRMAS-NMR) performed on the NP-BAPTES confirmed the successful silanization of the NPs with BAPTES (FIG. 19).

After peptide coupling, the relative intensities of the characteristic allene peaks in the FTIR spectra were reduced, indicating the successful consumption of the allene groups upon peptide conjugation. Thermogravimetric analysis (TGA) of the NP-BAPTES revealed a 28% weight loss, accounting for a thin silane coating on the surface functionalized NPs (FIG. 3 panel b). Comparatively, analysis of the NP-Pep suggested the successful attachment of the 13-mer cTnI affinity peptide with an increased measured weight loss percentage (32%) after peptide coupling. From the difference in weight loss (~4%) between the NP-BAPTES and the final NP-Pep, a surface density of ~1.5 peptide/$nm^2$ per NP was inferred (Table 1). Furthermore, photographs of the NPs dispersed in a biphasic mixture of dichloromethane ($CH_2Cl_2$) and water illustrate the drastic change in NP-solvent compatibility before and after successful conjugation with the hydrophilic cTnI binding peptide (FIG. 3 panel c).

TABLE 1

Summary of materials characterization and surface functionalization analysis of various functionalized $Fe_3O_4$ NPs synthesized at a large-scale (120 mg).

| Particle | TEM Diameter (nm) | TGA Weight Loss (%) | Surface Density (ligands/$nm^2$) |
|---|---|---|---|
| $Fe_3O_4$-OA | 8.03 ± 0.08 | 44 | 14 |
| $Fe_3O_4$-BAPTES | 8.2 ± 0.2 | 26 | 5 |
| $Fe_3O_4$-Peptide | 8.3 ± 0.2 | 32 | 6 |

All errors indicate standard deviations from measurements on three independent batches of particles.

Figure 4:
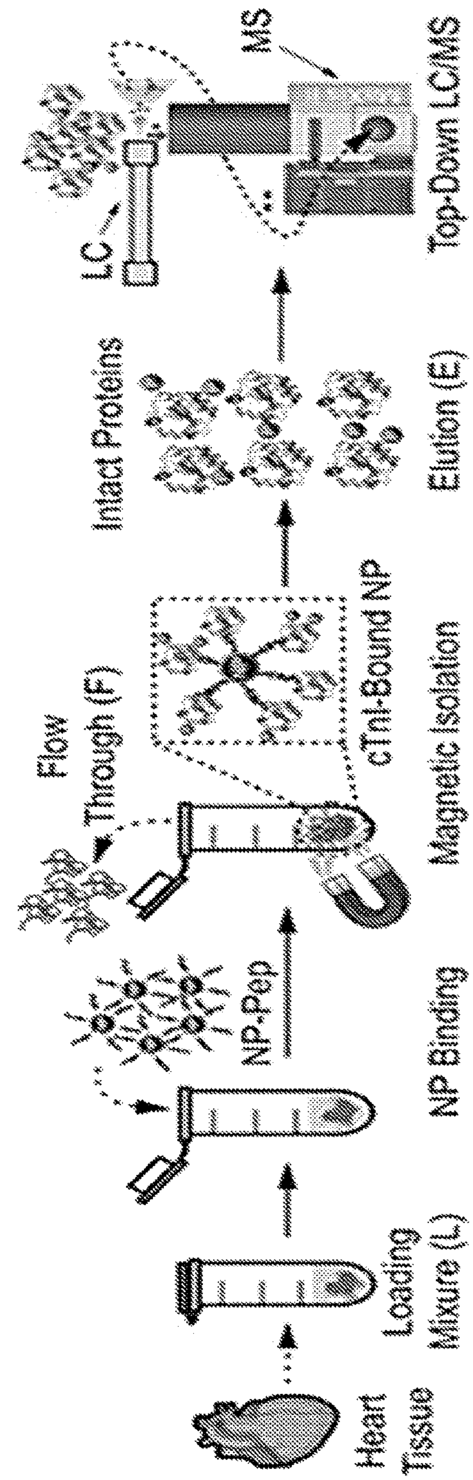
FIG. 4—Schematic illustration of the nanoproteomics strategy for cTnI enrichment and top-down MS analysis of cTnI proteoforms. Heart tissue extract (Loading mixture, L) is first incubated with the NP-Pep. Following magnetic isolation, the nonspecific proteins are removed as flow-through (F). The NPs are washed and the NP-bound proteins of interest are eluted (E) and analyzed by top-down MS.
Figure 5:
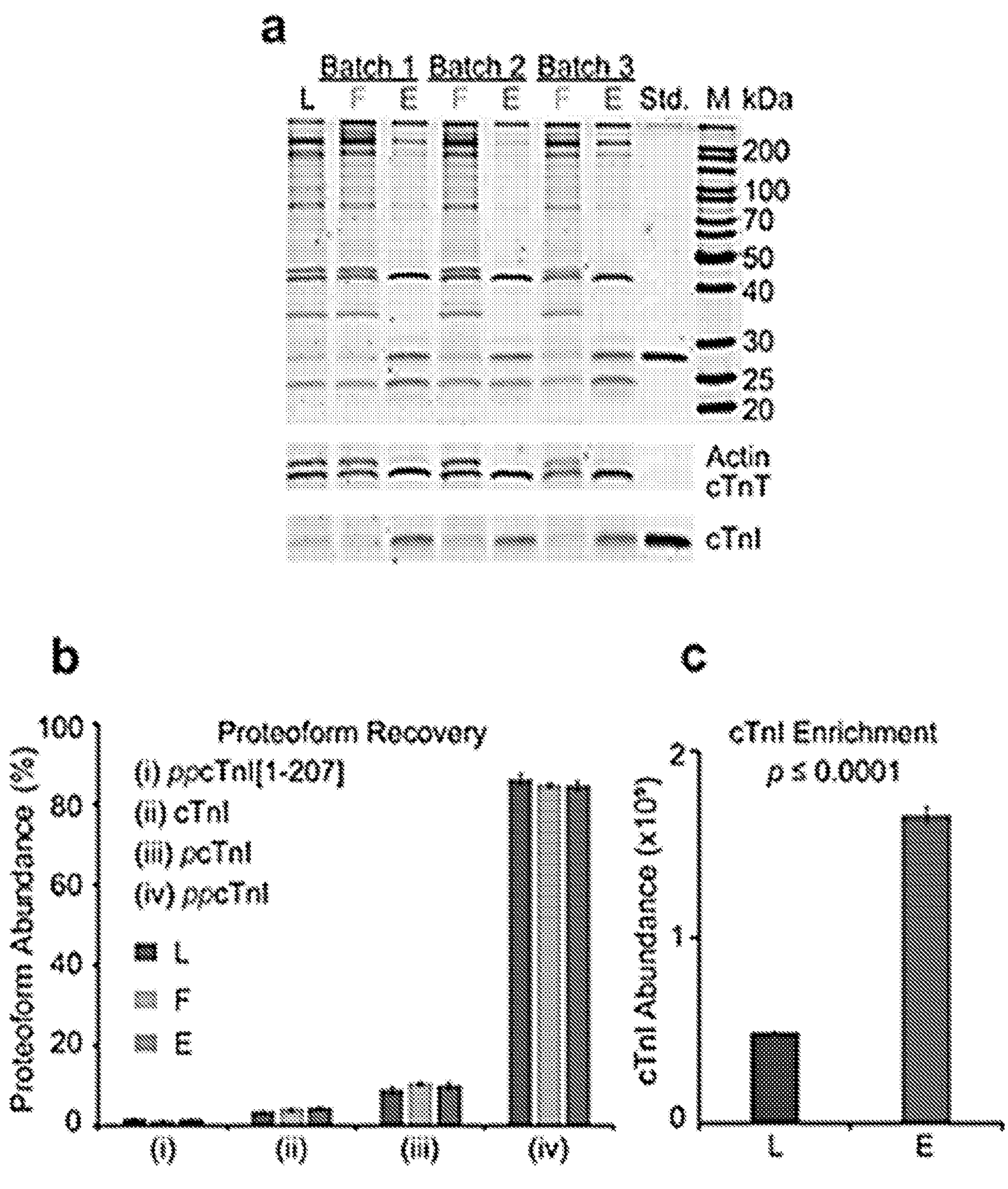
FIG. 5-*a*, SDS-PAGE visualizes the cTnI enrichment performance and demonstrates the high reproducibility obtained from three different NP-Pep syntheses (inter-batch). Equal amounts of NP-Pep (5 mg) were used for cTnI enrichment from sarcomeric protein extracts (300 μg) containing 0.3% cTnI obtained from a human donor heart. Equal amount (500 ng) of the L, F, and E was loaded on the gel. b, c, Evaluation of total cTnI proteoform recovery (b), and relative abundance of cTnI (c), before and after NP-Pep enrichment. The same L, F, and E shown in the gel from (a) were equally loaded (500 ng) for LC/MS analysis. The deconvoluted top-down mass spectra corresponding to cTnI proteoforms were used to calculate the relative abundance of each cTnI proteoform when normalizing for total protein amount injected. Proteoform abundance data (b) are representative of n=6 independent experiments with error bars indicating standard error of the mean. The relative abundance of cTnI was calculated using the top 5 most abundant charge states ions (average±0.2 m/z). cTnI relative abundance data are representative of n=3 independent experiments with error bars indicating standard error of the mean.

The cTnI enrichment performance of the NP-Pep were then evaluated using sarcomeric protein extracts prepared from human heart tissues (Table 2). SDS-PAGE was used to visualize the sarcomeric extracts, which was found to contain approximately 0.3% cTnI by ELISA, to confirm the reproduciblity of our protein extraction procedure (FIG. 20). The cTnI enrichment experiments using the functionalized NP-Pep (FIG. 4) proceeded as follows: (1) incubating the NP-Pep in the protein mixture, (2) magnetically isolating the NP-Pep to wash and remove unbound nonspecific proteins, and (3) eluting bound cTnI off of the NP-Pep using an acidic buffer to disrupt the intermolecular interactions between NP-Pep and the bound cTnI. After enrichment, the protein bands corresponding to cTnI and cTnT were far more prominent in the elution solutions compared to the initial loading mixtures which contained abundant sarcomeric proteins such as actin (FIG. 5 panel a). It was found that the salt (NaCl) concentration of the wash buffer was a critical parameter and could be tuned to promote effective cTnI enrichment using the NP-Pep (FIGS. 21 and 22). Subsequently, the highly effective and reproducible enrichment of cTnI from sarcomeric extracts by the NP-Pep was demonstrated from both three different intra- and inter-batch syntheses, as shown by SDS-PAGE (FIGS. 5, 23 and 24).

TABLE 2

Summary of sarcomeric protein extraction buffers and reagents. All heart tissue extracts were prepared using the described extraction protocol.

| Reagent (Stock concentration) | Final concentration | Purpose |
|---|---|---|
| Wash Buffer (pH 7.0) | | |
| $NaH_2PO_4$ (500 mM) | 5 mM | Maintain buffering capacity |
| $Na_2HPO_4$ (100 mM) | 5 mM | Maintain buffering capacity |
| $MgCl_2$ (100 mM) | 5 mM | Maintain ionic strength of medium |
| NaCl (137 mM) | 100 mM | Maintain ionic strength of medium |
| EGTA (100 mM) | 0.5 mM | Chelation of metal ions; inhibition of metalloproteases |
| Add remaining reagents immediately prior to performing wash protocol | | |
| Triton ™ X-100 (10% v/v) | 1% (v/v) | Solubilization of poorly soluble proteins |
| DTT (1M) | 5 mM | Reducing agent |
| Halt ™ protease inhibitor cocktail (100x) | 1x | Inhibition of Ser/Cys/Asp proteases |
| PMSF (25 mM in ethanol) | 1 mM | Inhibition of Ser proteases |
| Phosphatase inhibitor cocktail A (100x) | 1x | Inhibition of Ser/Thr/Tyr phosphatases |
| Protein Extraction Buffer (pH 7.5) | | |
| Tris (1M) | 25 mM | Maintain buffering capacity |
| $CaCl_2$ (100 mM) | 0.1 mM | Maintain ionic strength of medium |
| LiCl (3.5M) | 700 mM | Protein extraction |
| EGTA (100 mM) | 5 mM | Chelation of metal ions; inhibition of metalloproteases |
| Add remaining reagents immediately prior to performing extraction protocol | | |
| DTT (1M) | 5 mM | Reducing agent |
| Halt ™ protease inhibitor cocktail (100x) | 1x | Inhibition of Ser/Cys/Asp proteases |
| PMSF (25 mM in ethanol) | 1 mM | Inhibition of Ser proteases |
| Phosphatase inhibitor cocktail A (100x) | 1x | Inhibition of Ser/Thr/Tyr phosphatases |

It was further investigated whether high affinity cTnI-binding peptide functionalization onto the NPs was a critical factor for the high specificity enrichment by using the following NP controls: (1) NP-BAPTES as 'NP-Ctrl' with no peptide; (2) NP-BAPTES functionalized with peptide at an acidic pH to inhibit formation of the covalent Cys-thiol conjugate; (3) NP-BAPTES functionalized with a negative-control peptide containing alanine substitutions to reduce cTnI-binding affinity (FIG. 25), showed no appreciable cTnI enrichment. This confirms that only NPs properly functionalized with the high affinity cTnI-binding peptide (NP-Pep) allows for successful cTnI enrichment.

The cTnI enrichment performance of the NP-Pep were evaluated by top-down LC/MS analysis of the initial protein loading mixture, the resulting flow-through, and the final elution mixtures after cTnI enrichment by the NP-Pep, which allowed a bird's eye view of all cTnI proteoforms present for direct quantification of the ratios between modified cTnI proteoforms normalized to total cTnI. Importantly, the NP-Pep preserved all endogenous cTnI proteoform distributions and faithfully retained the endogenous cTnI PTM ratios at every step of the enrichment process with no artifactual modifications (FIG. 5 panel b). Moreover, the NP-Pep enriched cTnI over 3-fold ($p \leq 0.0001$) relative to the loading mixture (FIG. 5 panel c and 24 panels a-b). The simultaneous enrichment of cTnI and reliable preservation of the ratios between various cTnI proteoforms by the NP-Pep solves the major current challenge in cTnI PTM analysis (Soetkamp et al., 2017, Expert Review of Proteomics 14: 973-986) and enables the application of this nanoproteomics strategy for analysis of endogenous cTnI proteoforms toward clinical applications. In-depth top-down MS analysis of the intact cTnI proteoforms demonstrated the high reproducibility of this strategy (FIG. 6 panel a, and FIG. 24 panel c) and directly revealed all endogenous cTnI proteoforms present in the sarcomeric mixture obtained from a donor heart sample: bisphosphorylated cTnI with C-terminal truncation (ppcTnI[1-207]), unphosphorylated cTnI, monophosphorylated cTnI (pcTnI), and bisphosphorylated cTnI (ppcTnI) (Table 3).

TABLE 3

Figure 6:
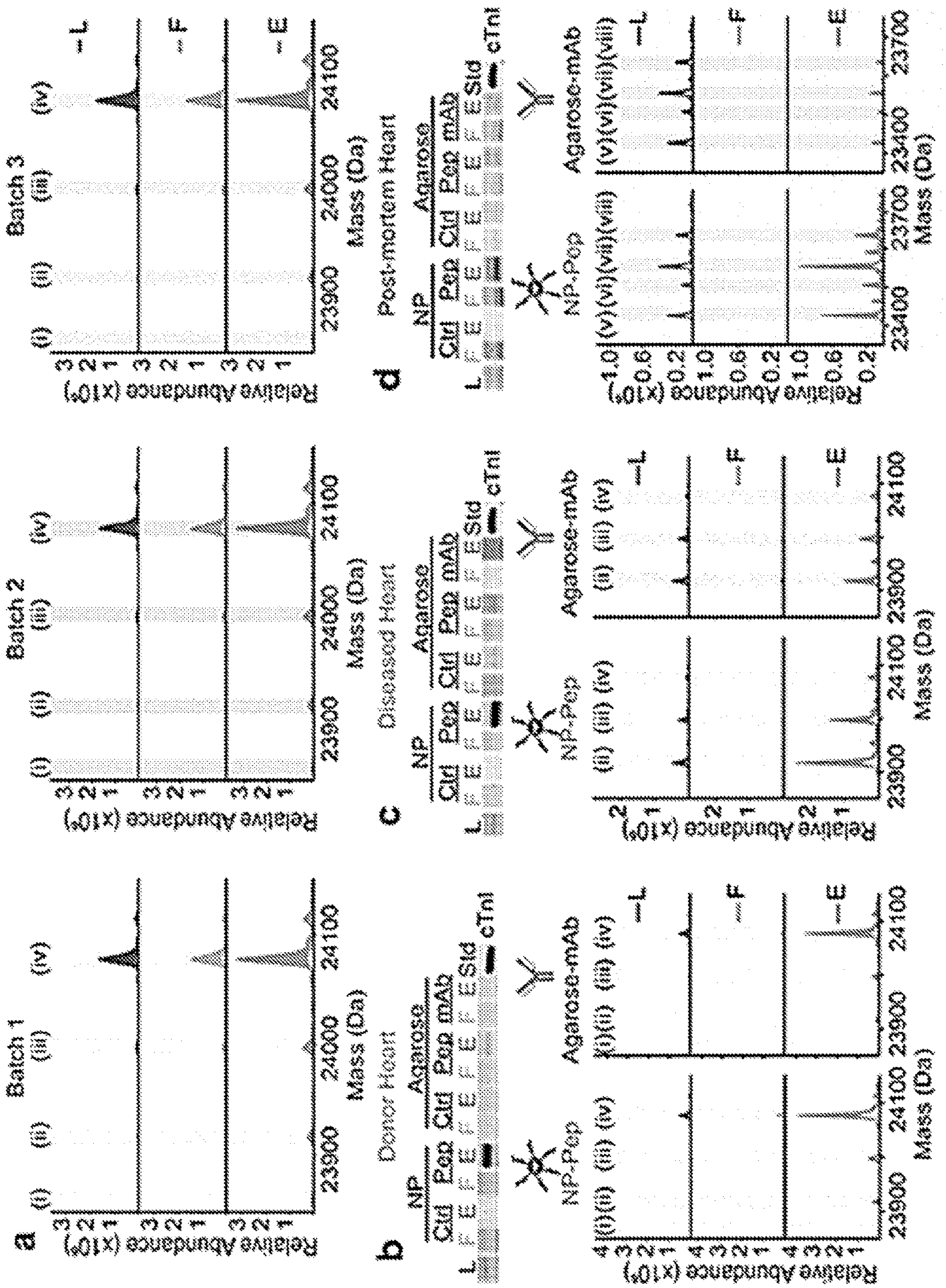
FIG. 6-*a*, MS-based evaluation of cTnI enrichment using three different synthetic batches of NP-Pep showing the reproducible enrichment performance of the NP-Pep. b-d, Enrichment from three different human heart samples using NP-Pep in comparison with agarose-mAb. Upper panels feature SDS-PAGE strips that visualize cTnI enrichment performance of NP-Pep and agarose-mAb. Equal protein amount (500 ng) of the loading mixture (L), flow-through (F), and elution mixture after enrichment (E) was loaded on the gels.

Summary of accurate mass measurement by top-down MS analysis of NP-Peptide platform enriched cTnl proteoforms (i)-(iv) corresponding to data presented in FIG. 6 panel a. Most abundant masses are shown.

| Sample | Proteoform | Observed Mass (Da) | Calculated Mass (Da) | Mass Error (ppm) |
|---|---|---|---|---|
| Batch 1 | (i) ppcTnl[1-206] | 23861.66 | 23861.68 | 0.8 |
| | (ii) cTnl | 23917.80 | 23917.83 | 1.3 |
| | (iii) pcTnl | 23997.78 | 23997.90 | 5.0 |
| | (iv) ppcTnl | 24077.73 | 24077.86 | 5.4 |
| Batch 2 | (i) ppcTnl[1-206] | 23861.75 | 23861.68 | 2.9 |
| | (ii) cTnl | 23917.92 | 23917.83 | 3.8 |
| | (iii) pcTnl | 23997.89 | 23997.90 | 0.4 |
| | (iv) ppcfnl | 24077.85 | 24077.86 | 0.4 |
| Batch 3 | (i) ppcTnl[1-206] | 23861.79 | 23861.68 | 4.6 |
| | (ii) cTnl | 23917.89 | 23917.83 | 2.5 |
| | (iii) pcTnl | 23997.89 | 23997.90 | 0.4 |
| | (iv) ppcTnl | 24077.85 | 24077.86 | 0.4 |

To illustrate the unique advantages of the NP-Pep system for cTnI enrichment compared to existing affinity purification systems, the cTnI enrichment performance of the NPs were then compared against a conventional agarose-based solid support functionalized with the same high affinity cTnI-binding peptide (Agarose-Pep) as well as with an anti-cTnI monoclonal antibody (M46; Agarose-mAb) that possesses a similar cTnI-binding epitope (amino acids 130 to 145) to that of the high affinity peptide (FIG. 6 panels b-d, FIGS. 26-28). In this way, the enrichment performance differences due to the choice of the affinity probe can be normalized, leaving the resulting cTnI enrichment performance differences to be a result of the underlying materials system. The cTnI enrichment performance of the two platforms were evaluated from sarcomeric extracts containing low amounts of cTnI (<700 ng) obtained from three different human heart tissue samples: a donor heart with normal cardiac function ("Donor"), a heart with dilated cardiomyopathy (DCM, "Diseased"), and a post-mortem heart with normal cardiac function. SDS-PAGE analysis revealed an intense cTnI band present in the NP-Pep elution mixtures (upper panels of FIG. 6 panels b-d) showing clearly that the NP-Pep effectively enriched cTnI across all cardiac samples possessing different cardiac pathologies. Comparatively, the Agarose-Pep and Agarose-mAb showed reduced cTnI enrichment in the same SDS-PAGE (upper panels of FIG. 6 panels b-d, and FIGS. 26-28). These results highlight the unique advantages that functionalized NPs possess for protein enrichment: a) comparable size and diffusion kinetics to proteins, promoting effective capture of low abundance proteins within complex mixtures (Walkey et al., 2012, Chemical Society Reviews 41: 2780-2799); b) high surface area per volume and high number of flexible binding sites, contributing to high ligand density and binding efficacy; c) inexpensive, simple, fast, and scalable synthesis, in contrast to antibodies (Roberts et al., 2019, Nano Research 12: 1473-1481).

Furthermore, rapid top-down LC/MS coupling reversed phase liquid chromatography (RPLC) to high-resolution MS revealed the molecular nature of the endogenous cTnI proteoforms found in the loading mixture (L), flow through (F) and elution (E) for each cardiac sample (lower panels of FIG. 6 panels b-d). The various cTnI proteoforms inherent to each of the heart tissue samples were unambiguously identified and characterized by accurate mass measurements (lower panels of FIG. 6 panels b-d, and Table 4). ppcTnI was found to be the predominant cTnI proteoform in the healthy donor heart (FIG. 6 panel b), whereas unphosphorylated cTnI was found to be the most abundance cTnI proteoform in the DCM heart (FIG. 6 panel c), which is consistent with previous reports that phosphorylation of cTnI could be considered as a biomarker for heart diseases (Soetkamp et al., 2017, Expert Review of Proteomics 14: 973-986). The highly abundant C-terminal truncated cTnI proteoforms found in the post-mortem samples were also identified and characterized (FIG. 6 panel d), which is consistent with previous reports (Dong et al., 2012, Journal of Biological Chemistry 287: 848-857). Despite the rich diversity of cTnI proteoforms between the various heart samples, NP-Pep was the only platform that could faithfully retain the endogenous cTnI proteoform distributions initially present in the donor (FIG. 6 panel b), DCM (FIG. 6 panel c), and post-mortem (FIG. 6 panel d) heart samples both before and after enrichment. Collectively, these results suggest that NP-Pep can be used as an effective antibody-replacement for cTnI enrichment.

TABLE 4

Summary of accurate mass measurement by top-down MS analysis of NP-Peptide platform enriched cTnI proteoforms (i)-(iv) corresponding to data presented in FIG. 6 panels b-d. Most abundant masses are shown.

| Heart Sample | Proteoform | [cTnI] | Observed Mass (Da) | Calculated Mass (Da) | Mass Error (ppm) |
|---|---|---|---|---|---|
| Donor | (i) ppcTnI[1-206] | 306 | 23861.73 | 23861.68 | 2.1 |
| | (ii) cTnI | ng/ml | 23917.87 | 23917.83 | 1.7 |
| | (iii) pcTnI | | 23997.82 | 23997.90 | 3.3 |
| | (iv) ppcTnI | | 24077.80 | 24077.86 | 2.5 |
| Dilated | (ii) cTnI | 482 | 23917.71 | 23917.83 | 5.0 |
| cardio- | (iii) pcTnI | ng/ml | 23997.77 | 23997.90 | 5.4 |
| myopathy | (iv) ppcTnI | | 24077.73 | 24077.86 | 5.4 |
| Post- | (v) cTnI[1-205] | 465 | 23426.67 | 23426.59 | 3.4 |
| mortem | (vi) pcTnI[1-205] | ng/ml | 23506.65 | 23506.55 | 4.3 |
| | (vii) cTnI[1-206] | | 23554.76 | 23554.68 | 3.4 |
| | (viii) pcTnI[1-206] | | 23634.72 | 23634.65 | 3.0 |

Although top-down MS methods have been developed for the comprehensive analysis of various cTnI proteoforms simultaneously after they are extracted from tissues (Dong et al., 2012, Journal of Biological Chemistry 287: 848-857; Zhang et al., 2011, Journal of Proteome Research 10: 4054-4065; and Zabrouskov et al., 2008, Mol Cell Proteomics 7: 1838-1849), MS detection of low abundance cTnI in the blood remains an unsolved challenge due to the extreme complexity and dynamic range (~1012) of the blood proteome and the presence of highly abundant blood proteins (~90% of total blood mass) such as human serum albumin (HSA) (Anderson et al., 2002, History, Character, and Diagnostic Prospects 1: 845-867; and Rifai et al., 2006, Nature Biotechnology 24: 971-983). To this end, cTnI enrichment was performed from human serum spiked-in with the cTnI extracted from the same donor, DCM, and post-mortem heart samples as in FIGS. 4-6. The endogenous cTnI obtained from the different human heart samples were used as the reference cTnI sources and served to mimic cTnI found in the blood. SDS-PAGE analysis revealed the striking contrast in cTnI enrichment performance and nonspecific blood protein resistance between the NP-Pep versus the conventional agarose platform (FIG. 7 panel a). Importantly, the NP-Pep demonstrated impressive resistance to nonspecific adsorption from the highly abundant HSA in serum, in contrast to the Agarose-Pep and Agarose-mAb.

Even though cTnI was undetectable in the original serum mixture due to the low abundance of cTnI compared to the higher abundance blood proteins, the NP-Pep elution fraction showed nearly complete depletion of HSA and significant enrichment of cTnI relative to the loading mixture (FIG. 7 panel a). SDS-PAGE analysis of the cTnI enrichment from human serum spiked-in with DCM (FIG. 29) and post-mortem (FIG. 30) cTnI references also showed consistent HSA depletion by the NP-Pep, in contrast with the Agarose-Pep and Agarose-mAb. This is further confirmed by analysis of the extracted ion chromatograms (EICs) corresponding to HSA and cTnI obtained from the same serum spike-in samples between the NP-Pep and the agarose platforms (FIG. 7 panel b, and FIGS. 31-35). Unlike the NP-Pep, the agarose platforms retained a large amount of HSA in the elution fraction, which likely limited its enrichment efficacy for cTnI. Importantly, the deconvoluted top-down mass spectra of the serum spike-in cTnI samples illustrate that not only did the NP-Pep enrich cTnI in greater abundance, it also was able to capture lower abundant proteoforms (cTnI, pcTnI) from the healthy donor cTnI reference compared to the Agarose-Pep and Agarose-mAb (FIG. 8 panel a). Moreover, the deconvoluted top-down mass spectra for HSA (FIG. 8 panel b) further revealed the significantly improved HSA resistance that the NP-Pep possess, compared to that of the Agarose-Pep and the Agarose-mAb where HSA remains persistent throughout the enrichment process.

These results illustrate the remarkable benefits of the functionalized NPs compared to conventional antibody-based approaches: (1) the NPs are capable of effective cTnI enrichment across all tested serum samples and cardiac pathologies; (2) the NPs retain all endogenous cTnI proteoforms from serum without introducing artifactual modification; (3) the NPs show reproducible and highly significant depletion of HSA after NP-Pep enrichment (FIG. 35) without the use of immunoaffinity depletion columns which can cause up to 90% sample loss of cTnI by other reports (Kuhn et al., 2009, Clinical Chemistry 55: 1108; and Schneck et al., 2018, Analytical and Bioanalytical Chemistry 410: 2805-2813).

After determining the absolute cTnI amount using an ELISA assay (FIG. 36), the limit of detection (LOD) was calculated for cTnI using top-down MS by injecting controlled amounts of cTnI (3.1 ng to 0.006 ng) purified from the same healthy donor tissue that was used in FIGS. 4-8. Top-down RPLC/MS with a CaptiveSpray (CS) ionization source fitted to a maxis II ETD mass spectrometer was sufficiently sensitive to detect cTnI at a concentration as low as 0.06 ng/ml (FIG. 9 panel a, and FIGS. 37-38), which nearly meets the diagnostic cutoff of 0.04 ng/ml for AMI by clinical ELISA (Soetkamp et al., 2017, Expert Review of Proteomics 14: 973-986; and Apple et al., 2017, Clinical Chemistry 63: 73-81). After demonstration of the capability of top-down MS for accurate detection and analysis of cTnI at low concentrations, the detection sensitivity of the current NP-Pep platform was then evaluated for cTnI enrichment from human serum. Remarkably, the NP-Pep was able to enrich cTnI from serum with a LOD as low as 0.75 ng/ml (FIG. 9 panel b, and FIG. 39). This integrated nanoproteomics strategy with front-end specific enrichment of cTnI using the NP-Pep followed by top-down MS analysis enabled the detection, identification, and characterization of cTnI proteoforms from human serum at concentrations less than 1 ng/ml (FIG. 9 panel c). Future optimizations in automating the NP-Pep enrichment workflow to reduce sample handling and transfer steps, as well as additional modern instrumentation improvements, may further improve the LOD toward the diagnostic cutoff value used by contemporary cTnI ELISA (≤0.04 ng/ml).

After successfully enriching cTnI from human serum, this nanoproteomic strategy was applied to six different human serum samples each consisting of unique cTnI references obtained from different donor, diseased, or post-mortem heart tissues to mimic the enormous diversity of circulating cTnI proteoforms that could be found in blood for demonstrating the comprehensive analysis of cTnI from human serum (FIG. 11). NP-Pep demonstrated effective cTnI enrichment which allowed for the subsequent comprehensive analysis of various cTnI proteoforms from human serum by the bird's eye view provided by top-down MS (FIG. 10, and FIG. 40). Similar to previous results on tissue-level analysis of cTnI obtained from donor hearts (FIG. 10 panels i and ii), the endogenous cTnI was found to exist primarily in its phosphorylated (mono- and bisphosphorylated) state. However, drastic decrease of phosphorylated cTnI was detected in the DCM hearts as compared to healthy donor hearts (FIG. 10 panels iii and iv), which is consistent with contractile dysfunction in DCM (Zhang et al., 1995, Journal of Biological Chemistry 270: 30773-

30780). Moreover, cTnI degradation due to proteolysis was clearly seen in the post-mortem cardiac samples (FIG. 10, panels v, vi) which yielded severely modified C-terminal truncations from the full-length cTnI (Labugger et al., 2000, Circulation 102: 1221-1226). Despite the rich diversity of cTnI proteoforms present in each of these cardiac samples (Table 5), NP-Pep demonstrated high effective and unbiased cTnI proteoform enrichment across all tested samples. The cTnI proteoform ratios present in the initial sarcomeric protein extracts from tissue did not significantly change after serum spike-in and incubation in pooled human serum followed by subsequent NP-Pep enrichment at 4° C. (Katrukha et al., 1998, Clinical Chemistry 44: 2433). Although previous works have utilized 'bottom-up' MS methodologies for the detection and quantification of cTnI-specific peptides, the analysis of peptides digested from proteins cannot ultimately distinguish between proteoforms and is unable to quantify putative PTMs across entire protein sequences (Kuhn et al., 2009, Clinical Chemistry 55: 1108; and Schneck et al., 2018, Analytical and Bioanalytical Chemistry 410: 2805-2813). For the first time, this nanoproteomics strategy enables proteoform-resolved analysis of all intact cTnI proteoforms from human serum at clinically relevant concentrations.

TABLE 5

Summary of accurate mass measurement by top-down MS analysis of NP-Peptide platform enriched cTnI proteoforms from human serum corresponding to data presented in FIG. 10. Most abundant masses are shown.

| Heart Sample | Proteoform | [cTnI] | Observed Mass (Da) | Calculated Mass (Da) | Mass Error (ppm) |
|---|---|---|---|---|---|
| (i) Donor | pcTnI | 11.05 | 23997.70 | 23997.90 | 8.3 |
| | ppcTnI | ng/ml | 24077.64 | 24077.86 | 9.1 |
| (ii) Donor | cTnI | 10.69 | 23917.77 | 23917.83 | 2.5 |
| | pcTnI | ng/ml | 23997.70 | 23997.90 | 8.3 |
| | ppcTnI | | 24077.64 | 24077.86 | 9.1 |
| (iii) Dilated cardio-myopathy | cTnI | 20.72 | 23917.77 | 23917.83 | 2.5 |
| | pcTnI | ng/ml | 23997.77 | 23997.90 | 5.4 |
| (iv) Dilated cardio-myopathy | cTnI | 22.84 | 23917.72 | 23917.83 | 4.6 |
| | pcTnI | ng/ml | 23997.77 | 23997.90 | 5.4 |
| (v) Post-mortem | cTnI[1-205] | 11.66 | 23426.40 | 23426.59 | 8.1 |
| | pcTnI[1-205] | ng/ml | 23506.37 | 23506.55 | 7.7 |
| | cTnI[1-206] | | 23554.49 | 23554.68 | 8.1 |
| | pcTnI[1-206] | | 23634.43 | 23634.65 | 9.3 |
| (vi) Post-mortem | cTnI[1-205] | 15.22 | 23426.56 | 23426.59 | 1.3 |
| | pcTnI[1-205] | ng/ml | 23506.52 | 23506.55 | 1.3 |
| | cTnI[1-206] | | 23554.65 | 23554.68 | 1.3 |
| | pcTnI[1-206] | | 23634.61 | 23634.65 | 1.7 |

In summary, this example demonstrates the first comprehensive proteoform-resolved cTnI assay enabled by nanotechnology and top-down MS. Carefully designed surface functionalized NPs can directly capture and enrich cTnI from blood with high specificity and reproducibility, while simultaneously depleting high-abundance blood proteins such as HSA. The proteoforms of enriched cTnI could be detected and quantified by a rapid LC/MS-based top-down proteomics with high sensitivity (LOD 0.75 ng/ml). Furthermore, all cTnI proteoforms could be completely recovered after a highly specific and effective enrichment from serum by NP-Pep and the cTnI proteoform signature resolved by LC-MS can be directly linked to the phenotypes. This nanoproteomics cTnI assay could be further developed into a clinical diagnostic assay after testing in a large human cohort by specifically enriching cTnI from patient blood samples and comprehensively detecting all cTnI proteoforms to establish a robust relationship between cTnI proteoforms and disease etiology. It is envisioned that this nanoproteomics-enabled cTnI assay will be the next generation comprehensive assay to provide previously unachievable high-resolution proteoform-resolved molecular signature of cTnI for accurate diagnosis, prognosis, and risk stratification of patients with ACS and non-ACS chronic diseases toward precision medicine.

ELISA-Based cTnI Enrichment Efficiency Quantification of NP-Pep and Agarose-mAb.

ELISA-based colorimetric quantification of cTnI standards (left dashed box) and enrichment samples (right dashed box) were performed (FIG. 41, panel a). All samples were dispensed in triplicate and the assay was performed according to the manufacturer's instructions. The ELISA assay used capture antibodies targeting cTnI amino acids 18-28 and 86-90, with detection antibodies targeting cTnI amino acids 41-49. FIG. 41, panel b shows the ELISA-based standard curve (0 ng, 0.4 ng, 1.25 ng, 2.5 ng, 7.5 ng, 20 ng) used for quantification of cTnI amount before enrichment and after enrichment by NP-Pep or Agarose-mAb, and panel c shows a summary of enrichment performance results for NP-Pep (tissue/serum) and Agarose-mAb (serum). The cTnI enrichment factor and cTN percent recovery are calculated as follows:

$$cTnI\text{ enrichment factor} = \frac{\text{concentration } cTnI \text{ After Enrichment } \left(\frac{ng}{\text{mL}}\right)}{\text{concentration } cTnI \text{ Before Enrichment } \left(\frac{ng}{\text{mL}}\right)},$$

$$cTnI\text{ enrichment factor} = \frac{\text{concentration } cTnI \text{ After Enrichment } \left(\frac{ng}{\text{mL}}\right)}{\text{concentration } cTnI \text{ Before Enrichment } \left(\frac{ng}{\text{mL}}\right)}.$$

Top-down LC-MS/MS characterization of cTnI arising from the various biological samples after enrichment. Representative CID fragment ions obtained by cTnI arising from donor heart $$\left(y_{76}^{13+},\ y_{209}^{30+},\ b_{86}^{12+},\ \text{and }\ b_{155}^{21+}\right),$$

diseased heart $$\left(y_{76}^{12+},\ y_{42}^{7+},\ b_{31}^{5+},\ \text{and }\ b_{86}^{12+}\right),$$

and post-mortem heart $$\left(y_{76}^{8+},\ y_{51}^{9+},\ b_{86}^{14+},\ \text{and }\ b_{31}^{5+}\right)$$

sources are shown in FIG. 42. cTnI was found to be primarily in its bisphosphorylated state in the donor heart (ppcTnI; Ser22, and Ser23) (SEQ ID NO: 4), unphosphorylated state in the diseased heart (cTnI) (SEQ ID NO:5), and in a proteolytically degraded form in the post-mortem heart (cTnI[1-206]) (SEQ ID NO:6 with methionine removed). Theoretical ion distributions are indicated by the dots and mass accuracy errors are listed for each fragment ion. FIG. 43 shows protein sequence fragmentation mapping of the specific proteoform of cTnI corresponding to the fragment ion data obtained from each cTnI source in FIG. 42 (SEQ ID NOs: 4-6). All matched sequences contained N-terminally acetylated cTnI proteoforms following Met exclusion. The amino acid sequence was based on the entry name TNNI3_human obtained from the UniProtKB sequence database (SEQ ID NO: 4).

Preservation of cTnI PTM profiles by NP-Pep from serum reflecting different cardiac pathophysiologies. FIG. 44 shows representative deconvoluted mass spectra corresponding to cTnI proteoforms originating from a donor heart (a), a diseased dilated cardiomyopathie heart (b), and a post-mortem heart (c) before serum spike-in (i), after serum spike-in (ii), and after NP-Pep enrichment of human serum spiked with cTnI (iii). Equal amounts of NP-Pep (5 mg) were used for the cTnI enrichments and equal amounts (500 ng) were loaded for LC/MS analysis.

Materials and Reagents. All chemicals and reagents were purchased from MilliporeSigma (St. Louis, MO, USA) and used as received without further purification unless otherwise noted. Sodium oleate (97%), was purchased from Tokyo Chemical Industry (TCI) America (Portland, OR, USA). The high affinity cTnI peptide (95%) with C-terminal Cysteine residue (HWQIAYNEHQWQC-SEQ ID NO: 2) and the nonspecific peptide (95%) with C-terminal Cysteine residue (HWNMAANEHMQWC-SEQ ID NO: 3) were purchased from GenScript USA Inc. (3-aminopropyl)triethoxysilane (APTES) was purchased from Gelest (Morrisville, PA, USA). Human male AB serum (H4522) was purchased from Millipore Sigma (St. Louis, MO, USA). Human cardiac troponin I-C monoclonal antibody (M46, cat. #sc-52277) and phosphatase inhibitor cocktail A (cat. #sc-45044) were purchased from Santa Cruz Biotechnology, Inc. N-hydroxysuccinimide (NHS) activated agarose slurry (cat. #26200) and Halt™ Protease inhibitor cocktail were purchased from ThermoFisher Scientific (Rockford, IL, USA). Human cardiac troponin I ELISA kit (AccuBind® ELISA, cat. #3825-300) was purchased from Monobind Inc. (Lake Forest, CA, USA). Extraction solutions were made in nanopure deionized water ($H_2O$) from Milli-Q® water (MilliporeSigma). Bradford protein assay reagent was purchased from Bio-Rad (Hercules, CA, USA). 12.5% gel (10 comb or 15 comb well, 10.0 cm×10.0 cm, 1.0 mm thick) for SDS-Polyacrylamide Gel Electrophoresis (SDS-PAGE) was home-made. DynaMag™-2 Magnet and Thermo Scientific™ Cimarec+™ stirring hotplate were purchased from ThermoFisher Scientific (Rockford, IL, USA). Amicon, 0.5 mL cellulose centrifugal filters with a molecular-weight cutoff (MWCO) of 10 kDa was purchased from MilliporeSigma.

Synthesis of But-3-nyoic acid. 3-butynoic acid was prepared from the oxidation of 3-butyn-1-ol following the reported procedure (Abbas et al., 2014, Angewandte Chemie International Edition, 53(29): 7491-7494). 135 mL water was added to a 500 mL single neck RBF fitted with magnetic stirrer bar. 65% $HNO_3$(0.51 mL, 5 mol %, 7.5 mmol), $Na_2Cr_2O_7$ (0.45 g, 1 mol %, 1.5 mmol) and $NaIO_4$ (70.60 g, 2.2 eq., 330 mmol) were subsequently added to the RBF and the mixture was stirred vigorously on an ice bath for 15 min. 11.3 mL of 3-butyn-1-ol (1 eq., 150 mmol) dissolved in 135 mL of chilled water was added to this mixture slowly and the reaction mixture was stirred overnight. After this time, the product was extracted in diethyl ether (100 mL×6). All the fractions were combined and dried over anhydrous magnesium sulfate. Solvent was evaporated on a rotary evaporator to give an orange/yellowish viscous liquid. Subsequent addition of dichloromethane and removal of solvent under vacuum 4-5 times yielded 6.56 g of an off white/yellowish solid (52% yield). $^1H$ NMR (500 MHz, Chloroform-d) δ 3.38 (d, 2H, J=2.7 Hz), 2.25 (t, 1H, J=2.7 Hz); 13C NMR (125 MHz, Chloroform-d) δ 173.8, 74.8, 72.4, 25.6.

Synthesis of N-(3-(triethoxysilyl)propyl)buta-2,3-dienamide (BAPTES). But-3-nyoic acid (2.10 g, 25.0 mmol, 1 eq.), 2-chloro-1-methylpyridinium iodide (6.39 g, 25.0 mmol, 1 eq.), and $CH_2Cl_2$ (250.0 mL, 0.10 M) were added to an oven dried 500 mL three-neck flask fitted with a reflux condenser. The solution was heated to reflux under $N_2$. In a separate flask, (3-aminopropyl) thiethoxysilane (5.85 mL, 25.0 mmol, 1 eq.) and N,N-diisopropylethylamine (8.71 mL, 50.0 mmol, 1 eq.) were diluted with 125.0 mL $CH_2Cl_2$, and added to the refluxing three-neck flask by syringe. The reaction mixture was allowed to reflux for 1 hour, and then N,N-Diisopropylethylamine (4.36 mL, 25.0 mmol, 1 eq.) was additionally added to fully isomerize the propargylic isomer to N-(3-(triethoxysilyl)propyl)buta-2,3-dienamide. The reaction was allowed to reflux overnight, and the product was concentrated by rotary evaporation. The crude product was suspended in ethyl acetate, centrifuged at 5,000 rpm for 5 min, and the supernatant was concentrated by rotary evaporation. The product was purified with flash column chromatography using a gradient of 50:50 ethyl acetate:hexane to 100:0 ethyl acetate:hexane to obtain a clear, orange oil (67% yield). $^1H$ NMR (500 MHz, Chloroform-d) δ 5.99 (s, 1H), 5.62 (t, J=6.6 Hz, 1H), 5.20 (d, J=6.7 Hz, 2H), 3.83 (q, J=7.0 Hz, 6H), 3.31 (q, J=6.7 Hz, 2H), 1.66 (m, 2H), 1.24 (t, J=7.0 Hz, 9H), 0.66 (m, 2H).

Synthesis of iron-oleate precursor. Iron oleate was synthesized using a previously established method (Park et al., 2004, Nature Materials, 3(12), 891-895). In a typical synthesis, iron (III) chloride hexahydrate (10.8 g, 40 mmol) was first dissolved in a mixture of 80 mL ethanol and 60 mL nanopure water in a three-neck round bottom flask (500 mL) containing a Teflon-coated egg-shaped (1¼"×⅝") magnetic stir bar. Sodium oleate (36.5 g, 120 mmol) was then quickly added to the iron chloride solution along with 140 mL n-hexane. The resulting solution was then allowed to stir until the sodium oleate was completely dissolved. Afterwards, the reaction solution was heated to 70° C. for a 4 h reflux under a $N_2$ blanket. Upon completion, the reaction solution was cooled to room temperature, and the upper organic layer containing the iron oleate was washed three times with 30 mL nanopure water in a 250 mL separatory funnel. After washing, excess hexane was then removed by rotary evaporation. Finally, the resulting iron oleate was transferred into a 100 mL round bottom flask, connected to a Schlenk line, and placed under vacuum overnight. For later storage, the iron oleate was well sealed in a glass vial and placed in a desiccator.

Synthesis of 8 nm magnetite ($Fe_3O_4$) nanocrystals. Iron oleate (10 mmol, 9.0 g) and oleic acid (5.5 mmol, 1.56 g) were added into a three-neck round bottom flask (250 mL) with a solvent mixture of 1-octadecene: 1-tetradecene (40 g: 10 g). The mixture was stirred and degassed on a Schlenk line at 110° C. for 3 h. The mixture was then placed under nitrogen flow and the reaction solution was heated to 300° C. at a heating rate of 3.3° C./min using a temperature controller. Reaction time was counted starting from when 300° C. was reached. After 1 h, the reaction solution was quickly cooled to room temperature by blowing air across the reaction flask. The resulting iron-oxide nanocrystals were precipitated using ethanol, isolated via centrifugation (5,000 rpm, 20 min), and then washed with three precipitation/redispersion cycles (5,000 rpm, 20 min) using ethanol. The resulting nanocrystals were then dried under vacuum, weighed, and redispersed in n-hexane at a concentration of 20 mg/mL for further use.

Synthesis of $Fe_3O_4$-BAPTES NPs (NP-BAPTES). In a typical optimized large-scale synthesis of silane functionalized NPs, $Fe_3O_4$ NPs (6 mL from a 20 mg/mL stock) were added to anhydrous n-hexane (300 mL) in a 500 mL round bottom flask equipped with a Teflon-coated egg-shaped magnetic stir bar (1¼"×5") to achieve a total NP concentration of 0.4 mg/mL. After the reaction mixture was heated to 60° C. with stirring (900 rpm), BAPTES (1.65 mL) was added dropwise to the flask for a 0.55% (v/v) total concentration of trialkoxysilane reagent, followed by dropwise addition of a small amount of acetic acid (30 μL) for an acidic catalyst concentration of 0.01% (v/v). After reaction under stirring for 24 h, the precipitate was collected and washed one time with n-hexane, one time with n-hexane/acetonitrile (v/v, 4:1), and one more time with n-hexane via centrifugation (5,000 rpm, 10 min) to remove excess silane molecules and surfactants. The NPs were then dried under vacuum for later use.

Synthesis of $Fe_3O_4$-BAPTES-Peptide NPs (NP-Pep). 10 mg of NP-BAPTES were added to a 4-dram vial and dispersed in 2 mL of acetonitrile. 10 mg of cTnI-binding peptide (HWQIAYNEHQWQC-SEQ ID NO: 2) were added to a separate 4-dram vial and dissolved in 8 mL of nanopure water. The pH of the peptide solution was adjusted to pH 8.0 by the addition of 75 μL of 1.0 M ammonium carbonate buffer pH 9.0 during simultaneous water bath sonication. The pH-adjusted peptide solution was added into the 4-dram vial containing the NP dispersion under water bath sonication. The NP reaction mixture was allowed react under sonication for 1 h and later collected into Eppendorf tubes for washing. The peptide-functionalized NPs were washed three times with water via centrifugation (15,000 rcf, 5 min) and subsequently isolated magnetically with a DynaMag to remove unreacted peptide. The resulting peptide functionalized NPs were redispersed in water at a concentration of 5 mg/mL.

Material characterization. Transmission electron microscopy (TEM) samples were prepared by pipetting a 10 μL drop of as-synthesized NPs at a concentration of 0.125 mg/mL onto a copper TEM grid with lacey carbon film. TEM was conducted on a FEI T12 microscope operated at 120 kV, equipped with a Gatan CCD image system with digital micrograph software program. Transmission Fourier transform infrared (FTIR) spectroscopy measurements were recorded on a Bruker Equinox 55 FT-IR spectrometer in the range of 4,000 cm-1 to 400 cm-1 at 2 cm-1 resolution on NPs in a potassium bromide (KBr) pellet, at a sample mass loading of 0.33 wt. %. Thermogravimetric analysis (TGA) was carried out using a TA Instruments Q500 thermal analysis system under a $N_2$ atmosphere and at a constant heating rate of 10° C./min from 100° C. to 600° C. All samples were first heated to 100° C. and held at that temperature for 3 min to remove adsorbed water.

Small molecule analysis by FTICR-MS. All small molecule samples (<3 kDa) were diluted 500-fold in 50:50:0.1 (acetonitrile:water:formic acid) MS-grade solvent for positive electrospray ionization mode analysis. Samples were analyzed by direct infusion using a TriVersa Nanomate system (Advion BioSciences, Ithaca, New York) coupled to a solarix XR 12-Tesla Fourier Transform lon Cyclotron Resonance Mass spectrometer (FTICR-MS, Bruker Daltonics). For the nano-electrospray ionization source (TriVersa Nanomate), the desolvating gas pressure was set at 0.5 PSI and the voltage was set to 1.2 to 1.6 kV versus the inlet of the mass spectrometer. Mass spectra were acquired with an acquisition size of 1M, in the mass range between 150 and 2000 m/z (with a resolution of 270,000 at 400 m/z), and 50 scans were accumulated for each sample, lons were accumulated in the collision cell for 0.05 s, and a time of flight of 0.500 ms was used prior to their transfer to the ICR cell. For collisionally activated dissociation MS/MS experiments, the collision energy was varied from 10 to 20V. Tandem mass spectra were output from the DataAnalysis software and analyzed using MASH Suite Pro software. All the program-processed data were manually validated. The methods described here correspond to the data presented in FIGS. 12, 16 and 17.

Sarcomeric protein extraction from human cardiac tissue samples. All protein extraction procedures were performed in a cold room (4° C.) using freshly prepared buffers. All human cardiac tissue was obtained from the University of Wisconsin Hospital and Clinic. The procedure for the collection and de-identification of human cardiac tissue was approved by the Institutional Review Board of the University of Wisconsin-Madison. 500 mg of tissue was homogenized in wash buffer (5 mM $NaH_2PO_4$, 5 mM $Na_2HPO_4$, 5 mM $MgCl_2$, 0.5 mM EGTA, 0.1 M NaCl, 1% Triton X-100, 5 mM DTT, 1 mM PMSF, 1×HALT protease inhibitor cocktail, and 1× phosphatase inhibitor cocktail A, pH 7.4) using a Polytron electric homogenizer (Model PRO200; PRO Scientific, Oxford, CT, USA) on ice. The resulting homogenate was centrifuged at 10,000 g (Avanti J-25i; Beckman Coulter, Fullerton, CA, USA) for 10 min at 4° C. After centrifugation, the supernatant was removed, and the pellet was washed once more with wash buffer. The wash supernatant was removed, and the pellet was re-suspended in protein extraction buffer (0.7 M LiCl, 25 mM Tris, 5 mM EGTA, 0.1 mM $CaCl_2$), 5 mM DTT, 1 mM PMSF, 1×HALT protease inhibitor cocktail, and 1× phosphatase inhibitor cocktail A, pH 7.5), and the suspension was agitated on a nutating mixer (Thermo Scientific, Boston, MA, USA) at 4° C. for 45 min. The sarcomeric protein extract was centrifuged at 16,000 g (Centrifuge 5415R, Eppendorf, Hamburg, Germany) for 10 min at 4° C. and the resulting supernatant was again centrifuged at 21,000 g for 30 min to remove all tissue debris. The concentration of the tissue lysate was determined by Bradford protein assay. Samples were stored at −80° C. for later study. The buffers and reagent preparation for the methods described here correspond to the data presented in Table 2.

cTnI enrichment using NP-Pep from human cardiac sarcomere extracts. NP-Pep (5 mg) was resuspended in a 2 mL Eppendorf Protein Lo-Bind tube with equilibration buffer (50 mM Tris, pH 7.5, 150 mM LiCl). The NPs were then centrifuged at 15,000 rcf for 2 min at 4° C., isolated from the solution using the DynaMag, and the supernatant was removed. Equilibration buffer was then added to the NPs, the mixture was sonicated and vortexed to prepare for protein loading. Protein loading mixture (L), from tissue extract was diluted to a final volume of 1 mL with a buffered solution (50 mM Tris, pH 7.4, 150 mM LiCl) to a total protein loading of 0.3 mg/mL and was added to the NP-Pep mixture, at a NP concentration of 5 mg/mL. After this mixture was agitated on a nutating mixer at 4° C. for 40 min, the NPs were centrifuged at 15,000 rcf for 2 min at 4° C., and then isolated from the solution using the DynaMag. The supernatant was collected and saved as the flow-through (F) fraction. The isolated NPs were then washed three times with a wash buffer (50 mM Tris, pH 7.5, 300 mM NaCl; 0.20 mL/mg NP) following the same centrifugation and magnetic isolation steps to remove unbound, non-specific proteins. To elute the bound cTnI, 500 L of 200 mM glycine hydrochloride buffer (pH 2.2) was added. After centrifugation and magnetic isolation, the resulting supernatant was collected as the elution fraction (E). All protein fractions (L, F, and E) were desalted prior to MS analysis using a 10 kDa MWCO filter (Amicon, 0.5 mL, cellulose, MilliporeSigma) and buffered exchanged using 0.2% formic acid in nanopure water. To evaluate the enrichment performance of the functionalized NPs, all collected fractions (L, F, and E) were equally loaded (500 ng), separated using a polyacrylamide gel (12.5%), and stained with SYPRO Ruby (Thermo Fisher Scientific, Inc., Rockford, IL, USA) fluorescent dye. The gel was imaged using a ChemiDoc™ MP Imaging System (170-8280; Bio-Rad, Hercules, CA, USA).

cTnI enrichment using the agarose solid-support platform from human cardiac sarcomere extracts. mAb or peptide was conjugated to the agarose beads following the manufacturer's recommendations and blocked with a 1.0 M ethanolamine solution, pH 7.4. Protein loading mixture (L) was incubated with 500 μL of mAb or peptide-conjugated agarose beads in a disposable affinity column for 40 min on a nutating mixer at 4° C. After incubation, the supernatant was collected and saved as the flow-through (F) fraction. The agarose beads were then washed three times with 1 mL of 50 mM Tris pH 7.4 and 300 mM NaCl to elute unbound proteins. Subsequently, the bound proteins were eluted using four equal fractions of 500 μL of 200 mM glycine hydrochloride, pH 2.2. The four elution fractions (E) were pooled and all protein fractions (L, F, and E) were desalted prior to MS analysis using a molecular weight cutoff filter (Amicon, 0.5 mL, cellulose, MilliporeSigma) and buffered exchanged using 0.2% formic acid in nanopure water.

cTnI enrichment using the NP-Pep from human serum. Serum loading mixtures were prepared by serially spiking in human sarcomeric protein extracts into 200 μL of serum (10 mg protein) from human male AB plasma and diluting the serum mixture to a final volume of 1 mL using a buffered solution of 50 mM Tris pH 7.4 and 1.0 M LiCl. The concentrations of cTnI spiked into serum samples were measured using a cTnI AccuBind ELISA kit (Monobind Inc., Lake Forest, CA, USA). The cTnI spiked human serum loading mixture (L) was incubated with 5 mg of peptide-functionalized NPs in a 2 mL Eppendorf Lo-Bind tube. After this mixture was agitated on a nutating mixer at 4° C. for 40 min, the NPs were centrifuged at 15,000 rcf for 2 min at 4° C., and then isolated from the solution using a DynaMag. The supernatant was collected and saved as the flow-through (F) fraction. The NPs were then washed three times with 1 mL of 50 mM Tris pH 7.4 and 300 mM NaCl following the same centrifugation and magnetic isolation steps to remove unbound, non-specific proteins. To elute the bound cTnI, 500 L of 200 mM glycine hydrochloride buffer (pH 2.2) was added. After centrifugation and magnetic isolation, the resulting supernatant was collected as the elution fraction (E). All protein fractions (L, F, and E) were desalted prior to MS analysis using a 10 kDa MWCO filter (Amicon, 0.5 mL, cellulose, MilliporeSigma) and buffer exchanged using 0.2% formic acid in nanopure water.

cTnI enrichment using the agarose solid-support platform from human serum. The serum loading mixture was prepared in the same way as in the NP serum enrichment protocol and the mAb or peptide conjugate agarose beads were prepared as previously described. The serum loading mixture (L) was added to 500 μL of mAb or peptide-conjugated agarose beads in a disposable affinity column, and agitated for 40 min on a nutating mixer at 4° C. After incubation, the supernatant was collected and saved as the flow-through (F) fraction. The agarose beads were then washed three times with 1 mL of 50 mM Tris pH 7.4 and 300 mM NaCl to elute unbound proteins. Subsequently, the bound proteins were eluted using four equal fractions of 500 μL of 200 mM glycine hydrochloride, pH 2.2. The four elution fractions (E) were pooled and all protein fractions (L, F, and E) were desalted prior to MS analysis using a 10 kDa MWCO filter (Amicon, 0.5 mL, cellulose, MilliporeSigma) and buffered exchanged using 0.2% formic acid in nanopure water.

Comparison of the cTnI enrichment performance of the NP-Pep platform against the agarose-mAb or agarose-Pep platform from human cardiac tissue extracts. The enrichment workflow was performed in a cold room held at 4° C. to minimize possible artifactual protein modifications, such as oxidation. NP-Control (NP-BAPTES), NP-Pep ($Fe_3O_4$-BAPTES-Peptide), Agarose-Control beads (no coupling), Agarose-Pep beads, and Agarose-mAb beads were incubated with sarcomeric extract obtained from completely de-identified healthy donor heart tissue, diseased heart tissue of dilated cardiomyopathy (DCM), and post-mortem heart tissue containing 306 ng cTnI, 482 ng cTnI, and 465 ng cTnI in the protein extract, respectively. cTnI values were determined by ELISA quantification as previously described. The loading mixture (L), flow through (F), and elution mixture (E) were collected, desalted using a 10 kDa MWCO filter, and buffer exchanged prior to SDS-PAGE gel analysis or LC-MS analysis as described in the tissue enrichment protocol. The methods described here correspond to the data presented in FIG. 6 and FIGS. 26-28.

Comparison of the cTnI enrichment performance of the NP-Pep platform against the agarose-mAb or agarose-Pep platform from human serum spiked with cTnI. The enrichment workflow was performed in a cold room held at 4° C. to minimize possible artifactual protein modifications, such as oxidation. NP-Control (NP-BAPTES), NP-Pep ($Fe_3O_4$-BAPTES-Peptide), Agarose-Control beads (no coupling), Agarose-Pep beads, and Agarose-mAb beads were incubated with in a protein loading mixture containing human male AB serum (10 mg) and sarcomeric tissue extract obtained from healthy donor heart tissue, diseased heart tissue of DCM, and post-mortem heart tissue containing 306 ng cTnI, 482 ng cTnI, and 465 ng cTnI in the protein extract, respectively. cTnI values were determined by ELISA quantification as previously described. The loading mixture (L), flow through (F), and elution mixture (E) were collected, desalted using a 10 kDa MWCO, and buffer exchanged prior to SDS-PAGE gel analysis or LC-MS analysis as described in the tissue enrichment protocol. The methods described here correspond to the data presented in FIGS. 4, 5, and 31-36.

Typical reverse phase chromatography (RPC) procedure. Reverse phase chromatography (RPC) was performed with a nanoACQUITY UPLC system (Waters; Milford, MA, USA). Mobile phase A (MPA) contained 0.2% formic acid in nanopure water, and mobile phase B (MPB) contained 0.2% formic acid in 50:50 acetonitrile:isopropanol. Prior to injection, protein samples were desalted by washing through 10 kDa MWCO filters using 0.2% formic acid in nanopure water six times. For each injection, 500 ng of desalted protein sample was loaded onto a BIOshell A400 C4, 3.4 μm, 15 cm×200 μm capillary column. The column was placed in a column heater set at 60° C. with a constant 3 L/min flow rate. The RPC gradient consisted of the following concentrations of MPB: 10% MPB at 0 min, 10% at 5 min, 65% at 45 min, 90% at 50 min, held at 90% until 55 min, adjusted back to 10% at 55.1 min, and held at 10% until 60 min. Each run was 60 min long.

Top-down MS analysis. Samples eluted from RPC separation were ionized using a CaptiveSpray source (Bruker Daltonics, Bremen, Germany) into a Maxis II Q-TOF mass spectrometer (Bruker Daltonics, Bremen, Germany) for online LC-MS and LC-MS/MS experiments. End plate offset and capillary voltage were set at 500 and 4000 V, respectively. The nebulizer was set to 0.3 bar, and the dry gas flow rate was 4.0 L/min at 200° C. The quadruple low mass cutoff was set to 500 m/z during MS and 200 m/z during MS/MS. Mass range was set to 200-3000 m/z and spectra were acquired at 1 Hz for LC-MS runs. All data were collected with OtofControl 3.4 (Bruker Daltonics), analyzed and processed in DataAnalysis 4.3 (Bruker Daltonics). Maximum Entropy algorithm (Bruker Daltonics) was used to deconvolute all mass spectra with the resolution set to 80,000. Sophisticated Numerical Annotation Procedure (SNAP) peak-picking algorithm (quality factor: 0.4; signal-to-noise ratio (S/N): 3.0; intensity threshold: 500) was applied to determine the monoisotopic mass of all detected ions. Fragmentation ion lists consisting of monoisotopic mass, intensity and charge were generated from DataAnalysis 4.3, and were subsequently converted to MSAlign files. TopPIC was used to search against the Uniprot-Swissprot human database which was released on Nov. 9, 2018 and contains 20395 protein sequences. Fragment mass tolerance was set to 15 ppm. All identifications were validated with statistically significant P and E values (<0.01) and satisfactory numbers of assigned fragment (>10). Tandem mass spectra were output from the DataAnalysis software and analyzed using MASH Suite Pro software (Cai et al., 2016, Molecular & Cellular Proteomics, 15(2): 703-714). The spectra were deconvoluted with a signal-to-noise ratio of 3 and a cutoff fit score of 60%. All the program-processed data were manually validated to obtain accurate sequence and PTM information. Chromatograms in FIGS. 7, 31 and 33 shown were smoothened by Gauss algorithm with a smoothing width of 1.67 s. To quantify protein expression across samples, top 5 most abundant charge states ions (average±0.2 m/z) of all major proteoforms from the same protein were retrieved collectively as one extracted peak in the extracted ion chromatogram (Lin et al., 2019, Molecular & Cellular Proteomics, 18(3): 594-605). The area under curve was manually determined for each protein isoform using DataAnalysis. To quantify protein modifications, the relative abundances of specific modifications were calculated as their corresponding percentages among all the detected protein forms in the deconvoluted averaged mass.

Statistical analysis. All statistical data were presented as the mean±standard error of the mean (SEM). Student's t-test was performed between group comparisons to evaluate the statistical significance of variance for the validation of the simultaneous quantification of protein expression and modification changes. Differences among means were considered significant at $p<0.05$. All error bars shown in the figures were based on SEMs.

Having now fully described the present invention in some detail by way of illustration and examples for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

When a group of materials, compositions, components or compounds is disclosed herein, it is understood that all individual members of those groups and all subgroups thereof are disclosed separately. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure. Additionally, the end points in a given range are to be included within the range. In the disclosure and the claims, "and/or" means additionally or alternatively. Moreover, any use of a term in the singular also encompasses plural forms.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements.

One of ordinary skill in the art will appreciate that starting materials, device elements, analytical methods, mixtures and combinations of components other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. The invention illustratively described herein suitably may be practiced in the absence of any element or elements, limitation or limitations which is not specifically disclosed herein. Headings are used herein for convenience only.

All publications referred to herein are incorporated herein to the extent not inconsistent herewith. Some references provided herein are incorporated by reference to provide details of additional uses of the invention. All patents and publications mentioned in the specification are indicative of the levels of skill of those skilled in the art to which the invention pertains. References cited herein are incorporated by reference herein in their entirety to indicate the state of the art as of their filing date and it is intended that this information can be employed herein, if needed, to exclude specific embodiments that are in the prior art.

We claim:

1. A method for analyzing a cardiac protein in a sample, said method comprising the steps of:

a) adding functionalized nanoparticles to the sample containing the cardiac protein, wherein the functionalized nanoparticles comprise superparamagnetic nanoparticles and one or more probe molecules attached to each superparamagnetic nanoparticle, wherein the one or more probe molecules are able to preferentially bind to the cardiac protein, thereby generating protein bound nanoparticles, and wherein each of the one or more probe molecules comprise an amino acid sequence having SEQ ID NO: 1 HWQIAYNEHQWQ b) magnetically isolating the protein bound nanoparticles, thereby generating isolated nanoparticles;

c) eluting the cardiac protein from the isolated nanoparticles, thereby generating an enriched fraction of the cardiac protein that can be used for further chemical and/or biological analysis; and d) ionizing the enriched fraction of the cardiac protein and performing mass spectrometry (MS) analysis on the ionized cardiac protein.

2. The method of claim 1 wherein the functionalized nanoparticle further comprises one or more organosilane coupling molecules on the surface of the superparamagnetic nanoparticle and the one or more probe molecules are attached to the superparamagnetic nanoparticle through said one or more coupling molecules.

3. The method of claim 2 wherein the one or more coupling molecules comprise N-(3(triethoxysilyl)propyl) buta-2,3-dienamide (BAPTES), N-(3(trimethoxysilyl)propyl)buta-2,3-dienamide (BAPTMS), N-(3(triethoxysilyl) propyl)-3-butynamide, N-(3(trimethoxysilyl)propyl)-3-butynamide, or combinations thereof.

4. The method of claim 1 wherein the cardiac protein is cardiac troponin I (cTnI) or cardiac troponin T (cTnT).

5. The method of claim 1 wherein the cardiac protein is a proteoform of cTnI or cTnT.

6. The method of claim 1 wherein the sample is a blood, serum, plasma, tissue sample, or combinations thereof.

7. The method of claim 1 wherein the sample is taken from a patient, and the method further comprises making a diagnosis of a cardiac disease based on the presence of the cardiac protein(s) in the sample from the patient.

8. The method of claim 7 wherein the cardiac disease comprises acute coronary syndrome (ACS) and non-ACS chronic diseases.

9. The method of claim 7 wherein the cardiac disease is acute myocardial infarction (AMI).

10. The method of claim 1 wherein the nanoparticles are not bound to or comprise an antibody.

11. A method for analyzing a cardiac protein in a sample, said method comprising the steps of:

a) adding functionalized nanoparticles to the sample containing the cardiac protein, wherein the functionalized nanoparticles comprise one or more probe molecules attached to each functionalized nanoparticle, wherein the one or more probe molecules are able to preferentially bind to the cardiac protein, thereby generating protein bound nanoparticles, and wherein each of the one or more probe molecules comprise an amino acid sequence having SEQ ID NO: 1 HWQIAYNEHQWQ;

b) isolating the protein bound nanoparticles, thereby generating isolated nanoparticles;

c) eluting the cardiac protein from the isolated nanoparticles, thereby generating an enriched fraction of the cardiac protein that can be used for further chemical and/or biological analysis; and d) ionizing the enriched fraction of the cardiac protein and performing mass spectrometry (MS) analysis on the ionized cardiac protein.

* * * * *